(12) United States Patent
Gomtsyan et al.

(10) Patent No.: US 8,071,762 B2
(45) Date of Patent: Dec. 6, 2011

(54) FUSED COMPOUNDS THAT INHIBIT VANILLOID RECEPTOR SUBTYPE 1 (VR1) RECEPTOR

(75) Inventors: Arthur R. Gomtsyan, Vernon Hills, IL (US); Erol K. Bayburt, Gurnee, IL (US); Chih-Hung Lee, Vernon Hills, IL (US); John R. Koenig, Chicago, IL (US); Robert G. Schmidt, Waukegan, IL (US); Kirill A. Lukin, Vernon Hills, IL (US); Gilles Chambournier, Ann Arbor, MI (US); Margaret Chi-Ping Hsu, Vernon Hills, IL (US); Marvin R. Leanna, Grayslake, IL (US); Russell D. Cink, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 876 days.

(21) Appl. No.: 12/112,105

(22) Filed: Apr. 30, 2008

(65) Prior Publication Data

US 2008/0287676 A1 Nov. 20, 2008

Related U.S. Application Data

(60) Division of application No. 10/864,068, filed on Jun. 9, 2004, now Pat. No. 7,375,126, and a continuation-in-part of application No. 11/258,980, filed on Oct. 26, 2005, now Pat. No. 8,026,256.

(60) Provisional application No. 60/477,894, filed on Jun. 12, 2003.

(51) Int. Cl.
C07D 401/02 (2006.01)
C07D 231/56 (2006.01)
(52) U.S. Cl. ........ 544/59; 546/146; 546/211; 548/362.5
(58) Field of Classification Search .................. None
See application file for complete search history.

(56) References Cited

U.S. PATENT DOCUMENTS

| | | | |
|---|---|---|---|
| 3,647,819 A | 3/1972 | Kirchner et al. | |
| 3,711,610 A | 1/1973 | Kirchner et al. | |
| 3,814,711 A | 6/1974 | Eloy et al. | |
| 4,958,026 A | 9/1990 | Schoellkopf et al. | |
| 5,362,878 A | 11/1994 | Chang et al. | |
| 5,444,038 A | 8/1995 | James et al. | |
| 5,646,140 A | 7/1997 | Sugg et al. | |
| 5,656,634 A | 8/1997 | Chang et al. | |
| 5,760,246 A | 6/1998 | Biller et al. | |
| 6,001,860 A | 12/1999 | Hamanaka | |
| 6,291,476 B1 | 9/2001 | Kordik | |
| 6,472,414 B1 | 10/2002 | Biller et al. | |
| 6,511,998 B2 | 1/2003 | Kordik et al. | |
| 6,555,539 B2 | 4/2003 | Reich et al. | |
| 6,858,577 B1 | 2/2005 | Zhang et al. | |
| 6,933,311 B2 | 8/2005 | Lee et al. | |

FOREIGN PATENT DOCUMENTS

| | | |
|---|---|---|
| EP | 0587180 | 9/1993 |
| EP | 1256574 | 2/2001 |
| WO | 9850347 | 11/1998 |
| WO | 03014064 | 2/2003 |
| WO | 03014064 A | 2/2003 |
| WO | 03055484 | 7/2003 |
| WO | 03055848 | 7/2003 |
| WO | WO-03055648 A1 | 7/2003 |
| WO | 03070247 | 8/2003 |
| WO | 03080578 | 10/2003 |
| WO | 03097586 | 11/2003 |

OTHER PUBLICATIONS

Landsiedel-Maier, D., "Structure activity relationship of homochiral 7-substituted 1-aminoindans as 5-HT1 A receptor ligands", Archiv Der Pharmazie, vol. 331, 1998, pp. 59-71, XP002296522.
Sterling, J., "Novel dual inhibitors of AchE and MAO," Journal for Medicinal Chemistry, vol. 45, No. 24, 2002, pp. 5260-5279, XP002296523.
Poste et al. "Lipid Vesicles as Carriers for Introducing Biologically Active Materials into Cells", Methods in Cell Biology, Academic Press, 1976, Chapter 4, vol. 14, 33-71.
Berge, et al. "Pharmaceutical Salts," Journal of Pharmaceutical Sciences, vol. 66, No. 1 et seq. (1977).
Caterina, et al., "The capsaicin receptor: a heat-activated ion channel in the pain pathway," Nature, vol. 389 (1997), pp. 816-824. Caterina, et al., "The Vanilloid Receptor: A Molecular gateway to the pain pathway," Annual Review of Neuroscience vol. 24 (2001), pp. 487-517.
Caterina, et al., "Impaired Nociception and pain sensation in mice lacking the capsaicin receptor," Science, vol. 288, (2000), pp. 306-313.
Collier, et al., Br. J. Pharmacol. Chemother, vol. 32 (1968), pp. 295-310.
Davis, et al., "Vanilloid receptor-1 is essential for inflammatory thermal hyperalgesia," Nature, vol. 405 (2000) pp. 183-187.
Fowler, et al., "Intravesical treatment of overactive bladder," Urology, vol. 55, No. Supp 5A (2000), pp. 60-64.
Hayes, et al., "Cloning and functional expression of a human orthologue of rat vanilloid receptor-1," Pain, vol. 88 (2000), pp. 205-215.

(Continued)

Primary Examiner — Zinna Northington Davis
(74) Attorney, Agent, or Firm — Lisa V. Mueller; Michael Best & Friedrich LLP

(57) ABSTRACT

The present invention discloses novel compounds of general formula (I)

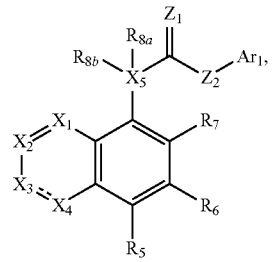

or a pharmaceutically acceptable salt or prodrug thereof (in which $X_1$-$X_5$, $R_5$-$R_{8b}$, $Z_1$-$Z_2$ and $Ar_1$ are defined herein), a method for inhibiting the VR1 receptor in mammals using these compounds, a method for controlling pain in mammals, and pharmaceutical compositions including those compounds and a process for making those compounds.

5 Claims, 8 Drawing Sheets

OTHER PUBLICATIONS

IUPAC 1974 Recommendation for Section E, Fundamental Sterochemistry, Pure App. Chem., vol. 45 (1976), pp. 13-30.

Landsiedel-Maier, "Structure Activity Relationship of Homonchiral 7-Substituted 1-Aminoindans as 5-HT1A Receptor Ligands," Archie Der Pharmazie, vol. 331 (1998), pp. 59-71.

Nolano, et al., "Topical capsaicin in humans: parallel loss of epidermal nerve fibers and pain sensation," Pain, vol. 81 (1999), pp. 135-145.

Pircio, et al., "A New Method for the Evaluation of Analgesic Activity using Adjuvant-Induced Arthritis in the Rat" Eur J. Pharmacol. vol. 31, No. 2 (1975), pp. 207-215.

Prescott, et al., Methods in Cell Biology, Academic Press, New York, N.Y. vol. 14, No. 33 et seq. (1976).

Sterling, "Novel Dual Inhibitors of AchE and MAO," Journal of Medicinal Chemistry, vol. 45, No. 24 (2002), pp. 5260-5279.

Thummel, et al., "Polyaza Cavity-Shaped Molecules. Annelated Derivatives of 2-(2'-Pyridyl)-1,8-naphthyridine and 2,2'-Bi-1,8-naphthyridine" J. Org. Chem., vol. 49 (1984) pp. 2208-2212.

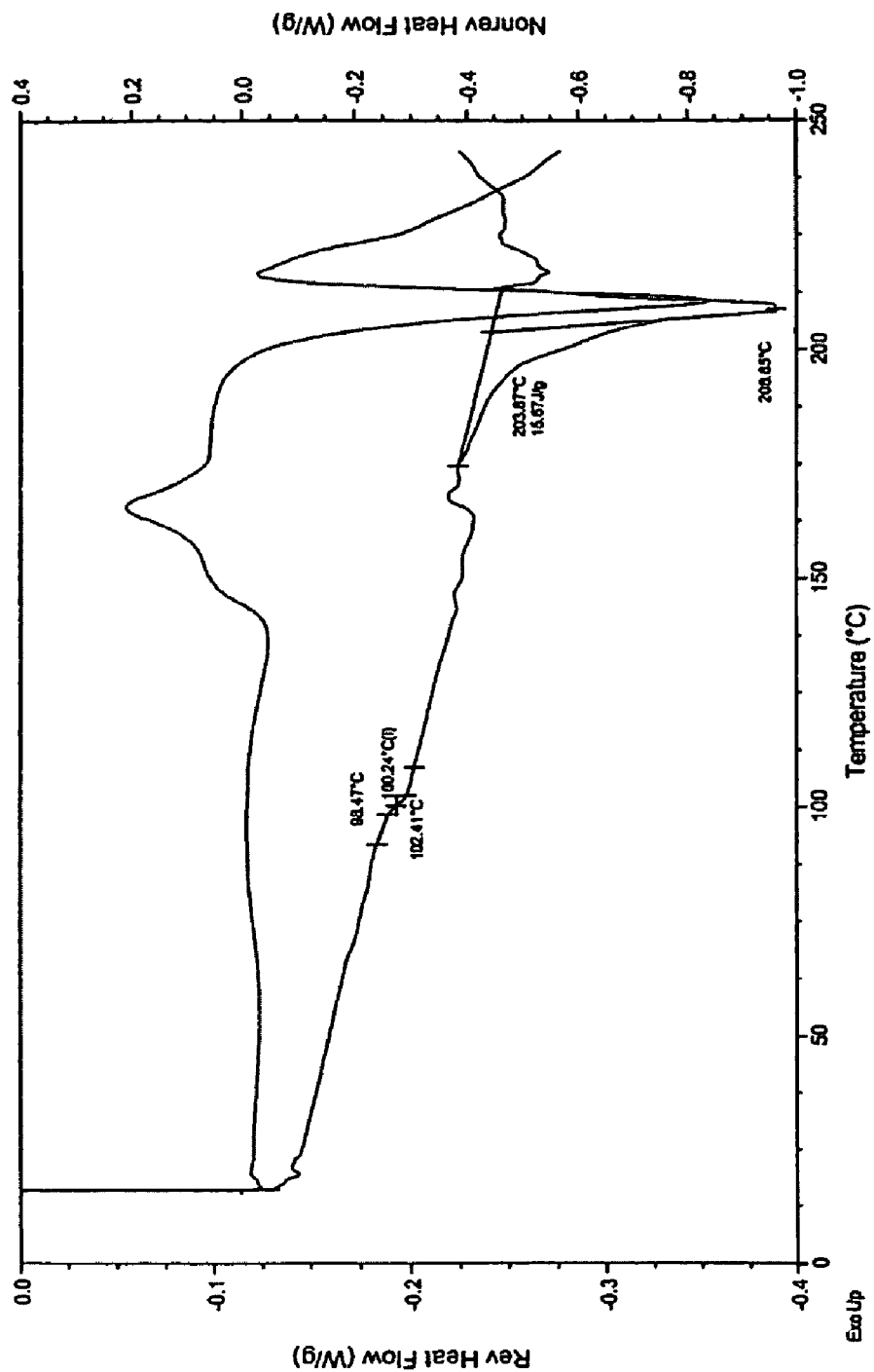
Figure 1. Differential Scanning Calorimetry (DSC) for amorphous N-[(1R)-5-tert-butyl-2,3-dihydro-1H-inden-1-yl]-N'-1H-indazol-4-ylurea (Example 13A)

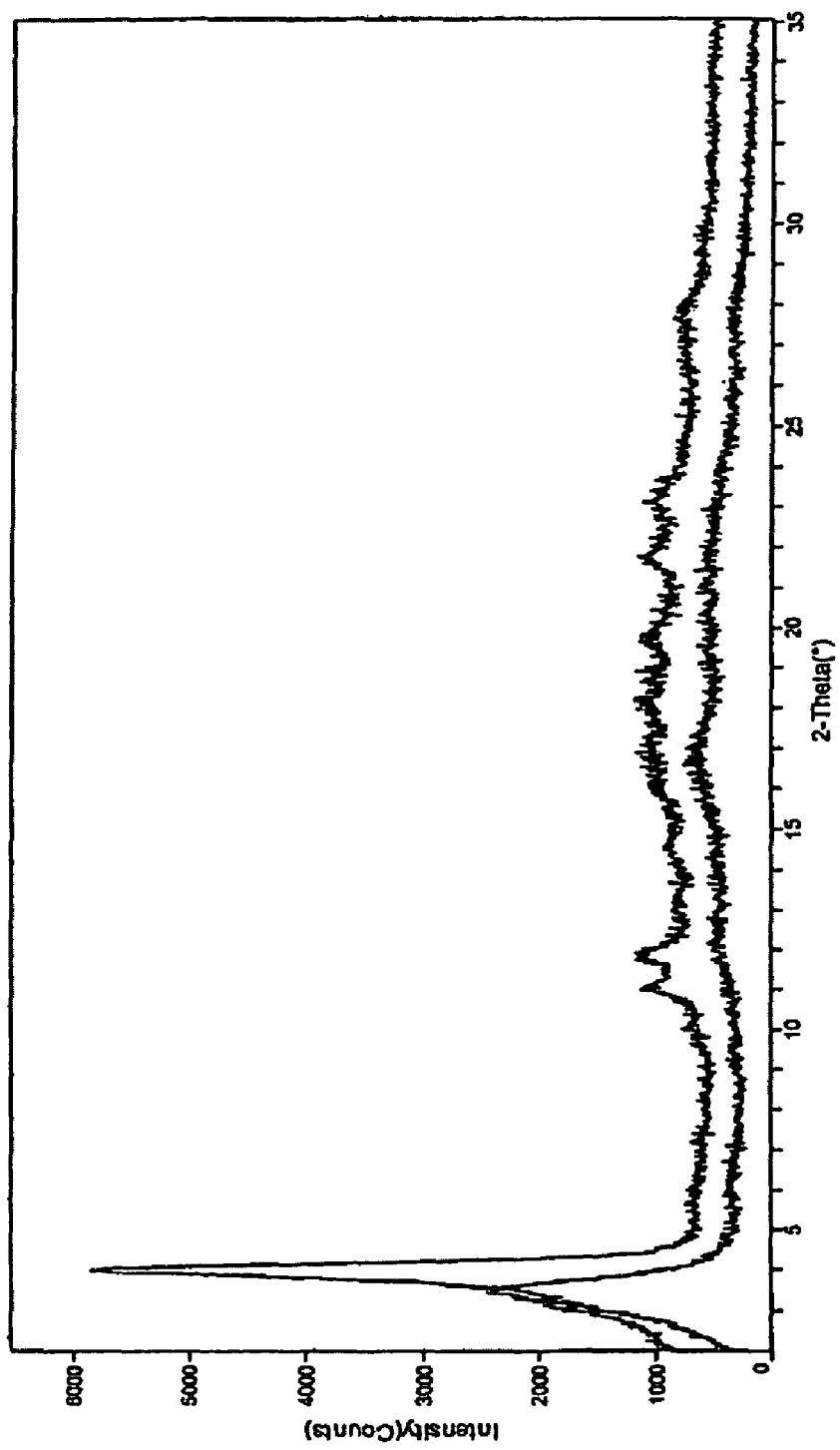
Figure 2. X-ray diffraction (XRD) for amorphous N-[[(1R)-5-tert-butyl-2,3-dihydro-1H-inden-1-yl]]-N'-1H-indazol-4-ylurea (Example 13A).

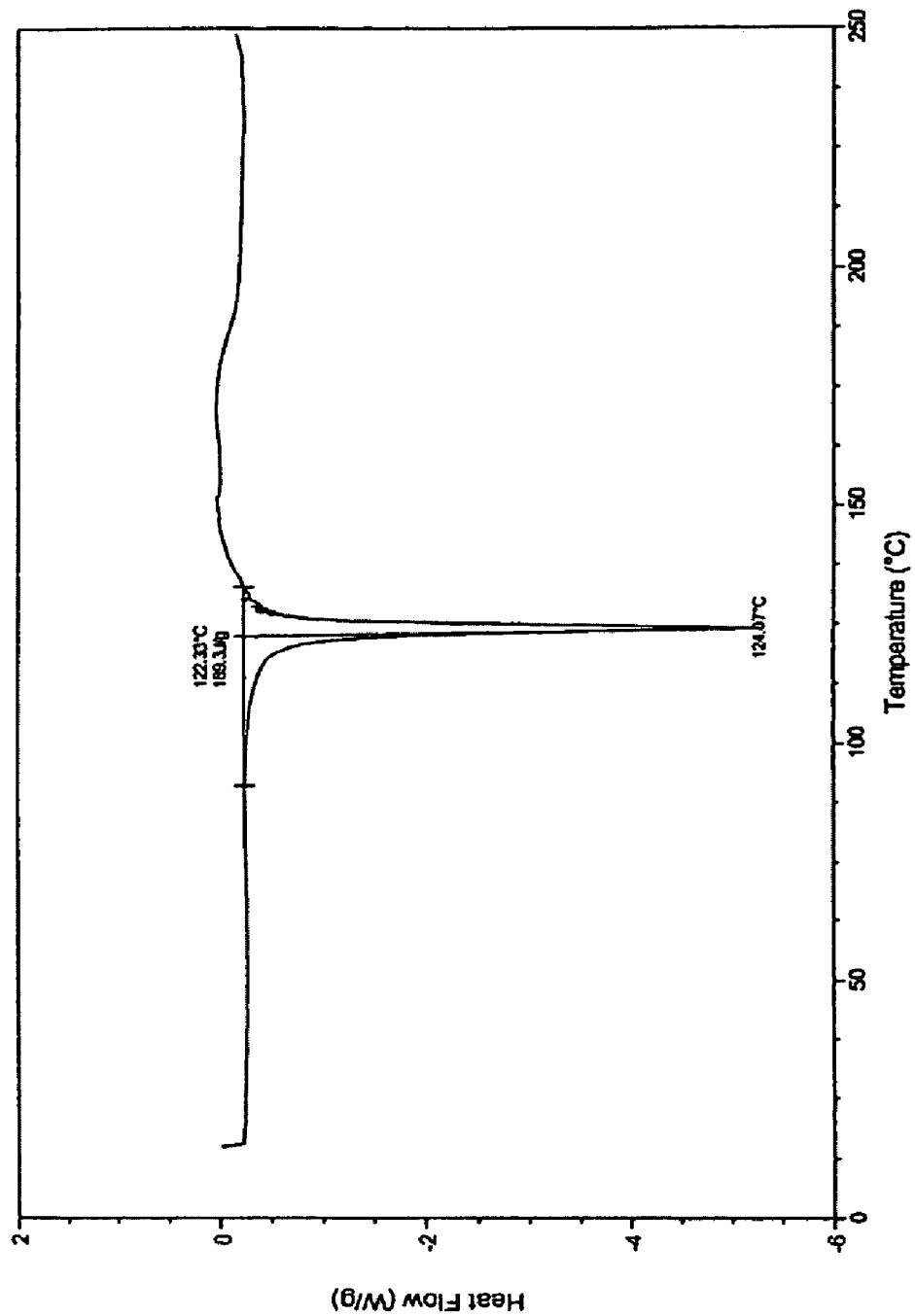
Figure 3. Differential Scanning Calorimetry (DSC) for N-[(1R)-5-tert-butyl-2,3-dihydro-1H-inden-1-yl]-N'-1H-indazol-4-ylurea hydrochloride (Example 13B)

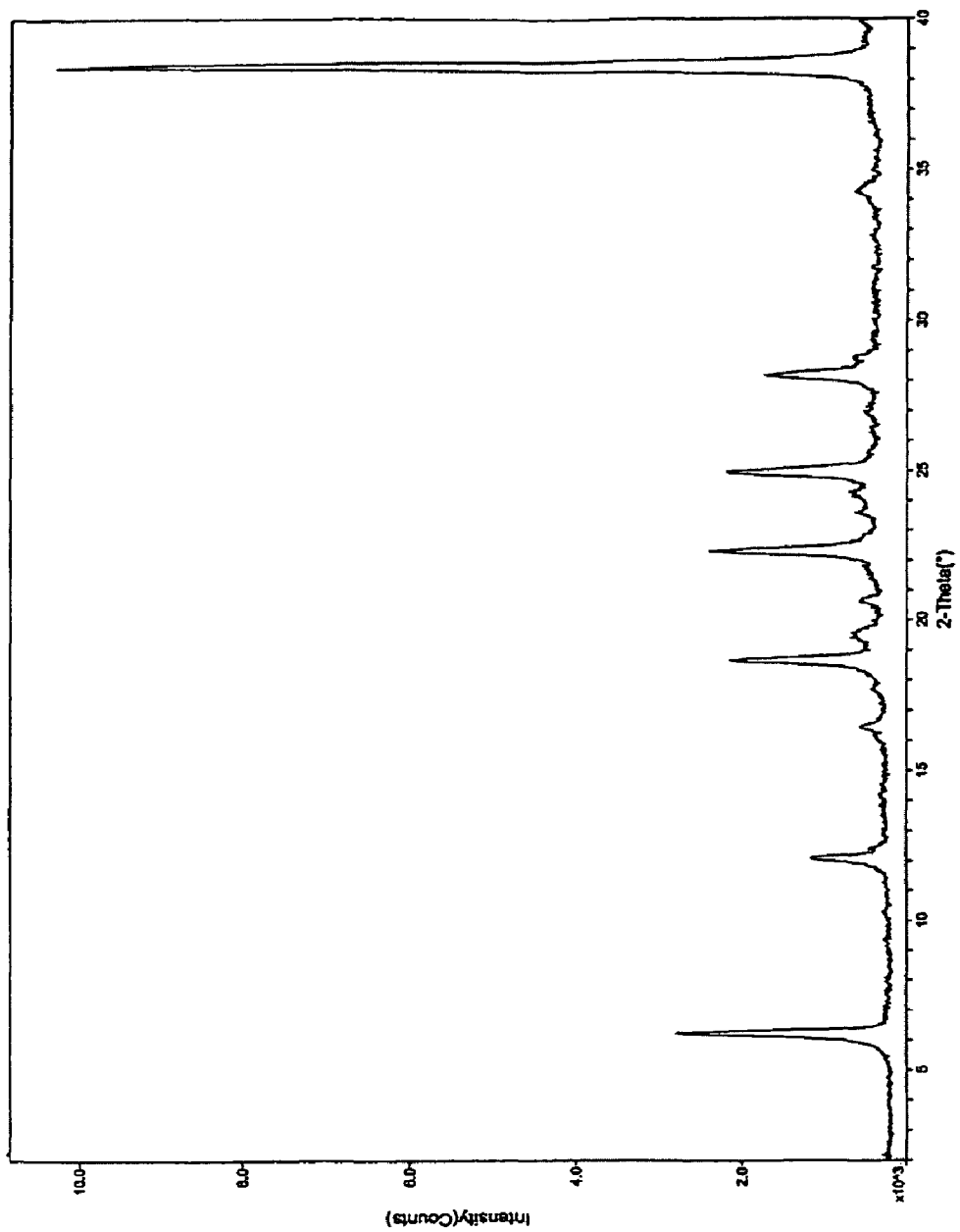
Figure 4. X-ray diffraction (XRD) for N-[(1R)-5-tert-butyl-2,3-dihydro-1H-inden-1-yl]-N'-1H-indazol-4-ylurea hydrochloride (Example 13B).

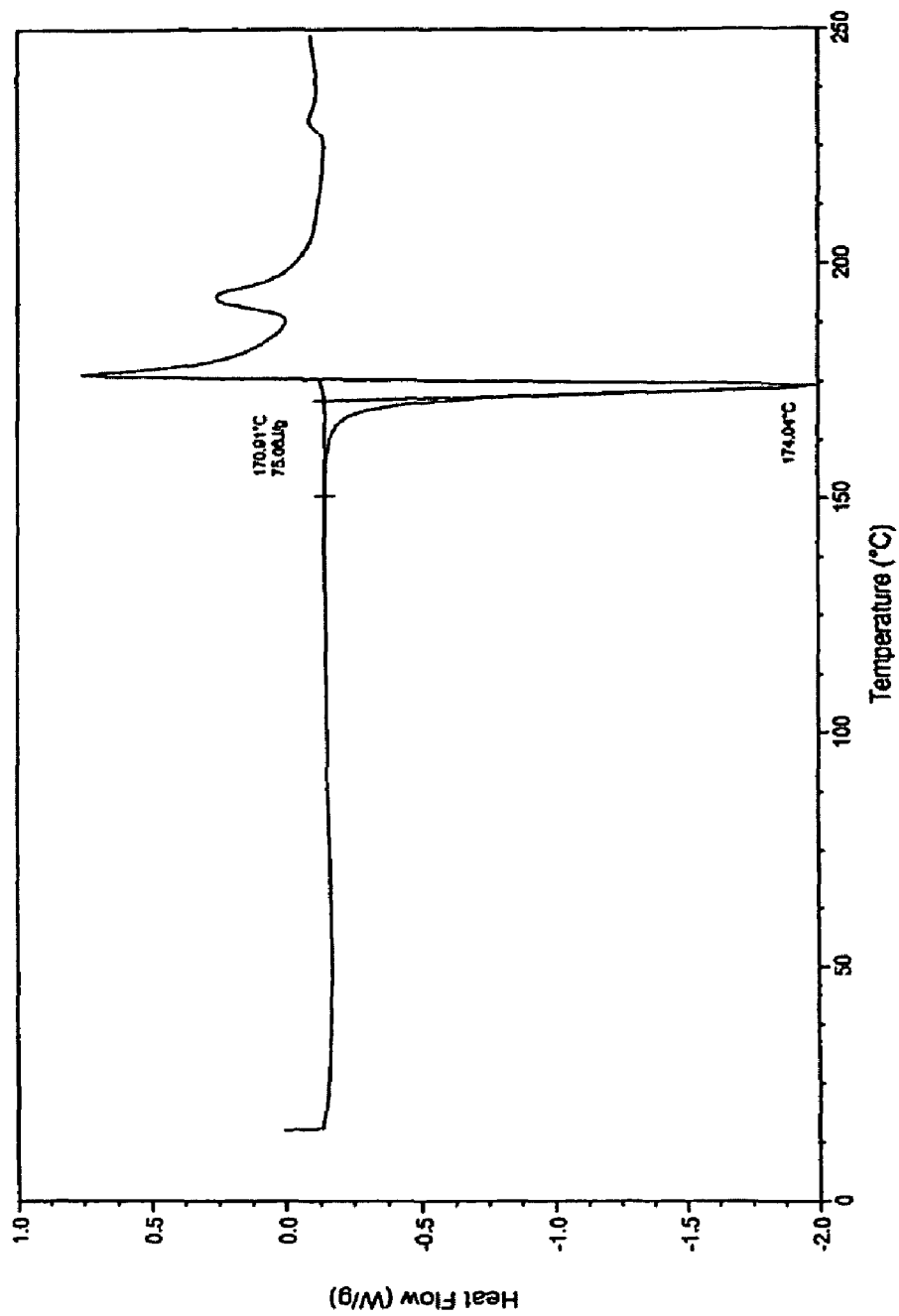
Figure 5. Differential Scanning Calorimetry (DSC) for N-[(1R)-5-tert-butyl-2,3-dihydro-1H-inden-1-yl]-N'-1H-indazol-4-ylurea tosylate (Example 13C)

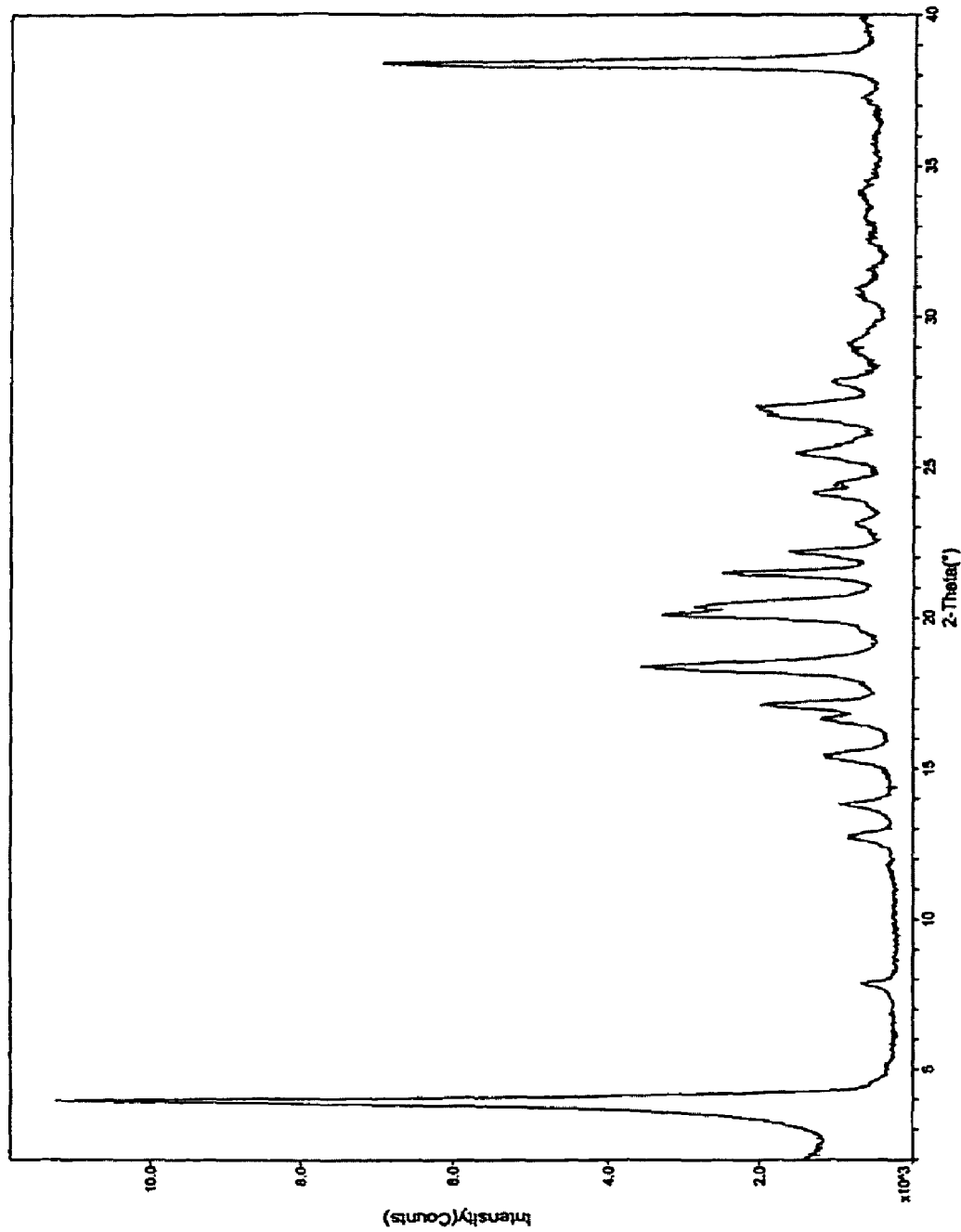
Figure 6. X-ray diffraction (XRD) for N-[(1R)-5-tert-butyl-2,3-dihydro-1H-inden-1-yl]-N'-1H-indazol-4-ylurea tosylate (Example 13C).

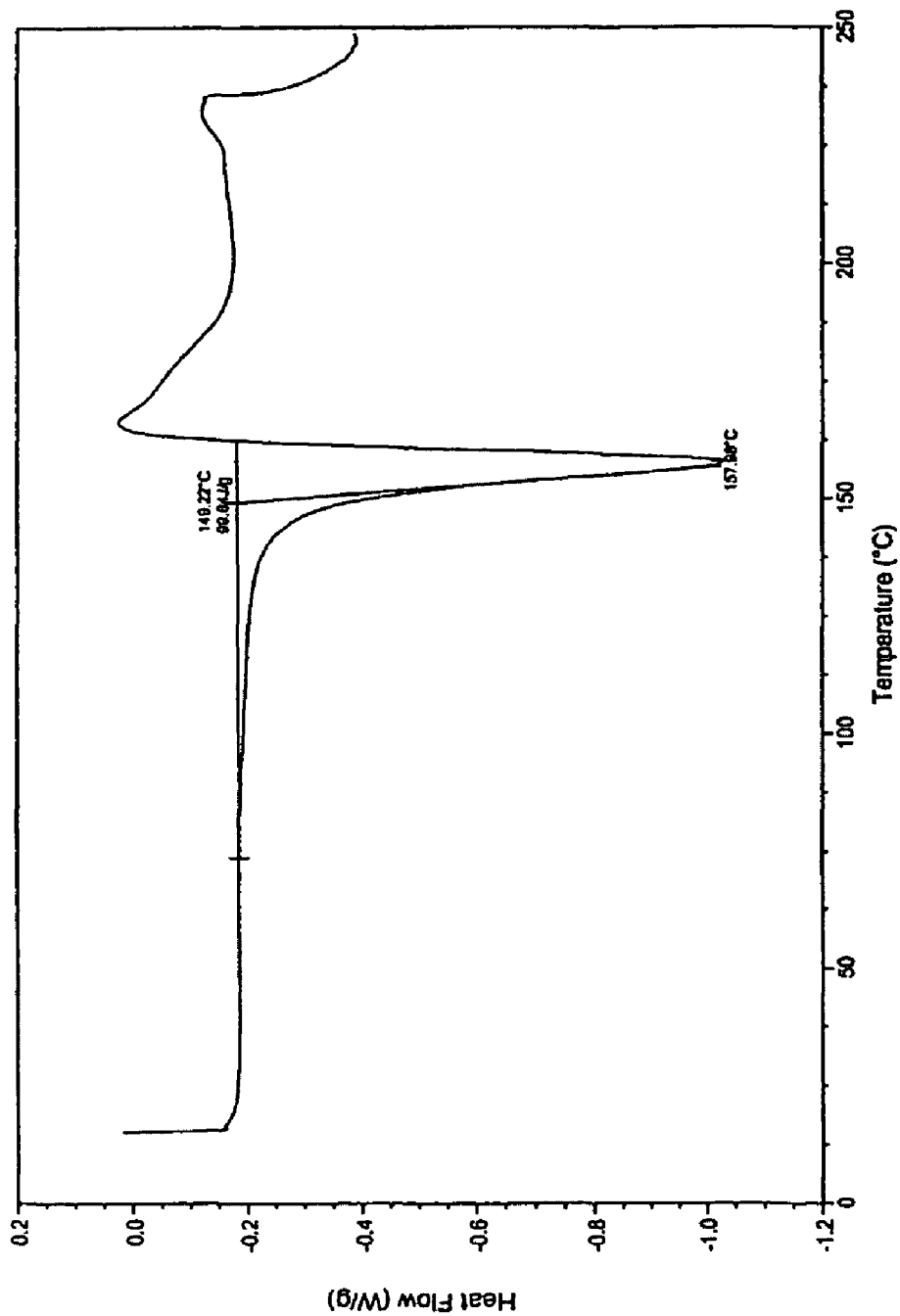
Figure 7. Differential Scanning Calorimetry (DSC) for N-[(1R)-5-tert-butyl-2,3-dihydro-1H-inden-1-yl]-N'-1H-indazol-4-ylurea benzenosulfonate (Example 13D)

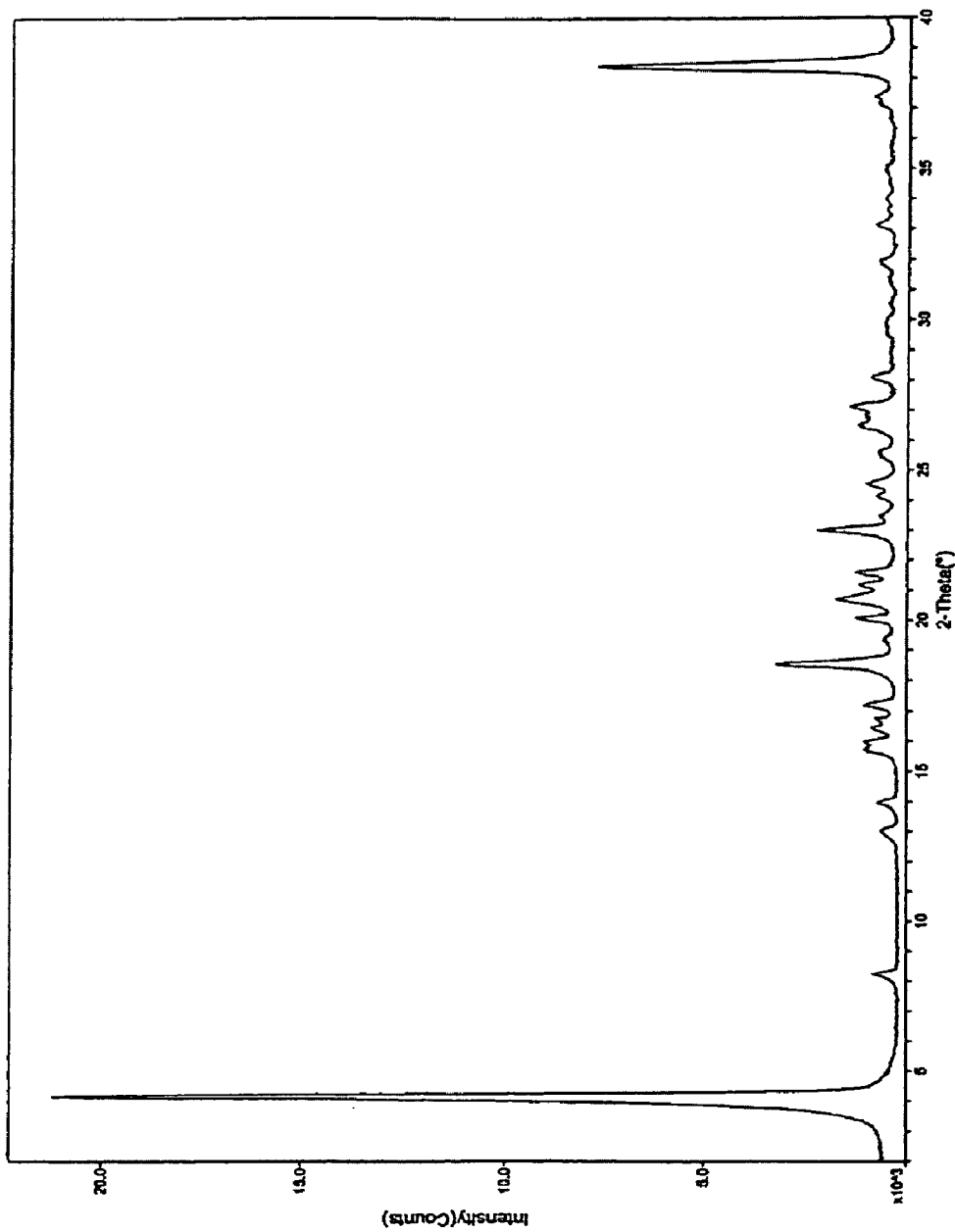
Figure 8. X-ray diffraction (XRD) for N-[(1R)-5-tert-butyl-2,3-dihydro-1H-inden-1-yl]-N'-1H-indazol-4-ylurea benzenosulfonate (Example 13D).

FUSED COMPOUNDS THAT INHIBIT VANILLOID RECEPTOR SUBTYPE 1 (VR1) RECEPTOR

This application is a divisional of U.S. application Ser. No. 10/864,068 filed on Jun. 9, 2004, now U.S. Pat. No. 7,375,126, which in turn seeks priority from U.S. Application 60/477,894, filed on Jun. 12, 2003, now expired. The application is also a Continuation-in-Part of U.S. application Ser. No. 11/258,980 filed on Oct. 26, 2005, now U.S. Pat. No. 8,026,256, which seeks priority from U.S. application Ser. No. 10/459,925 filed on Jun. 12, 2003, now issued U.S. Pat. No. 7,015,233, all of which are incorporated herein by reference in its entirety.

FIELD OF THE INVENTION

The present invention relates to compounds of formula (I), which are useful for treating disorders caused by or exacerbated by vanilloid receptor activity and pharmaceutical compositions containing compounds of formula (I). The compounds of the present invention are useful in treating pain, bladder overactivity, or urinary incontinence.

BACKGROUND OF INVENTION

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as VR1. The intradermal administration of capsaicin is characterized by an initial burning or hot sensation followed by a prolonged period of analgesia. The analgesic component of VR1 receptor activation is thought to be mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist can reduce inflammation-induced hyperalgesia in animal models. VR1 receptors are also localized on sensory afferents, which innervate the bladder. Capsaicin or resiniferatoxin has been shown to ameliorate incontinence symptoms upon injection into the bladder.

The VR1 receptor has been called a "polymodal detector" of noxious stimuli since it can be activated in several ways. The receptor channel is activated by capsaicin and other vanilloids and thus is classified as a ligand-gated ion channel. VR1 receptor activation by capsaicin can be blocked by the competitive VR1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the VR1 receptor (VR1(−/−)). Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The VR1 (−/−) mice also did not show reduced sensitivity to nerve injury-induced mechanical or thermal nociception. However, the VR1 knock-out mice were insensitive to the noxious effects of intradermal capsaicin, exposure to intense heat (50-55° C.), and failed to develop thermal hyperalgesia following the intradermal administration of carrageenan.

The compounds of the present invention are novel VR1 antagonists and have utility in treating pain, bladder overactivity, or urinary incontinence.

SUMMARY OF THE INVENTION

The present invention discloses novel compounds, a method for inhibiting the VR1 receptor in mammals using these compounds, a method for controlling pain in mammals, and pharmaceutical compositions including those compounds and a process for making those compounds. More particularly, the present invention is directed to compounds of formula (I)

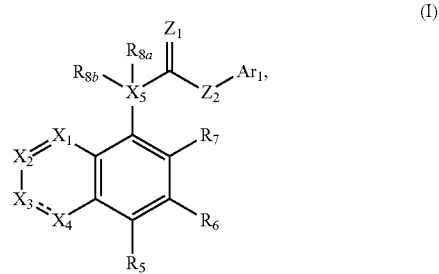

or a pharmaceutically acceptable salt or prodrug thereof, wherein
--- is absent or a single bond;
$X_1$ is N or $CR_1$;
$X_2$ is N or $CR_2$;
$X_3$ is N, $NR_3$, or $CR_3$;
$X_4$ is a bond, N, or $CR_4$;
$X_5$ is N or C;
provided that at least one of $X_1$, $X_2$, $X_3$, and $X_4$ is N;
$Z_1$ is O, NH, or S;
$Z_2$ is a bond, NH, or O;
$Ar_1$ is selected from the group consisting of

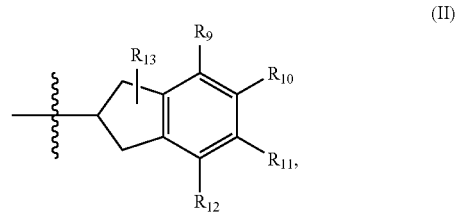

-continued

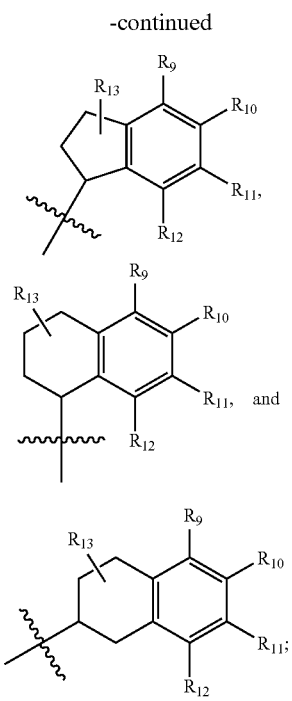

(III)

(V)

$R_1$, $R_3$, $R_5$, $R_6$, and $R_7$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C—$, $R_B(SO)_2R_AN—$, $R_AO(SO)_2—$, $R_BO(SO)_2—$, $Z_AZ_BN—$, $(Z_AZ_BN)$alkyl, $(Z_AZ_BN)$carbonyl, $(Z_AZ_BN)$carbonylalkyl, and $(Z_AZ_BN)$sulfonyl;

$R_2$ and $R_4$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C—$, $R_B(SO)_2R_AN—$, $R_AO(SO)_2—$, $R_BO(SO)_2—$, $Z_AZ_BN—$, $(Z_AZ_BN)$alkyl, $(Z_AZ_BN)$alkylcarbonyl, $(Z_AZ_BN)$carbonyl, $(Z_AZ_BN)$carbonylalkyl, $(Z_AZ_BN)$sulfonyl, $(Z_AZ_BN)C(=NH)—$, $(Z_AZ_BN)C(=NCN)NH—$ and $(Z_AZ_BN)C(=NH)NH—$;

$R_{8a}$ is hydrogen or alkyl;

$R_{8b}$ is absent, hydrogen, alkoxy, alkoxycarbonylalkyl, alkyl, alkylcarbonyloxy, alkylsulfonyloxy, halogen, or hydroxy;

$R_9$, $R_{10}$, $R_{11}$, and $R_{12}$ are each individually selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, aryl, carboxy, carboxyalkyl, cyano, cyanoalkyl, formyl, formylalkyl, haloalkoxy, haloalkyl, haloalkylthio, halogen, heteroaryl, heterocycle, hydroxy, hydroxyalkyl, mercapto, mercaptoalkyl, nitro, $(CF_3)_2(HO)C—$, $R_B(SO)_2R_AN—$, $R_AO(SO)_2—$, $R_BO(SO)_2—$, $Z_AZ_BN—$, $(Z_AZ_BN)$alkyl, $(Z_AZ_BN)$carbonyl, $(Z_AZ_BN)$carbonylalkyl, and $(Z_AZ_BN)$sulfonyl, wherein $Z_A$ and $Z_B$ are each independently hydrogen, alkyl, alkylcarbonyl, formyl, aryl, or arylalkyl, provided that at least one of $R_9$, $R_{10}$, $R_{11}$, or $R_{12}$ is other than hydrogen, or $R_{10}$ and $R_{11}$ taken together with the atoms to which they are attached form a cycloalkyl, cycloalkenyl or heterocycle ring;

$R_{13}$ is selected from the group consisting of hydrogen, alkyl, aryl, heteroaryl and halogen;

$R_A$ is hydrogen or alkyl; and $R_B$ is alkyl, aryl, or arylalkyl;

provided that $R_{8b}$ is absent when $X_5$ is N.

BRIEF DESCRIPTION OF FIGURES

The present invention will be further described with respect to the figures wherein:

FIG. 1 shows the results from the Differential Scanning Calorimetry (DSC) for the compound of Example 13A.

FIG. 2 shows the results from X-ray diffraction (XRD) for the compound of Example 13A.

FIG. 3 shows the results from DSC for the compound of Example 13B.

FIG. 4 shows the results from XRD for the compound of Example 13B.

FIG. 5 shows the results from DSC for the compound of Example 13C.

FIG. 6 shows the results from XRD for the compound of Example 13C.

FIG. 7 shows the results from DSC for the compound of Example 13D.

FIG. 8 shows the results from XRD for the compound of Example 13D.

DETAILED DESCRIPTION OF THE INVENTION (1) Embodiments

In the principal embodiment, compounds of formula (I) are disclosed

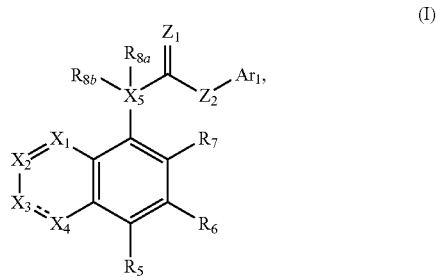

(I)

or a pharmaceutically acceptable salt or prodrug thereof, wherein

--- is absent or a single bond;

$X_1$ is N or $CR_1$;

$X_2$ is N or $CR_2$;

$X_3$ is N, $NR_3$, or $CR_3$;

$X_4$ is a bond, N, or $CR_4$;

$X_5$ is N or C;

provided that at least one of $X_1$, $X_2$, $X_3$, and $X_4$ is N;

$Z_1$ is O, NH, or S;
$Z_2$ is a bond, NH, or O;
$Ar_1$ is selected from the group consisting of

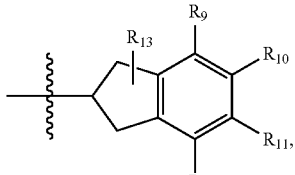
(II)

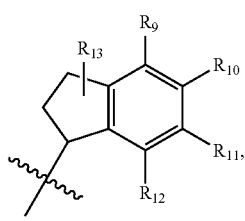
(III)

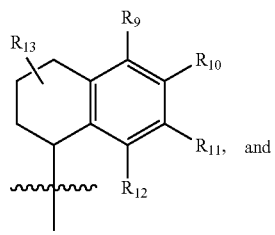
(IV)

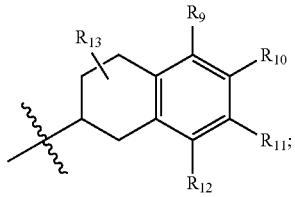
(V)

$R_1$, $R_3$, $R_5$, $R_6$, and $R_7$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C-$, $R_B(SO)_2R_AN-$, $R_AO(SO)_2-$, $R_BO(SO)_2-$, $Z_AZ_BN-$, $(Z_AZ_BN)$alkyl, $(Z_AZ_BN)$carbonyl, $(Z_AZ_BN)$carbonylalkyl, and $(Z_AZ_BN)$sulfonyl;

$R_2$ and $R_4$ are each independently selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, cycloalkyl, cycloalkylalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C-$, $R_B(SO)_2R_AN-$, $R_AO(SO)_2-$, $R_BO(SO)_2-$, $Z_AZ_BN-$, $(Z_AZ_BN)$alkyl, $(Z_AZ_BN)$alkylcarbonyl, $(Z_AZ_BN)$carbonyl, $(Z_AZ_BN)$carbonylalkyl, $(Z_AZ_BN)$sulfonyl, $(Z_AZ_BN)C(=NH)-$, $(Z_AZ_BN)C(=NCN)NH-$ and $(Z_AZ_BN)C(=NH)NH-$;

$R_{8a}$ is hydrogen or alkyl;

$R_{8b}$ is absent, hydrogen, alkoxy, alkoxycarbonylalkyl, alkyl, alkylcarbonyloxy, alkylsulfonyloxy, halogen, or hydroxy;

$R_9$, $R_{10}$, $R_{11}$, and $R_{12}$ are each individually selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, aryl, carboxy, carboxyalkyl, cyano, cyanoalkyl, formyl, formylalkyl, haloalkoxy, haloalkyl, haloalkylthio, halogen, heteroaryl, heterocycle, hydroxy, hydroxyalkyl, mercapto, mercaptoalkyl, nitro, $(CF_3)_2(HO)C-$, $R_B(SO)_2R_AN-$, $R_AO(SO)_2-$, $R_BO(SO)_2-$, $Z_AZ_BN-$, $(Z_AZ_BN)$alkyl, $(Z_AZ_BN)$carbonyl, $(Z_AZ_BN)$carbonylalkyl, and $(Z_AZ_BN)$sulfonyl, wherein $Z_A$ and $Z_B$ are each independently hydrogen, alkyl, alkylcarbonyl, formyl, aryl, or arylalkyl, provided that at least one of $R_9$, $R_{10}$, $R_{11}$, or $R_{12}$ is other than hydrogen, or $R_{10}$ and $R_{11}$ taken together with the atoms to which they are attached form a cycloalkyl, cycloalkenyl, or heterocycle ring;

$R_{13}$ is selected from the group consisting of hydrogen, alkyl, aryl, heteroaryl, and halogen;

$R_A$ is hydrogen or alkyl; and $R_B$ is alkyl, aryl, or arylalkyl;

provided that $R_{8b}$ is absent when $X_5$ is N.

In another embodiment of the present invention, compounds of formula (I) are disclosed wherein --- is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is selected from the group consisting of

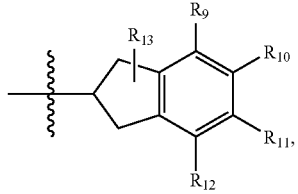
(II)

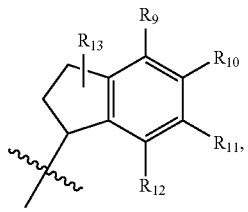
(III)

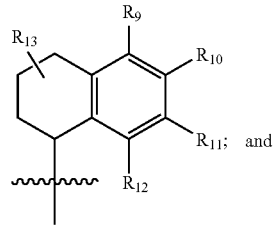
(IV)

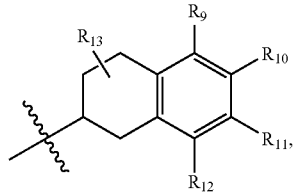
(V)

and $R_{8b}$ is absent; and $R_1$, $R_2$, $R_4$, $R_5$, $R_6$, $R_7$, $R_{8a}$, $R_9$, $R_{10}$, $R_{11}$, $R_{12}$ and $R_{13}$ are as defined in formula (I).

In another embodiment of the present invention, compounds of formula (I) are disclosed wherein --- is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is

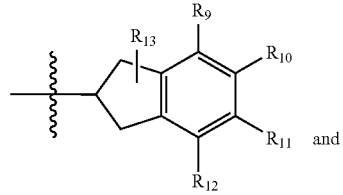

(II)

and

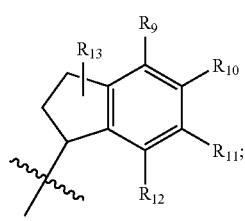

(III)

$R_1$, $R_4$, $R_5$, $R_6$, $R_7$, and $R_{8a}$ are hydrogen; $R_{8b}$ is absent; and $R_2$, $R_9$, $R_{10}$, $R_{11}$, $R_{12}$ and $R_{13}$ are as defined in formula (I).

In another embodiment of the present invention, compounds of formula (I) are disclosed wherein --- is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is

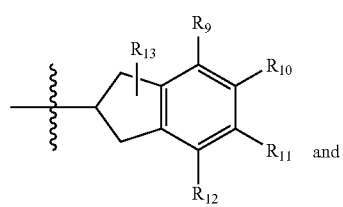

(II)

and

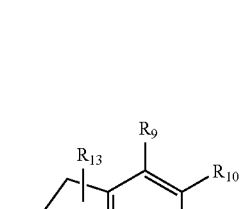

(III)

$R_1$, $R_4$, $R_5$, $R_6$, $R_7$, and $R_{8a}$ are hydrogen; at least one of $R_9$, $R_{10}$, $R_{11}$, and $R_{12}$ are independently selected from the group consisting of alkyl, alkoxy, alkoxyalkyl, aryl, cyanoalkyl, halogen, haloalkyl, haloalkoxy and heterocycle; $R_2$ is hydrogen or alkyl; and $R_{8b}$ is absent; and $R_2$ and $R_{13}$ are as defined in formula (I).

In another embodiment of the present invention, compounds of formula (I) are disclosed wherein --- is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is

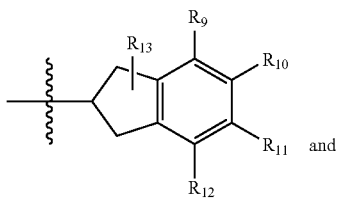

(II)

and

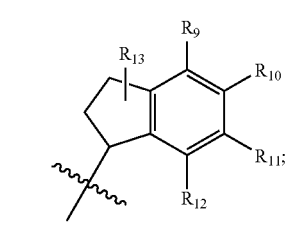

(III)

$R_1$, $R_4$, $R_5$, $R_6$, $R_7$, and $R_{8a}$ are hydrogen; at least one of $R_9$, $R_{10}$, $R_{11}$, and $R_{12}$ are independently selected from the group consisting of alkyl, halogen and haloalkyl; $R_2$ is hydrogen or alkyl; $R_{8b}$ is absent; and $R_2$ and $R_{13}$ are as defined in formula (I).

In another embodiment of the present invention, compounds of formula (I) are disclosed wherein --- is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is

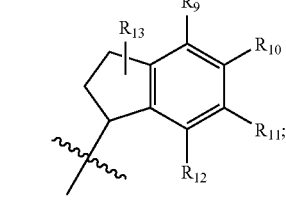

(IV)

and

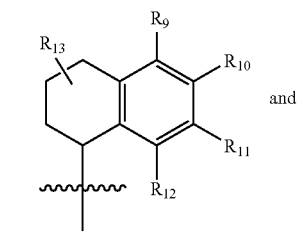

(V)

$R_1$, $R_4$, $R_5$, $R_6$, $R_7$, and $R_{8a}$ are hydrogen; $R_{8b}$ is absent; and $R_2$ and $R_{13}$ are as defined in formula (I).

In another embodiment of the present invention, compounds of formula (I) are disclosed wherein --- is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is

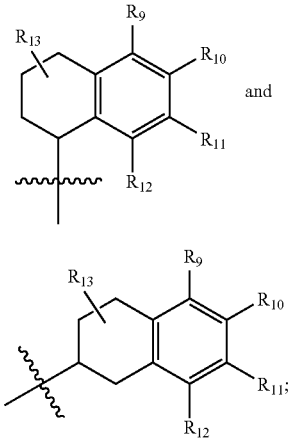

$R_1$, $R_4$, $R_5$, $R_6$, $R_7$, and $R_{8a}$ are hydrogen; at least one of $R_9$, $R_{10}$, $R_{11}$, and $R_{12}$ are independently selected from the group consisting of alkyl, alkoxy, alkoxyalkyl, aryl, cyanoalkyl, halogen, haloalkyl, haloalkoxy and heterocycle; $R_2$ is hydrogen or alkyl;

$R_{8b}$ is absent; and $R_{13}$ is as defined in formula (I).

In another embodiment of the present invention, compounds of formula (I) are disclosed wherein --- is a single bond; $X_1$ is $CR_1$; $X_2$ is $CR_2$; $X_4$ is $CR_4$; $X_3$ and $X_5$ are N; $Z_1$ is O; $Z_2$ is NH; $Ar_1$ is

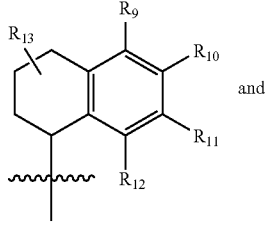

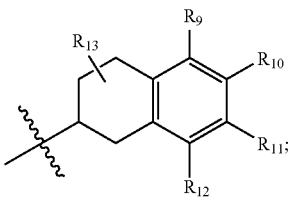

$R_1$, $R_4$, $R_5$, $R_6$, $R_7$, and $R_{8a}$ are hydrogen; at least one of $R_9$, $R_{10}$, $R_{11}$, and $R_{12}$ are independently selected from the group consisting of alkyl, halogen and haloalkyl; $R_2$ is hydrogen or alkyl; $R_{8b}$ is absent; and $R_{13}$ are as defined in formula (I).

In another embodiment of the present invention, compounds of formula (I) are disclosed wherein --- is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is selected from the group consisting of

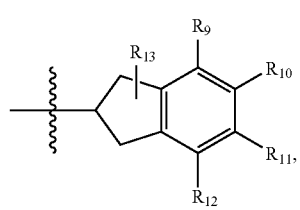

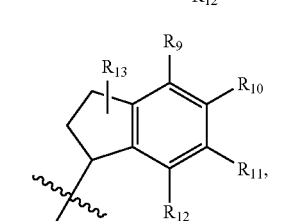

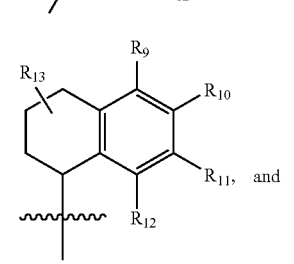

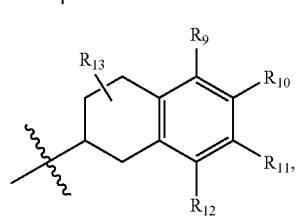

$R_{8b}$ is absent; and $R_1$, $R_3$, $R_5$, $R_6$, $R_7$, $R_{8a}$, $R_9$, $R_{10}$, $R_{11}$, $R_{12}$ and $R_{13}$ are as defined in formula (I).

In another embodiment of the present invention, compounds of formula (I) are disclosed wherein --- is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is selected from the group consisting of

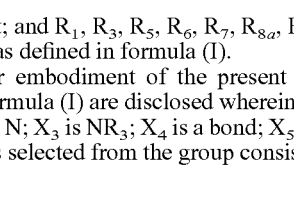

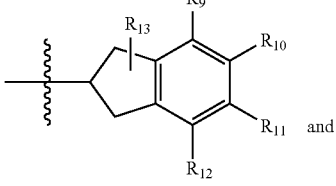

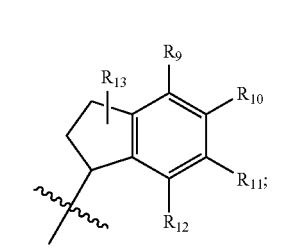

$R_1$ is selected from the group consisting of hydrogen, alkyl, halogen, and hydroxyalkyl; $R_3$, $R_5$, $R_6$, $R_7$, and $R_{8a}$ are hydrogen; $R_{8b}$ is absent; and $R_9$, $R_{10}$, $R_{11}$, $R_{12}$ and $R_{13}$ are as defined in formula (I).

In another embodiment of the present invention, compounds of formula (I) are disclosed wherein --- is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is selected from the group consisting of

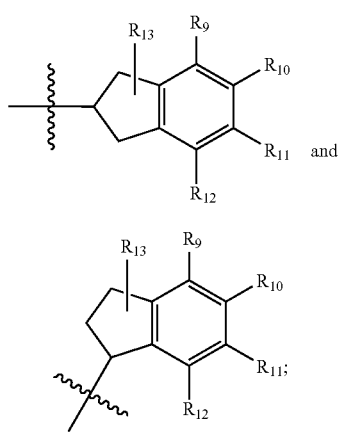

$R_1$ is selected from the group consisting of hydrogen, alkyl and hydroxyalkyl; $R_3$, $R_5$, $R_6$, $R_7$, and $R_{8a}$ are hydrogen; at least one of $R_9$, $R_{10}$, $R_{11}$, and $R_{12}$ are independently selected from the group consisting of alkyl, alkoxy, alkoxyalkyl, aryl, cyanoalkyl, halogen, haloalkyl, haloalkoxy and heterocycle; $R_{8b}$ is absent; and $R_{13}$ is as defined in formula (I).

In another embodiment of the present invention, compounds of formula (I) are disclosed wherein --- is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is selected from the group consisting of

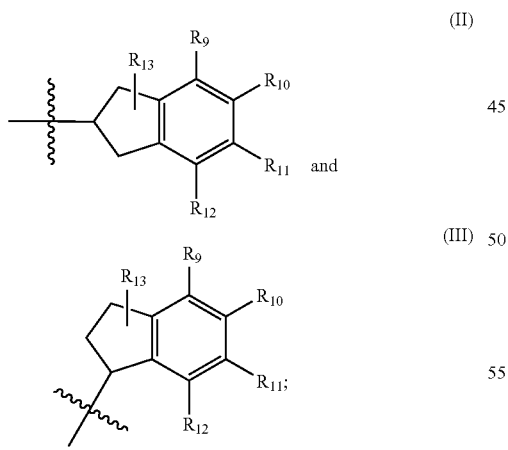

$R_1$ is selected from the group consisting of hydrogen, alkyl and hydroxyalkyl; $R_3$, $R_5$, $R_6$, $R_7$, and $R_{8a}$ are hydrogen; at least one of $R_9$, $R_{10}$, $R_{11}$, and $R_{12}$ are independently selected from the group consisting of alkyl, alkoxy, alkoxyalkyl, cyanoalkyl, halogen, haloalkyl, and haloalkoxy; $R_{8b}$ is absent; and $R_{13}$ is as defined in formula (I).

In another embodiment of the present invention, the amorphous form of compounds of formula (I) are disclosed herein.

In another embodiment of the present invention, salt forms of compounds of formula (I) are disclosed herein.

In another embodiment of the present invention, compounds of formula (I) are disclosed wherein --- is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is selected from the group consisting of

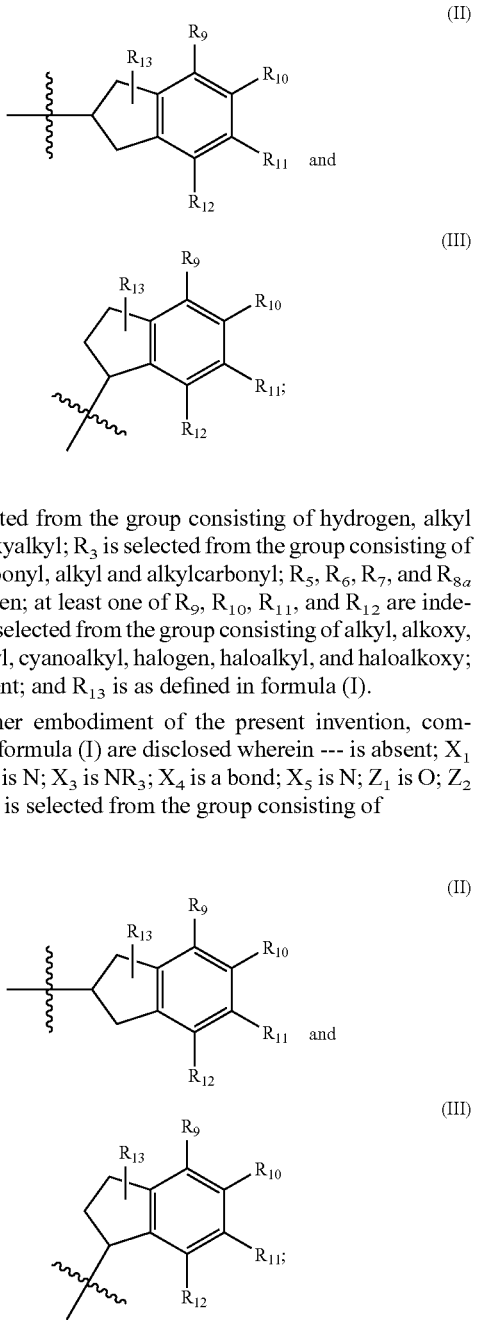

$R_1$ is selected from the group consisting of hydrogen, alkyl and hydroxyalkyl; $R_3$ is selected from the group consisting of alkoxycarbonyl, alkyl and alkylcarbonyl; $R_5$, $R_6$, $R_7$, and $R_{8a}$ are hydrogen; at least one of $R_9$, $R_{10}$, $R_{11}$, and $R_{12}$ are independently selected from the group consisting of alkyl, alkoxy, alkoxyalkyl, cyanoalkyl, halogen, haloalkyl, and haloalkoxy; $R_{8b}$ is absent; and $R_{13}$ is as defined in formula (I).

In another embodiment of the present invention, compounds of formula (I) are disclosed wherein --- is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is selected from the group consisting of $R_1$ is selected from the group consisting of hydrogen, alkyl and hydroxyalkyl; $R_3$, $R_5$, $R_6$, $R_7$, and $R_{8a}$ are hydrogen; at least one of $R_9$, $R_{10}$, $R_{11}$, and $R_{12}$ is heterocycle; and $R_{8b}$ is absent; and $R_{13}$ is as defined in formula (I).

In another embodiment of the present invention, compounds of formula (I) are disclosed wherein --- is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is selected from the group consisting of

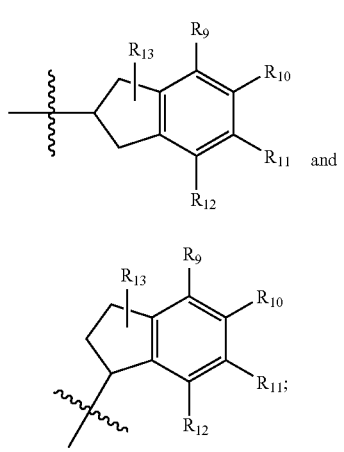

$R_1$ is selected from the group consisting of hydrogen, alkyl and hydroxyalkyl; $R_3$, $R_5$, $R_6$, $R_7$, and $R_{8a}$ are hydrogen; at least one of $R_9$, $R_{10}$, $R_{11}$, and $R_{12}$ is selected from the group consisting of azabicyclooctyl, azabicycloheptyl, isoquinolinyl, morpholinyl, oxazepanyl, piperidinyl, pyridinyl, pyrrolidinyl, piperazinyl or hexahydro-1H-azepinyl; $R_{8b}$ is absent; and $R_{13}$ is as defined in formula (I).

In another embodiment of the present invention, compounds of formula (I) are disclosed wherein --- is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is selected from the group consisting of

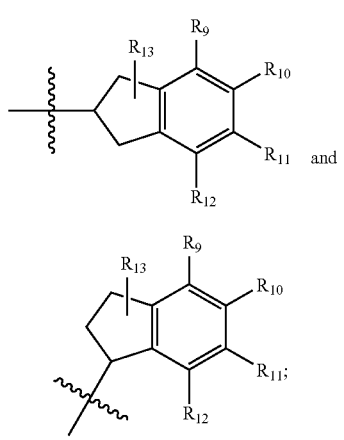

$R_1$ is selected from the group consisting of hydrogen, alkyl and hydroxyalkyl; $R_3$ is selected from the group consisting of alkoxycarbonyl and alkylcarbonyl; $R_5$, $R_6$, $R_7$, and $R_{8a}$ are hydrogen; at least one of $R_9$, $R_{10}$, $R_{11}$, and $R_{12}$ is selected from the group consisting of azabicyclooctyl, azabicycloheptyl, isoquinolinyl, morpholinyl, oxazepanyl, piperidinyl, pyridinyl, pyrrolidinyl, piperazinyl or hexahydro-1H-azepinyl; $R_{8b}$ is absent; and $R_{13}$ is as defined in formula (I).

In another embodiment of the present invention, compounds of formula (I) are disclosed wherein --- is absent; $X_1$ is $CR_1$; $X_2$ is N; $X_3$ is $NR_3$; $X_4$ is a bond; $X_5$ is N; $Z_1$ is O; $Z_2$ is NH; $Ar_1$ is selected from the group consisting of

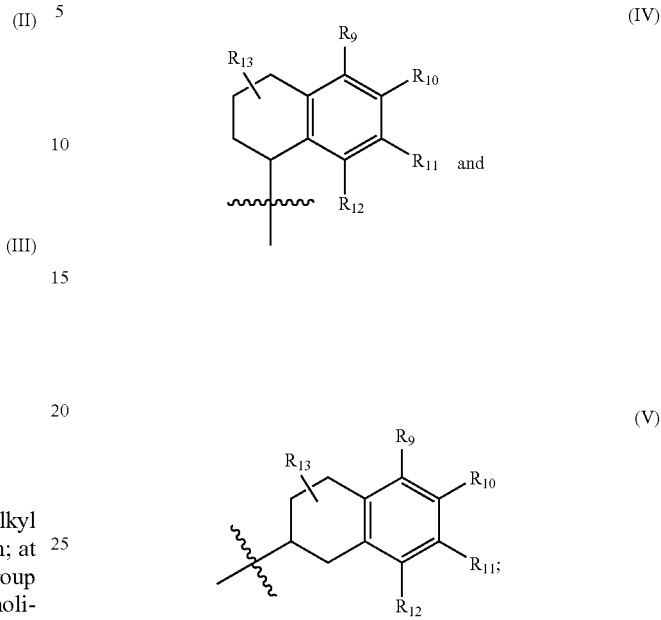

$R_1$ is selected from the group consisting of hydrogen, alkyl and hydroxyalkyl; $R_3$, $R_5$, $R_6$, $R_7$, and $R_{8a}$ are hydrogen; at least one of $R_9$, $R_{10}$, $R_{11}$, and $R_{12}$ are independently selected from the group consisting of alkyl, alkoxy, alkoxyalkyl, cyanoalkyl, halogen, haloalkyl, haloalkoxy and heterocycle; $R_{8b}$ is absent; and $R_{13}$ is as defined in formula (I).

Another embodiment of the present invention is related to a method of treating a disorder by inhibiting vanilloid receptor subtype 1 in a mammal comprising administering a therapeutically effective amount of a compound of formula (I) or a pharmaceutically acceptable salt or prodrug thereof.

Another embodiment of the present invention is related to a method of treating a pain by inhibiting vanilloid receptor subtype 1 in a mammal comprising administering a therapeutically effective amount of a compound of formula (I) or a pharmaceutically acceptable salt or prodrug thereof.

Another embodiment of the present invention is related to a method of treating a bladder overactivity by inhibiting vanilloid receptor subtype 1 in a mammal comprising administering a therapeutically effective amount of a compound of formula (I) or a pharmaceutically acceptable salt or prodrug thereof.

Another embodiment of the present invention is related to a method of treating a urinary incontinence by inhibiting vanilloid receptor subtype 1 in a mammal comprising administering a therapeutically effective amount of a compound of formula (I) or a pharmaceutically acceptable salt or prodrug thereof.

Another embodiment of the present invention is related to a method of treating a inflammatory thermal hyperalgesia by inhibiting vanilloid receptor subtype 1 in a mammal comprising administering a therapeutically effective amount of a compound of formula (I) or a pharmaceutically acceptable salt or prodrug thereof.

Another embodiment of the present invention is related to a process for preparing a compound having structural formula (VI), (VI)

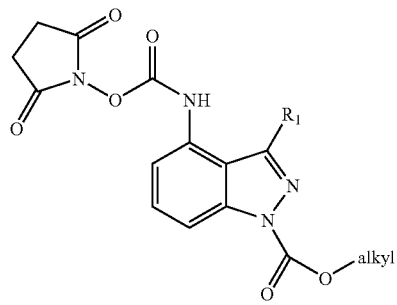

wherein, $R_1$ is hydrogen or alkyl, comprising, in toto, the steps of: (a) treating a 2-alkyl substituted 3-nitro-aniline (VIa) in acetic acid with sodium nitrite to provide a compound of formula (VIb)

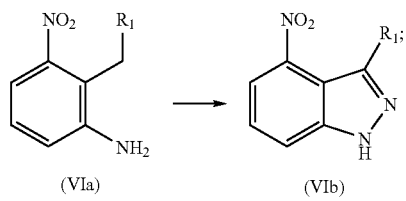

(b) treating a compound of formula (VIb) with an alkyl chloroformate and a base to provide a compound of formula (VIc)

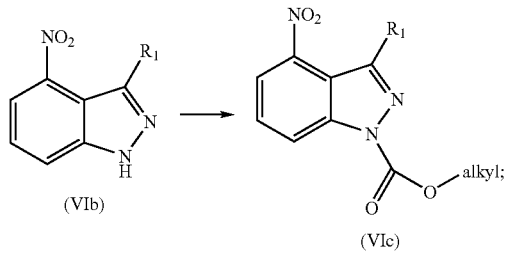

(c) treating a compound of formula (VIc) with an atmosphere of hydrogen in the presence of palladium on carbon in a solvent such as but not limited to methanol to provide a compound of formula (VId)

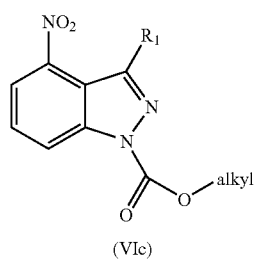

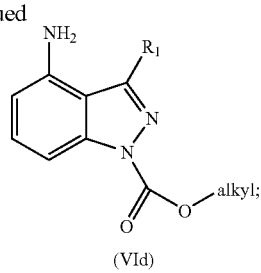

(VId)

(d) treating a compound of formula (VId) with a compound of formula (VIe) in a solvent such as but not limited to acetonitrile to provide a compound of formula (VI)

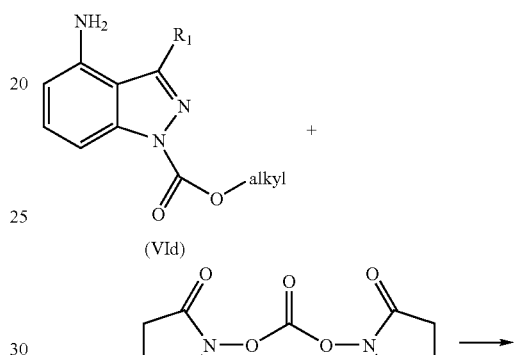

(VI)

Another embodiment of the present invention is related to a process for preparing a compound having structural formula (VI) using methyl chloroformate and a base such as but not limited to 1,8-diazabicyclo[5.4.0]undec-7-ene in step (b), followed by step (c) and (d) to provide the compound of formula (VI).

Another embodiment of the present invention there is disclosed a process for preparing a compound having structural formula (VII), (VII)

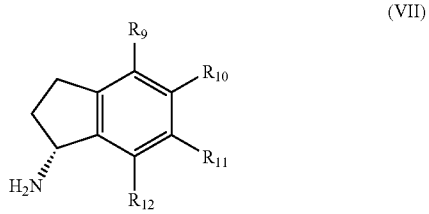

wherein, as $R_9$, $R_{10}$, $R_{11}$ and $R_{12}$ are as defined in formula (I), comprising, in toto, the steps of: (a) treating 3-chloropropionyl chloride with aluminum trichloride in dichloromethane followed by addition of a substituted benzene (VIIa), wherein $R_9$, $R_{10}$, $R_{11}$ and $R_{12}$ are as defined in formula (I) to provide a compound of formula (VIIb)

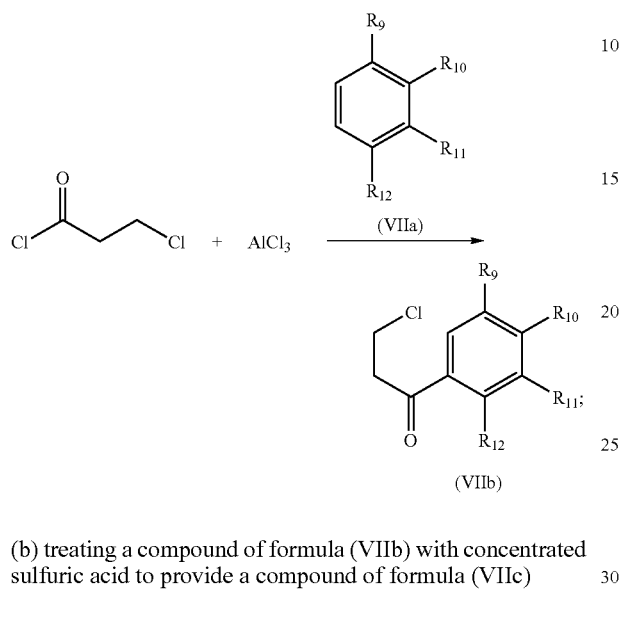

(b) treating a compound of formula (VIIb) with concentrated sulfuric acid to provide a compound of formula (VIIc)

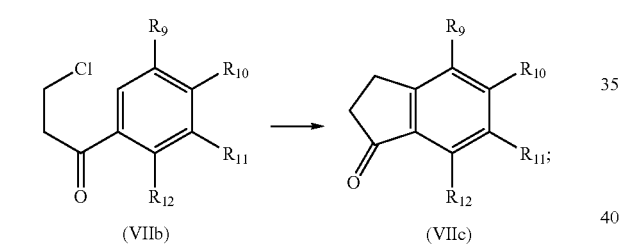

(c) heating a compound of formula (VIIc) and a compound of formula (VIId) in the presence of or absence of an acid such as but not limited to trifluoroacetic acid or p-toluene sulfonic acid in toluene or a similar solvent in a flask fitted with a Dean-Stark trap until an approximately equimolar quantity of water based on the starting material has been collected, followed by adding the mixture to a solution of sodium borohydride in ethanol at a temperature less than or about 0° C., followed by stirring for about 3 hours or more until there is a consumption of compound of formula (VIIc), followed by the slow addition of water, followed by extraction with ethyl acetate to provide the compound of formula (VIIe) which is optionally purified before use in step (d)

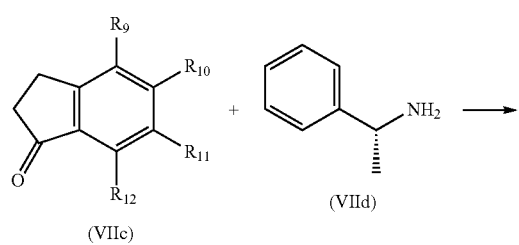

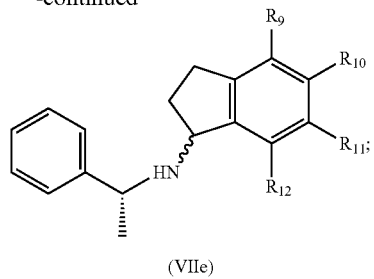

(d) treating a compound of formula (VIIe) with an atmosphere of hydrogen at about 40 psi in the presence of about 5-20% palladium on carbon in a solvent with an acid to provide a compound of formula (VII) which is optionally purified

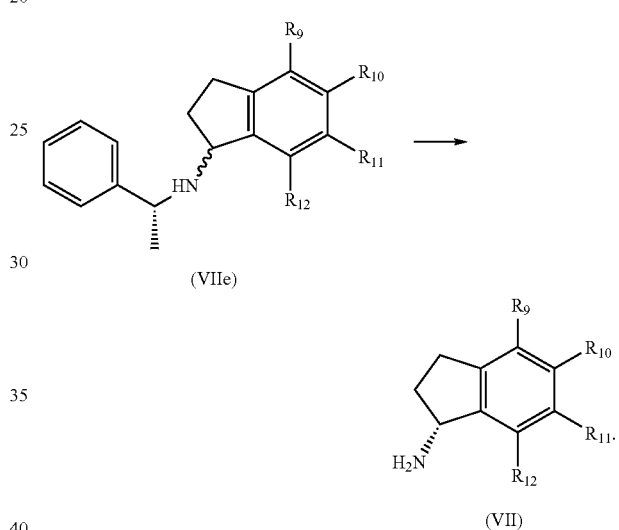

In another embodiment of the present invention, the substitution of an atmosphere of hydrogen in the presence of palladium or platinum on carbon in a solvent such as but not limited to methanol for sodium borohydride in ethanol in step (c), followed by step (d), will provide the compound of formula (VII).

In another embodiment of the present invention, the process for preparing a compound having structural formula (VII) contemplates the use of methanol as a solvent in step (d) to provide the compound of formula (VII).

In another embodiment of the present invention, the process for preparing a compound having structural formula (VII) contemplates the use of solvents including aqueous methanol containing 1% acetic acid in step (d) to provide the compound of formula (VII).

In another embodiment of the present invention, the process for preparing a compound having structural formula (VII) contemplates the use of methanol containing 6% acetic acid in step (d) to provide the compound of formula (VII).

In another embodiment of the present invention, there is disclosed a process of preparing compounds of formula (VII), wherein the compound of formula (VIIe) is further purified by preparing the salt with an acid and recrystallized prior to step (d).

In another embodiment of the present invention, there is disclosed a process of preparing compounds of formula (VII), wherein the compound of formula (VIIe) is further purified by preparing the tosylate salt and recrystallized prior to step (d).

In another embodiment of the present invention, there is disclosed a process of preparing compounds of formula (VII), wherein the compound of formula (VII) is further purified by preparing the salt with an acid and recrystallized.

In another embodiment of the present invention, there is disclosed a process of preparing compounds of formula (VII), wherein the compound of formula (VII) is further purified by preparing the tosylate salt and recrystallized.

In another embodiment of the present invention there is disclosed a process for preparing a compound having structural formula (VIII),

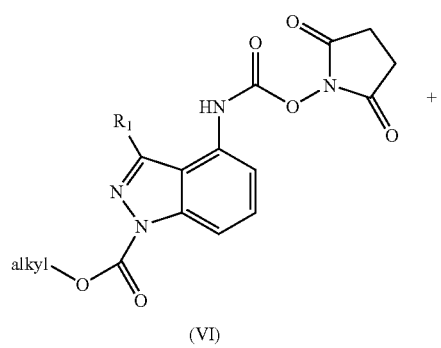

(VIII)

wherein, $R_1$ is hydrogen or alkyl and $R_9$, $R_{10}$, $R_{11}$ and $R_{12}$ are as defined in formula (I), comprising, in toto, the steps of: (a) treating a compound of formula (VI) with a compound of formula (VII) to provide a compound of formula (VIIIa)

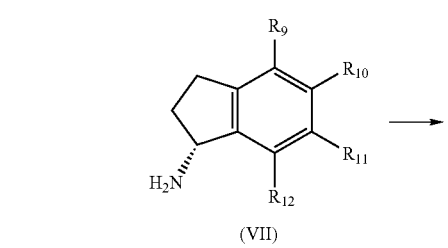

(VI)

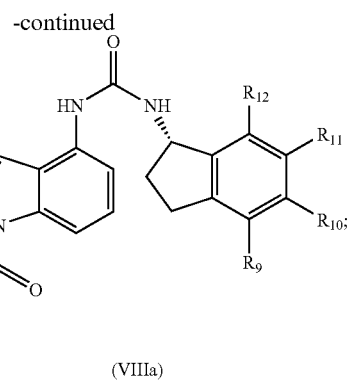

(VIIIa)

(b) treating a compound of formula (VIIIa) with sodium hydroxide or potassium hydroxide in methanol to provide the compound of formula (VIII)

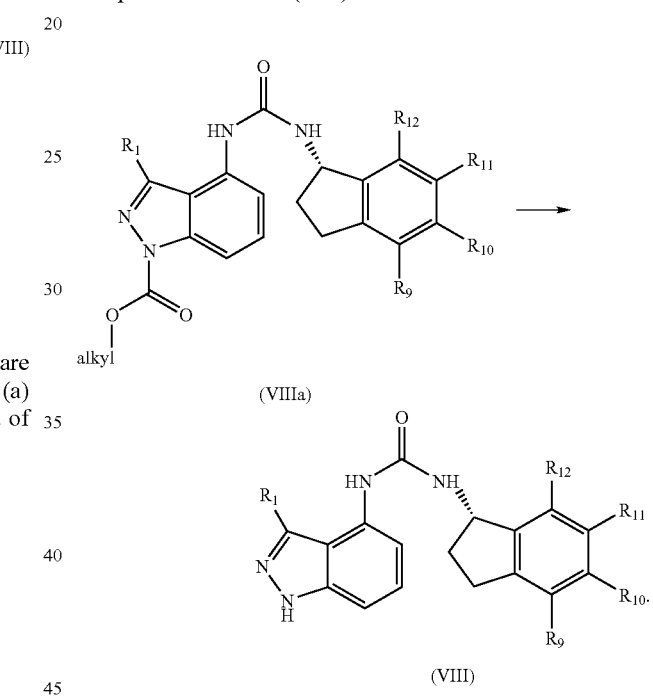

In another embodiment of the present invention there is disclosed the use of a compound of formula (VI) in the process of preparing a compound of formula (VIII) which is representative of compound of formula (I).

In another embodiment of the present invention there is disclosed the use of a compound of formula (VI) in the process of preparing a compound of formula (VIII) which is representative of compound of formula (I), which is useful for the treatment of a disorder by inhibiting vanilloid receptor subtype 1 in a mammal comprising administering a therapeutically effective amount of a compound of formula (I) or a pharmaceutically acceptable salt or prodrug thereof.

In another embodiment of the present invention there is disclosed the use of a compound of formula (VI) in the process of preparing a compound of formula (VIII) which is representative of compound of formula (I), which is useful for the treatment of pain in a mammal comprising administering a therapeutically effective amount of a compound of formula (I) or a pharmaceutically acceptable salt or prodrug thereof.

In another embodiment of the present invention there is disclosed the use of a compound of formula (VII) in the process of preparing a compound of formula (VIII) which is representative of compound of formula (I).

In another embodiment of the present invention there is disclosed the use of a compound of formula (VII) in the process of preparing a compound of formula (VIII) which is representative of compound of formula (I), which is useful for the treatment of a disorder by inhibiting vanilloid receptor subtype 1 in a mammal comprising administering a therapeutically effective amount of a compound of formula (I) or a pharmaceutically acceptable salt or prodrug thereof.

In another embodiment of the present invention there is disclosed the use of a compound of formula (VII) in the process of preparing a compound of formula (VIII) which is representative of compound of formula (I), which is useful for the treatment of pain in a mammal comprising administering a therapeutically effective amount of a compound of formula (I) or a pharmaceutically acceptable salt or prodrug thereof.

Another embodiment of the present invention relates to a process for preparing a compound having structural formula (IX),

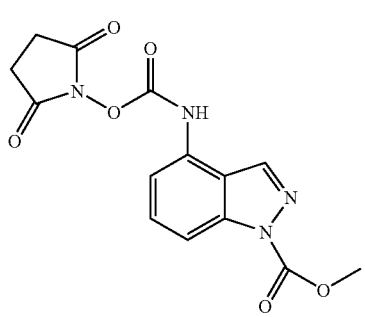

(IX)

comprising, in toto, the steps of: (a) treating 2-methyl 3-nitro-analine (IXa) of in acetic acid with sodium nitrite to provide a compound of formula (IXb)

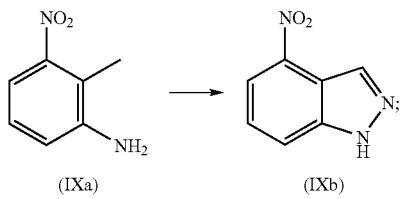

(b) treating a compound of formula (IXb) with methyl chloroformate and a base such as but not limited to 1,8-diazabicyclo[5.4.0]undec-7-ene to provide a compound of formula (IXc)

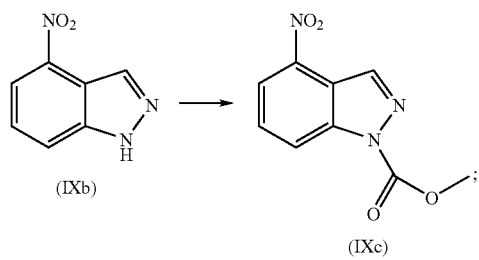

(c) treating a compound of formula (IXc) with an atmosphere of hydrogen in the presence of palladium on carbon in a solvent such as methanol to provide a compound of formula (IXd)

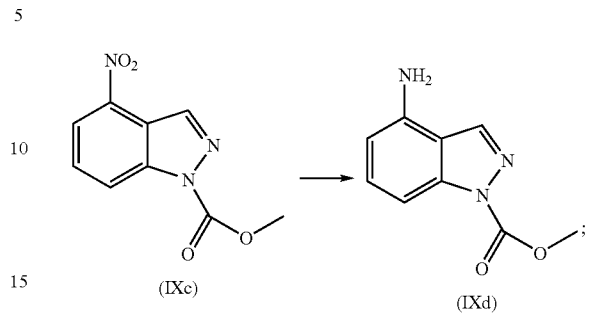

(d) treating a compound of formula (IXd) with a compound of formula (IXe) in a solvent such as but no limited to acetonitrile to provide a compound of formula (IX)

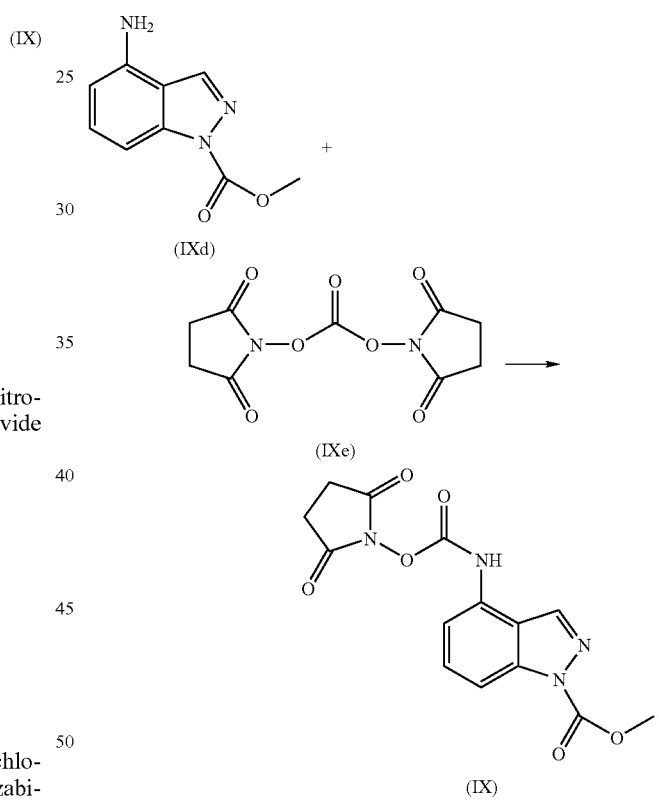

Another embodiment of the present invention related to a process for preparing a compound having structural formula (X),

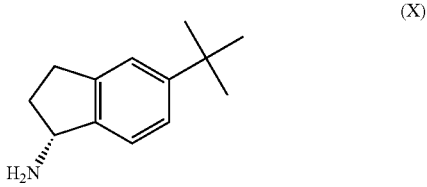

(X)

comprising, in toto, the steps of: (a) treating 3-chloropropionyl chloride with aluminum trichloride in dichloromethane followed by addition of a tert-butyl benzene (Xa), to provide a compound of formula (Xb)

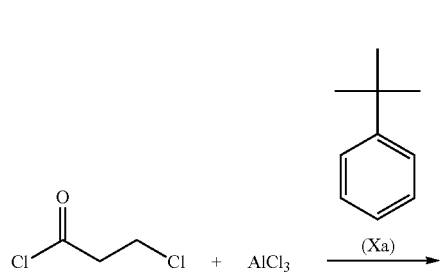

(b) treating a compound of formula (Xb) with concentrated sulfuric acid to provide a compound of formula (Xc)

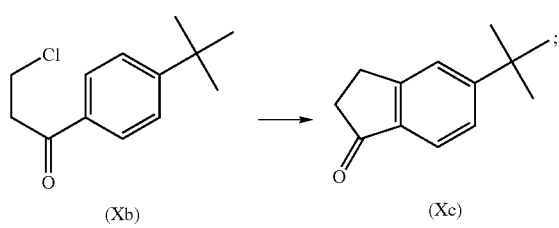

(c) heating a compound of formula (Xc) and a compound of formula (Xd) in the presence of or absence of an acid such as but not limited to trifluoroacetic acid or p-toluenesulfonic acid in toluene in a flask fitted with a Dean-Stark trap followed by adding the mixture to a solution of sodium borohydride in ethanol at a temperature of about 0° C., followed by stirring, followed by the slow addition of water, followed by extraction with ethyl acetate to provide the compound of formula (Xe) which is optionally purified before use in step (d)

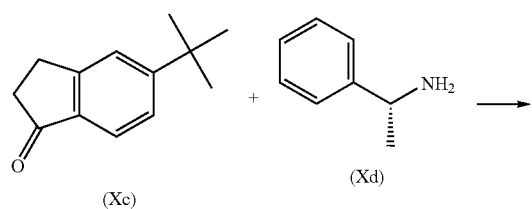

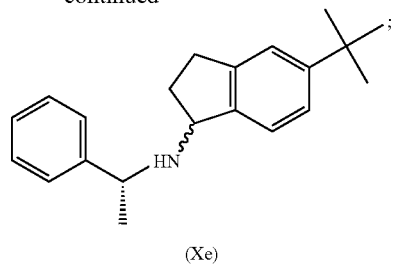

(d) treating a compound of formula (Xe) with an atmosphere of hydrogen at 40 psi in the presence of about 5-20% palladium on carbon in a solvent with or without an acid to provide a compound of formula (X) which is optionally purified

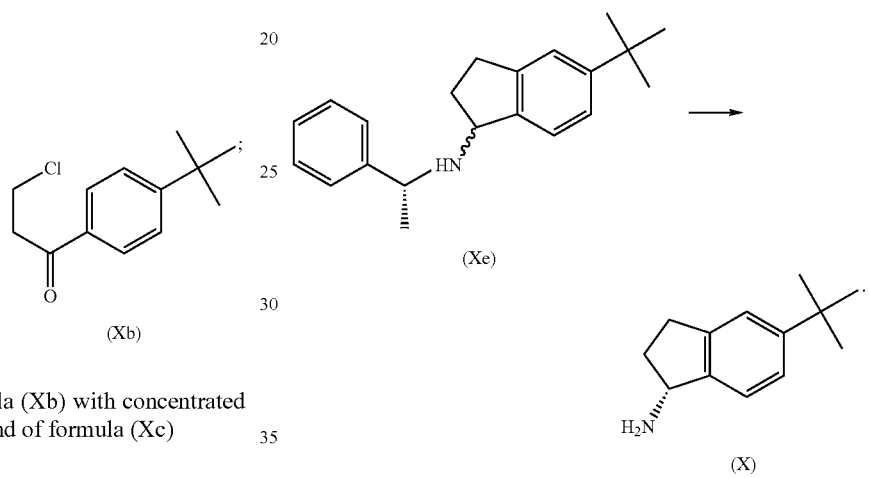

In another embodiment of the present invention the substitution an atmosphere of hydrogen in the presence of palladium or platinum on carbon in a solvent such as but not limited to methanol for sodium borohydride in ethanol in step (c), followed by step (d) to provide the compound of formula (X).

In another embodiment the process for preparing a compound having structural formula (X) contemplates the use of methanol as a solvent in step (d) to provide the compound of formula (X).

In a further embodiment the process for preparing a compound having structural formula (X) contemplates the use of solvents including aqueous methanol containing 1% acetic acid in step (d) to provide the compound of formula (X).

In another embodiment the process for preparing a compound having structural formula (X) contemplates the use of methanol containing 6% acetic acid in step (d) to provide the compound of formula (X).

In another embodiment of the present invention, there is disclosed a process of preparing compounds of formula (X), wherein the compound of formula (Xe) is further purified by preparing the salt with an acid and recrystallized prior to step (d).

In another embodiment of the present invention, there is disclosed a process of preparing compounds of formula (X), wherein the compound of formula (Xe) is further purified by preparing the tosylate salt and recrystallized prior to step (d).

In another embodiment of the present invention, there is disclosed a process of preparing compounds of formula (X), wherein the compound of formula (X) is further purified by preparing the salt with an acid and recrystallized.

In another embodiment of the present invention, there is disclosed a process of preparing compounds of formula (X), wherein the compound of formula (X) is further purified by preparing the tosylate salt and recrystallized.

Another embodiment of the present invention is related to a process for making a compound having structural formula (XI),

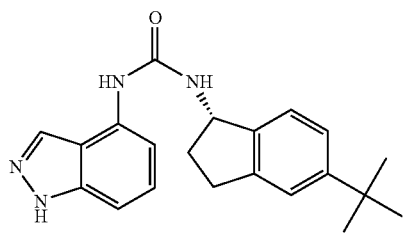

(XI)

comprising, in toto, the steps of: (a) treating a compound of formula (IX) with a compound of formula (X) to provide a compound of formula (XIa)

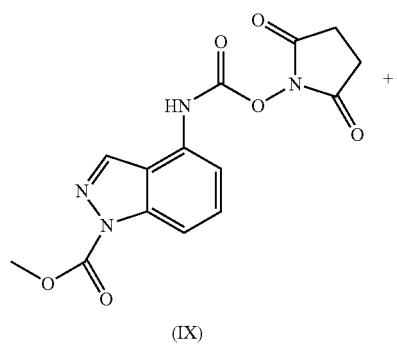

(IX)

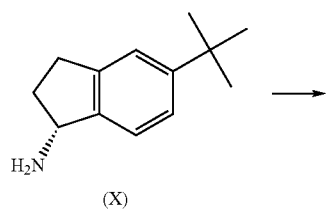

(X)

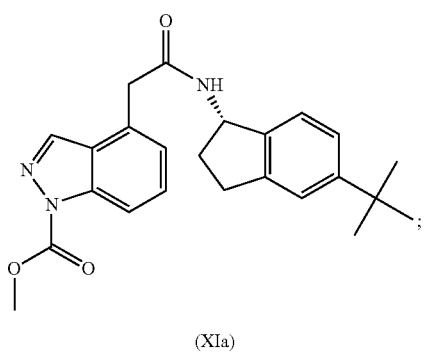

(XIa)

(b) treating a compound of formula (XIa) with sodium hydroxide in methanol to provide the compound of formula (XI)

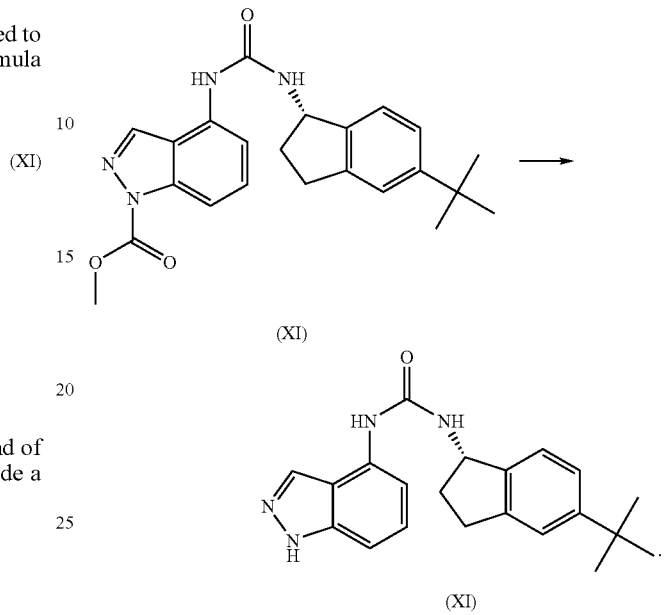

Another embodiment of the present invention relates to the use of a compound of formula (IX) in the process of preparing a compound of formula (I).

Another embodiment of the present invention relates to the use of a compound of formula (IX) in the process of preparing a compound of formula (XI) which is representative of compound of formula (I) which is useful for the treatment of a disorder by inhibiting vanilloid receptor subtype 1 in a mammal comprising administering a therapeutically effective amount of a compound of formula (I) or a pharmaceutically acceptable salt or prodrug thereof.

Another embodiment of the present invention relates to the use of a compound of formula (IX) in the process of preparing a compound of formula (XI) which is representative of compound of formula (I) which is useful for the treatment of pain in a mammal comprising administering a therapeutically effective amount of a compound of formula (I) or a pharmaceutically acceptable salt or prodrug thereof.

Another embodiment of the present invention relates to the use of a compound of formula (X) in the process of preparing a compound of formula (I).

Another embodiment of the present invention relates to the use of a compound of formula (X) in the process of preparing a compound of formula (XI) which is representative of compound of formula (I) which is useful for the treatment of a disorder by inhibiting vanilloid receptor subtype 1 in a mammal comprising administering a therapeutically effective amount of a compound of formula (I) or a pharmaceutically acceptable salt or prodrug thereof.

Another embodiment of the present invention relates to the use of a compound of formula (X) in the process of preparing a compound of formula (XI) which is representative of compound of formula (I) which is useful for the treatment of pain in a mammal comprising administering a therapeutically effective amount of a compound of formula (I) or a pharmaceutically acceptable salt or prodrug thereof.

The present invention also provides pharmaceutical compositions that comprise compounds of the present invention. The pharmaceutical compositions comprise compounds of the present invention that may be formulated together with one or more non-toxic pharmaceutically acceptable carriers.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray.

Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents that delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals, which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants that may be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be used in the form of pharmaceutically acceptable salts derived from inorganic or organic acids.

Pharmaceutically acceptable salts are well-known in the art. For example, S. M. Berge et al. describe pharmaceutically acceptable salts in detail in (J. Pharmaceutical Sciences, Vol. 66 pages 1 et seq., 1977). The salts can be prepared in situ during the final isolation and purification of the compounds of the invention or separately by reacting a free base function with a suitable organic acid. Representative acid addition salts include, but are not limited to benzenesulfonate, bisulfate, chlorobenzene sulfonic acid, 1,5-napthalene disulfonic acid, thiocyanate, dodecyl sulfuric acid, ethanesulfonate, camphorsulfonate, hydrochloride, hydrobromide, 2-hydroxyethansulfonate (isethionate), methanesulfonate, 2-naphthalenesulfonate, sulfate, and p-toluenesulfonate. Examples of acids which can be employed to form pharmaceutically acceptable acid addition salts include such inorganic acids as hydrochloric acid, hydrobromic acid, and sulphuric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The present invention contemplates compounds of formula I formed by synthetic means or formed by in vivo biotransformation of a prodrug. Prodrugs of the present invention may be rapidly transformed in vivo to compounds of formula (I), for example, by hydrolysis in blood.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.01 to about 100 mg/kg/day. For purposes of oral administration, more preferable doses can be in the range of from about 0.1 to about 25 mg/kg/day. If desired, the effective daily dose can be divided into multiple doses for purposes of administration; consequently, single dose compositions may contain such amounts or submultiples thereof to make up the daily dose.

(2) Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through an alkoxy group, as defined herein. Representative examples of alkoxyalkoxy include, but are not limited to, methoxymethoxy, ethoxymethoxy and 2-ethoxyethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylsulfanyl, ethylsulfanyl, tert-butylsulfanyl, and hexylsulfanyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "$Ar_1$" as used herein, means an aryl group selected from dihydro-1H-indenyl, 1H-indenyl, tetrahydronaphthalenyl, or dihydronaphthalenyl. The $Ar_1$ group is attached to the parent molecular moiety via any position. Representative examples include, but are not limited to, 2,3-dihydro-1H-inden-1-yl, 2,3-dihydro-1H-inden-2-yl, 2,3-dihydro-1H-inden-4-yl, 2,3-dihydro-1H-inden-5-yl, 1H-inden-1-yl, 1H-inden-2-yl, 1H-inden-3-yl, 1H-inden-4-yl, 1H-inden-5-yl, 1,2,3,4-tetrahydro-1-naphthalenyl, 1,2,3,4-tetrahydro-2-naphthalenyl, 1,2,3,4-tetrahydro-5-naphthalenyl, 1,2,3,4-tetrahydro-6-naphthalenyl, 1,2-dihydro-1-naphthalenyl, 1,2-dihydro-2-naphthalenyl, 1,2-dihydro-3-naphthalenyl, 1,2-dihydro-4-naphthalenyl, 1,2-dihydro-5-naphthalenyl, 1,2-dihydro-6-naphthalenyl, 1,2-dihydro-7-naphthalenyl, 1,2-dihydro-8-naphthalenyl, 3,4-dihydronaphthalen-1-yl, and 3,4-dihydronaphthalen-2-yl.

The $Ar_1$ groups of this invention can be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)C-$, $-NR_AS(O)_2R_B$, $-S(O)_2OR_A$, $-S(O)_2R_B$, $-NZ_AZ_B$, $(NZ_AZ_B)$alkyl, $(NZ_AZ_B)$carbonyl, $(NZ_AZ_B)$carbonylalkyl or $(NZ_AZ_B)$sulfonyl, wherein $Z_A$ and $Z_B$ are each independently hydrogen, alkyl, alkylcarbonyl, formyl, aryl, or arylalkyl. Representative examples of substituted $Ar_1$ groups include, but are not limited to, 5-tert-butyl-2,3-dihydro-1H-inden-1-yl, 5-tert-butyl-2,3-dihydro-1H-inden-2-yl, 5-bromo-2,3-dihydro-1H-inden-1-yl, (3R)-5-tert-butyl-3-methyl-2,3-dihydro-1H-inden-1-yl, and (3S)-5-tert-butyl-3-methyl-2,3-dihydro-1H-inden-1-yl.

The term "aryl" as used herein, means a phenyl group, or a bicyclic or a tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indenyl, naphthyl, phenyl and tetrahydronaphthyl.

The aryl groups of this invention can be substituted with 1, 2, 3, 4 or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, cycloalkyl, cycloalkylalkyl, ethylenedioxy, formyl, formylalkyl, haloalkoxy, haloalkyl, haloalkylthio, halogen, hydroxy, hydroxyalkyl, methylenedioxy, mercapto, mercaptoalkyl, nitro, $-NZ_CZ_D$, $(NZ_CZ_D)$alkyl, $(NZ_CZ_D)$carbonyl, $(NZ_CZ_D)$carbonylalkyl, $(NZ_CZ_D)$sulfonyl, $-NR_AS(O)_2R_B$, $-S(O)_2OR_A$ and $-S(O)_2R_A$ wherein $R_A$ and $R_B$ are as defined herein. The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "arylthio" as used herein, means an aryl group, as defined herein, appended to the parent molecular moiety through a sulfur atom. Representative examples of arylthio include, but are not limited to, phenylsulfanyl, naphth-2-ylsulfanyl, and 5-phenylhexylsulfanyl.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a saturated monocyclic ring system containing from 3 to 8 carbon atoms. Examples of cycloalkyl include cyclopropyl, cyclobutyl, cyclopentyl, cyclohexyl, cycloheptyl, and cyclooctyl.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl trifluoromethyl, pentafluoroethyl, and 2-chloro-3-fluoropentyl.

The term "haloalkylthio" as used herein, means at least one halogen, as defined herein, appended to the parent molecular moiety through an alkylthio group, as defined herein. Representative examples of haloalkylthio include, but are not limited to, trifluoromethylthio.

The term "heterocycle," as used herein, refers to a three, four, five, six, seven, or eight membered ring containing one or two heteroatoms independently selected from the group consisting of nitrogen, oxygen, and sulfur. The three membered ring has zero double bonds. The four and five membered ring has zero or one double bond. The six membered ring has zero, one, or two double bonds. The seven and eight membered rings have zero, one, two, or three double bonds. The heterocycle groups of the present invention can be attached to the parent molecular moiety through a carbon atom or a nitrogen atom. Representative examples of heterocycle include, but are not limited to, azabicyclo[2.2.1]heptanyl, azabicyclo[2.2.1.]octanyl, azetidinyl, hexahydro-1H-azepinyl, hexahydroazocin-(2H)-yl, indazolyl, morpholinyl, octahydroisoquinoline, piperazinyl, piperidinyl, pyridinyl, pyrrolidinyl, and thiomorpholinyl.

The heterocycles of the present invention are substituted with 0, 1, 2, 3, or 4 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkynyl, aryl, arylalkyl, arylalkoxycarbonyl, carboxy, cyano, formyl, haloalkoxy, haloalkyl, halo, hydroxy, hydroxyalkyl, mercapto, nitro, piperidinyl, and oxo.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —OCH$_2$O— group wherein the oxygen atoms of the methylenedioxy are attached to the parent molecular moiety through two adjacent carbon atoms.

The term "nitro" as used herein, means a —NO$_2$ group.

The term "—NZ$_A$Z$_B$" as used herein, means two groups, Z$_A$ and Z$_B$, which are appended to the parent molecular moiety through a nitrogen atom. Z$_A$ and Z$_B$ are each independently selected from hydrogen, alkyl, alkylcarbonyl, formyl, aryl and arylalkyl. Representative examples of —NZ$_A$Z$_B$ include, but are not limited to, amino, methylamino, acetylamino, benzylamino, phenylamino, and acetylmethylamino.

The term "(NZ$_A$Z$_B$)alkyl" as used herein, means a —NZ$_A$Z$_B$ group, as defined herein, appended to the parent molecular moiety through an alkyl group, as defined herein. Representative examples of (NZ$_A$Z$_B$)alkyl include, but are not limited to, aminomethyl, 2-(methylamino)ethyl, 2-(dimethylamino)ethyl and (ethylmethylamino)methyl.

The term "(NZ$_A$Z$_B$)carbonyl" as used herein, means a —NZ$_A$Z$_B$ group, as defined herein, appended to the parent molecular moiety through a carbonyl group, as defined herein. Representative examples of (NZ$_A$Z$_B$)carbonyl include, but are not limited to, aminocarbonyl, (methylamino)carbonyl, (dimethylamino)carbonyl and (ethylmethylamino)carbonyl.

The term "(NZ$_A$Z$_B$)carbonylalkyl" as used herein, means a (NZ$_A$Z$_B$)carbonyl group, as defined herein, appended to the parent molecular moiety through an alkyl group, as defined herein. Representative examples of (NZ$_A$Z$_B$)carbonylalkyl include, but are not limited to, (aminocarbonyl)methyl, 2-((methylamino)carbonyl)ethyl and ((dimethylamino)carbonyl)methyl.

The term "(NZ$_A$Z$_B$)sulfonyl" as used herein, means a —NZ$_A$Z$_B$ group, as defined herein, appended to the parent molecular moiety through a sulfonyl group, as defined herein. Representative examples of (NZ$_A$Z$_B$)sulfonyl include, but are not limited to, aminosulfonyl, (methylamino)sulfonyl, (dimethylamino)sulfonyl and (ethylmethylamino)sulfonyl.

The term "—NZ$_C$Z$_D$" as used herein, means two groups, Z$_C$ and Z$_D$, which are appended to the parent molecular moiety through a nitrogen atom. Z$_C$ and Z$_D$ are each independently selected from hydrogen, alkyl, alkylcarbonyl, formyl, aryl and arylalkyl. Representative examples of —NZ$_C$Z$_D$ include, but are not limited to, amino, methylamino, acetylamino, benzylamino, phenylamino, and acetylmethylamino.

The term "(NZ$_C$Z$_D$)alkyl" as used herein, means a —NZ$_C$Z$_D$ group, as defined herein, appended to the parent molecular moiety through an alkyl group, as defined herein.

Representative examples of $(NZ_CZ_D)$alkyl include, but are not limited to, aminomethyl, 2-(methylamino)ethyl, 2-(dimethylamino)ethyl and (ethylmethylamino)methyl.

The term "$(NZ_CZ_D)$carbonyl" as used herein, means a —$NZ_CZ_D$ group, as defined herein, appended to the parent molecular moiety through a carbonyl group, as defined herein. Representative examples of $(NZ_CZ_D)$carbonyl include, but are not limited to, aminocarbonyl, (methylamino)carbonyl, (dimethylamino)carbonyl and (ethylmethylamino)carbonyl.

The term "$(NZ_CZ_D)$carbonylalkyl" as used herein, means a $(NZ_CZ_D)$carbonyl group, as defined herein, appended to the parent molecular moiety through an alkyl group, as defined herein. Representative examples of $(NZ_CZ_D)$carbonylalkyl include, but are not limited to, (aminocarbonyl)methyl, 2-((methylamino)carbonyl)ethyl and ((dimethylamino)carbonyl)methyl.

The term "$(NZ_CZ_D)$sulfonyl" as used herein, means a —$NZ_CZ_D$ group, as defined herein, appended to the parent molecular moiety through a sulfonyl group, as defined herein. Representative examples of $(NZ_CZ_D)$sulfonyl include, but are not limited to, aminosulfonyl, (methylamino)sulfonyl, (dimethylamino)sulfonyl and (ethylmethylamino)sulfonyl.

The term "oxo" as used herein, means =O.

The term "sulfonyl" as used herein, means a —$S(O)_2$— group.

The term "parenterally," as used herein, refers to modes of administration which include intravenous, intramuscular, intraperitoneal, intrasternal, subcutaneous and intraarticular injection and infusion.

The terms "pharmaceutically acceptable carrier," as used herein, mean a non-toxic, inert solid, semi-solid or liquid filler, diluent, encapsulating material or formulation auxiliary of any type.

The terms "therapeutically effective amount" of the compound of the invention mean a sufficient amount of the compound to treat disorders, at a reasonable benefit/risk ratio applicable to any medical treatment.

The terms "pharmaceutically acceptable salt" mean those salts which are, within the scope of sound medical judgement, suitable for use in contact with the tissues of humans and lower animals without undue toxicity, irritation, allergic response and the like and are commensurate with a reasonable benefit/risk ratio.

The terms "pharmaceutically acceptable prodrug" or "prodrug," as used herein, represent those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The term "amorphous" as used herein, means a solid essentially without cristallinity. The terms "essentially without," in reference to absence of crystallinity, mean at least about 95% amorphous, preferably about 97% amorphous, more preferably about 99% amorphous, and most preferably about 100% amorphous.

Compounds of the present invention can exist as stereoisomers, wherein asymmetric or chiral centers are present. Stereoisomers are designated (R) or (S), depending on the configuration of substituents around the chiral carbon atom. The terms (R) and (S) used herein are configurations as defined in IUPAC 1974 Recommendations for Section E, *Fundamental Stereochemistryy Pure Appl. Chem.* Vol. 45, pages 13-30 (1976). The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials, which contain asymmetric or chiral centers, or by preparation of racemic mixtures followed by resolution, a technique well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) direct separation of the mixture of optical enantiomers on chiral chromatographic columns, or (3) formation of a diastereomeric salt followed by selective recrystallization of one of the diastereomeric salts.

Compounds of the present invention were named by ACD/ChemSketch version 5.0 (developed by Advanced Chemistry Development, Inc., Toronto, ON, Canada) or were given names that appeared to be consistent with ACD nomenclature.

Abbreviations

Abbreviations which have been used in the descriptions of the Schemes and the Examples that follow are: atm for atmosphere(s); DBU for 1,8-diazabicyclo[5.4.0]undec-7-ene; DCC for 1,3-dicyclohexylcarbodiimide; DMAP for 4-dimethylaminopyridine; DMF for N,N-dimethylformamide; DMSO for dimethylsulfoxide; EDCI or EDC for 1-ethyl-3-[3-(dimethylamino)propyl]-carbodiimide hydrochloride; Et for $CH_3CH_2$; HPLC high pressure liquid chromatography; Me for $CH_3$; Ph for phenyl; psi for pounds per square inch; and THF for tetrahydrofuran.

(3) Preparation of Compounds of the Present Invention

The compounds and processes of the present invention will be better understood in connection with the following synthetic Schemes and Examples that illustrate a means by which the compounds of the present invention can be prepared.

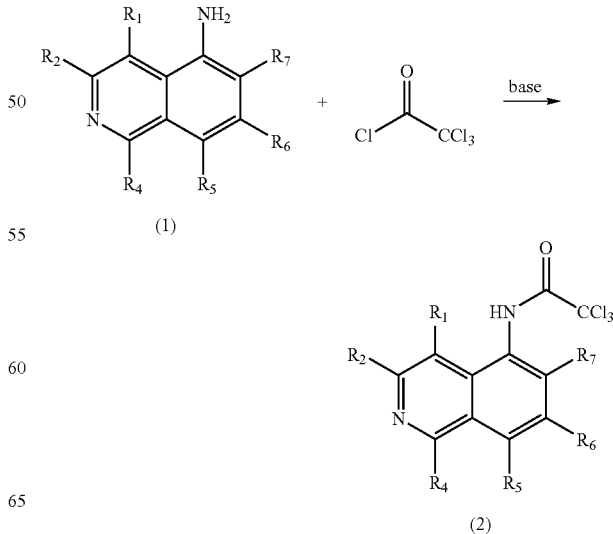

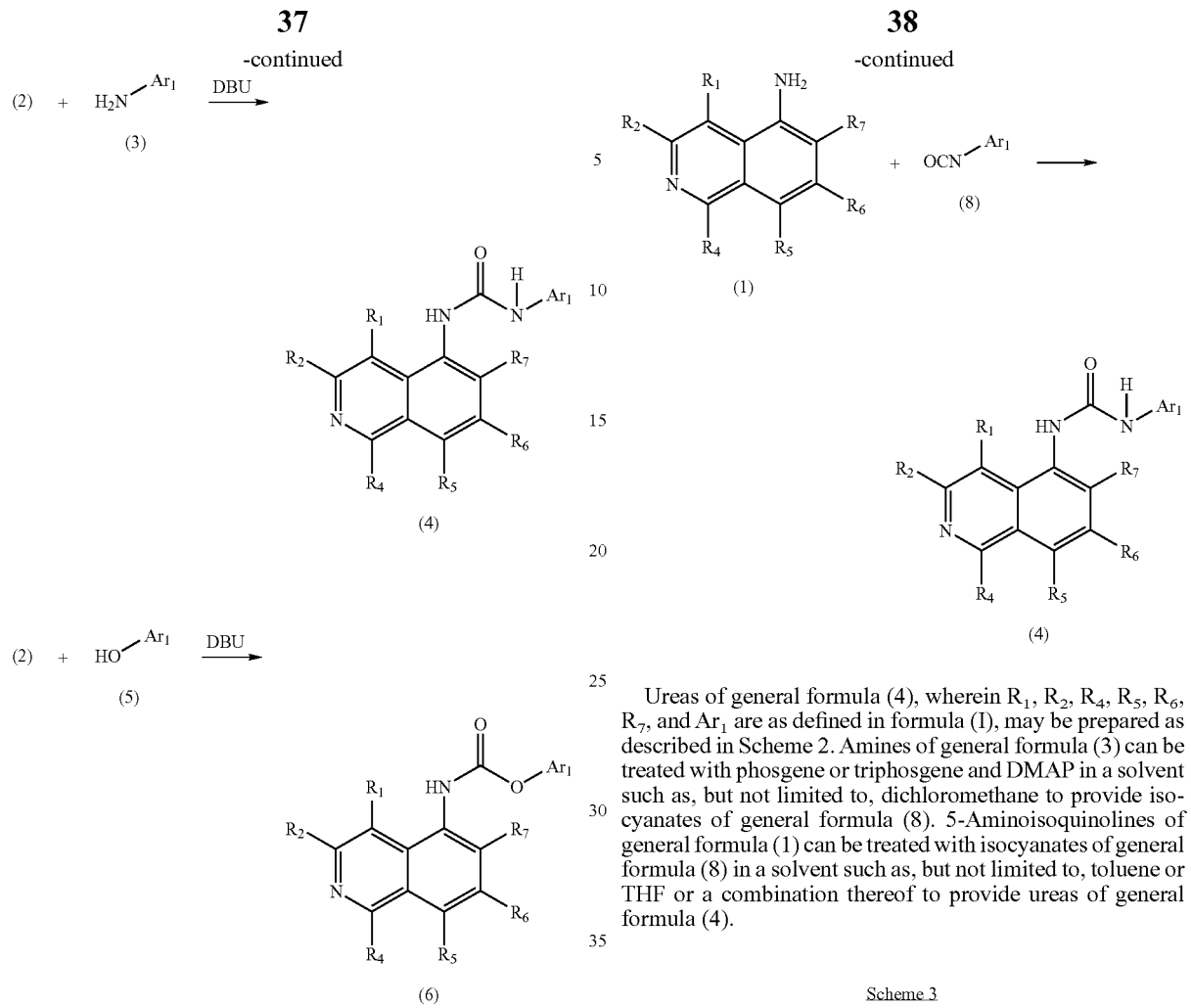

Ureas of general formula (4), wherein $R_1$, $R_2$, $R_4$, $R_5$, $R_6$, $R_7$, and $Ar_1$ are as defined in formula (I), may be prepared as described in Scheme 2. Amines of general formula (3) can be treated with phosgene or triphosgene and DMAP in a solvent such as, but not limited to, dichloromethane to provide isocyanates of general formula (8). 5-Aminoisoquinolines of general formula (1) can be treated with isocyanates of general formula (8) in a solvent such as, but not limited to, toluene or THF or a combination thereof to provide ureas of general formula (4).

Ureas of general formula (4), wherein $R_1$, $R_2$, $R_4$, $R_5$, $R_6$, $R_7$, and $Ar_1$ are as defined in formula (I), may be prepared as described in Scheme 1. 5-Aminoisoquinolines of general formula (I), purchased commercially or prepared using standard chemistry known to those in the art, can be treated with trichloroacetyl chloride and a base such as, but not limited to, triethylamine in a solvent such as dichloromethane to provide trichloroacetamides of general formula (2). Trichloroacetamides of general formula (2) can be treated with amines of general formula (3) and a non-nucleophilic base such as, but not limited to, DBU in a solvent such as, but not limited to, acetonitrile to provide ureas of general formula (4).

Carbamates of general formula (6), wherein $R_1$, $R_2$, $R_4$, $R_5$, $R_6$, $R_7$, and $Ar_1$ are as defined in formula (I), may also be prepared as described in Scheme 1. Trichloroacetamides of general formula (2) can be treated with alcohols of general formula (5) and a non-nucleophilic base such as, but not limited to, DBU in a solvent such as, but not limited to, acetonitrile to provide carbamates of general formula (6).

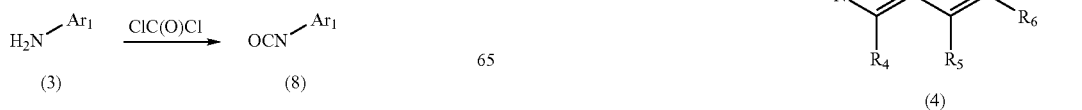

Ureas of general formula (4), wherein $R_1$, $R_2$, $R_4$, $R_5$, $R_6$, $R_7$, and $Ar_1$ are as defined in formula (I), may be prepared as described in Scheme 3. 5-Aminoisoquinolines of general formula (I) can be treated with phosgene or triphosgene and DMAP in a solvent such as, but not limited to, dichloromethane to provide isocyanates of general formula (10). Isocyanates of general formula (10) can be treated with amines of general formula (3) in a solvent such as, but not limited to, toluene or THF or a combination thereof to provide ureas of general formula (4).

as defined in formula (I), may be prepared as described in Scheme 4. 4-Aminoindazoles of general formula (22), purchased commercially or prepared using standard chemistry known to those in the art, may be processed as described in Schemes 1-3 to provide ureas of general formula (23) and carbamates of general formula (24).

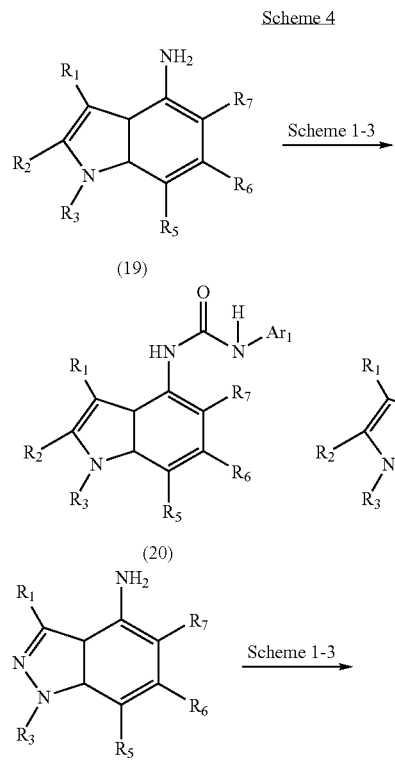

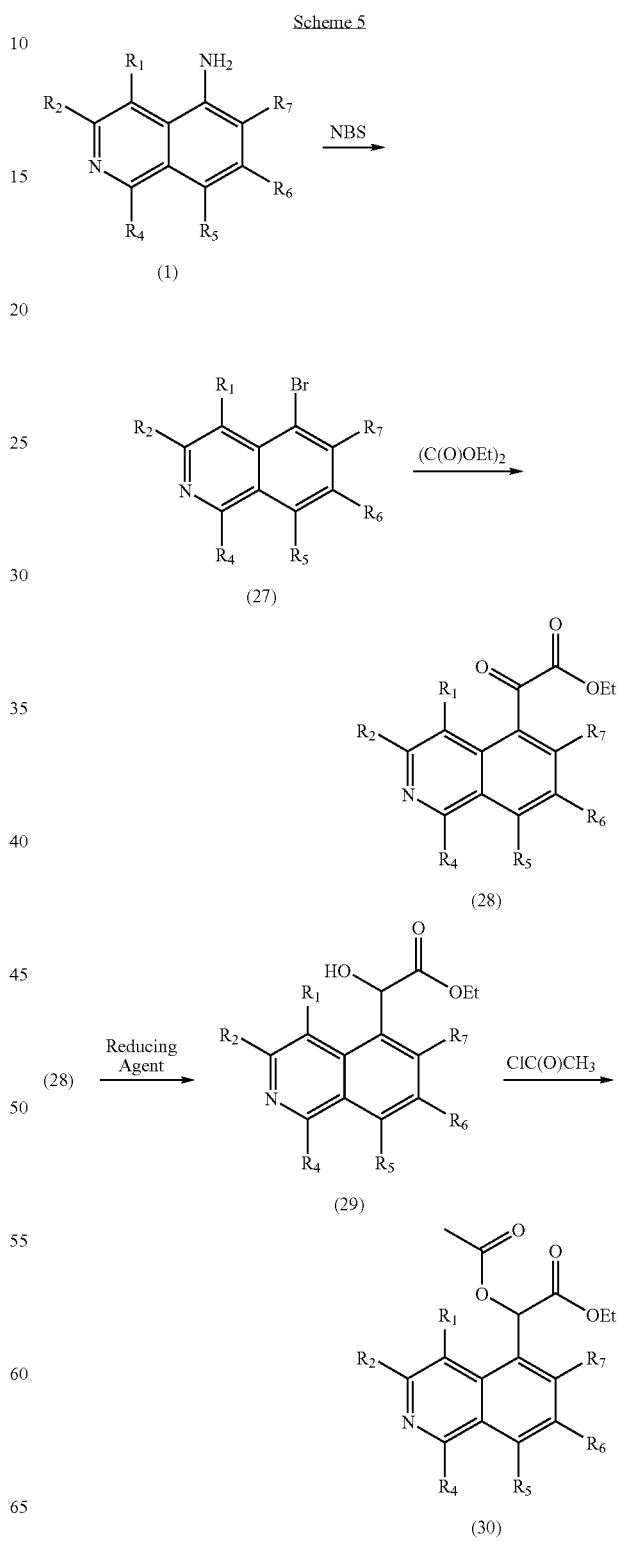

Ureas of general formula (20), wherein $R_1$, $R_2$, $R_3$, $R_5$, $R_6$, $R_7$, and $Ar_1$ are as defined in formula (I), and carbamates of general formula (21), wherein $R_1$, $R_2$, $R_3$, $R_5$, $R_6$, $R_7$, and $Ar_1$ are as defined in formula (I), may be prepared as described in Scheme 4. 4-Aminoindoles of general formula (19), purchased commercially or prepared using standard chemistry known to those in the art, may be processed as described in Schemes 1-3 to provide ureas of general formula (20) and carbamates of general formula (21).

Ureas of general formula (23), wherein $R_1$, $R_3$, $R_5$, $R_6$, $R_7$, and $Ar_1$ are as defined in formula (I), and carbamates of general formula (24), wherein $R_1$, $R_3$, $R_5$, $R_6$, $R_7$, and $Ar_1$ are 41
-continued

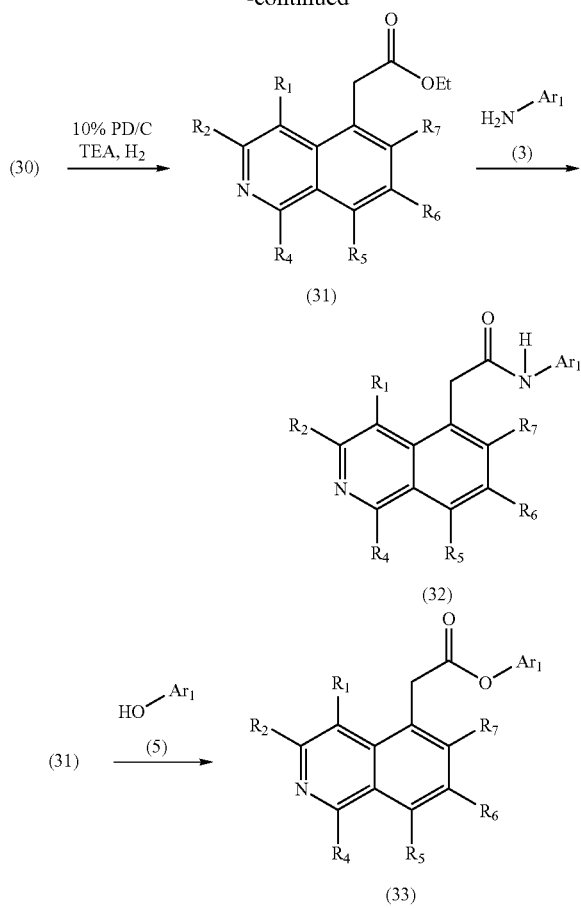

Amides of general formula (32), wherein $R_1$, $R_2$, $R_4$, $R_5$, $R_6$, $R_7$, and $Ar_1$ are as defined in formula (I), can be prepared as described in Scheme 5. Amines of general formula (I) can be treated with an acid such as, but not limited to, concentrated sulfuric acid and N-bromosuccinimide (NBS) to provide bromides of general formula (27). Bromides of general formula (27) can be treated with an organolithium reagent such as, but not limited to, n-butyllithium and diethyl oxalate in a solvent such as, but not limited to, THF to provide keto esters of general formula (28). Keto esters of general formula (28) can be treated with a reducing agent such as, but not limited to, 10% Pd/C under a hydrogen atmosphere (50 psi) in a solvent such as, but not limited to, ethanol to provide hydroxy esters of general formula (29). Hydroxy esters of general formula (29) can be treated with an acid chloride such as, but not limited to, acetyl chloride in a solvent such as, but not limited to, pyridine to provide diesters of general formula (30). Diesters of general formula (30) can be treated with 10% Pd/C and a base such as, but not limited to, triethylamine under a hydrogen atmosphere (60 psi) in a solvent such as, but not limited to, ethanol to provide esters of general formula (31). Esters of general formula (31) can be treated with amines of general formula (3) to provide amides of general formula (32). Alternatively, esters of general formula (31) can be treated with aqueous base such as, but not limited to, aqueous sodium hydroxide or aqueous potassium hydroxide to provide the acids which can then be converted into amides of general formula (32) by treatment with amines of general formula (3) under standard DCC or EDCI coupling procedures that are well known in the art.

42

Esters of general formula (33), wherein $R_1$, $R_2$, $R_4$, $R_5$, $R_6$, $R_7$, and $Ar_1$ are as defined in formula (I), can be prepared as described in Scheme 5. Esters of general formula (31) can be treated with alcohols of general formula (5) under standard transesterification conditions well known to those of skill in the art to provide esters of general formula (33).

Scheme 6

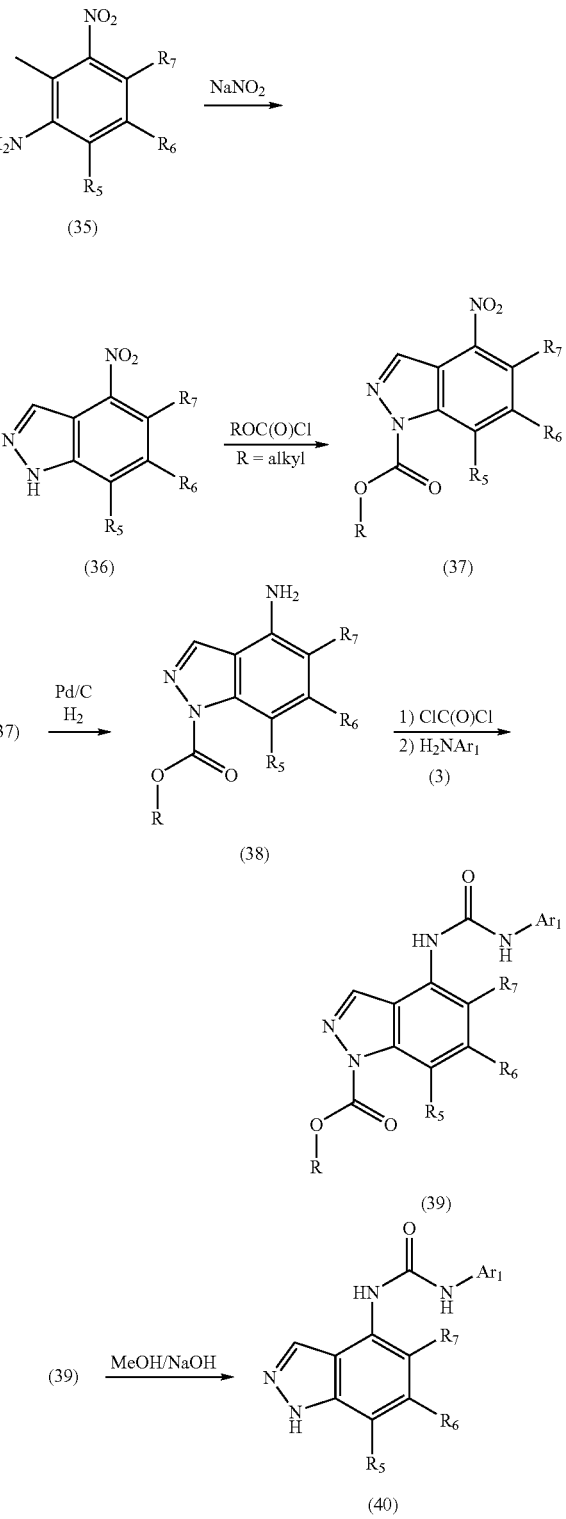

Ureas of general formula (39) and ureas of general formula (40), wherein $R_5$, $R_6$, $R_7$, and $Ar_1$ are as defined in formula (I) and R is alkyl as defined herein, can be prepared as described in Scheme 6. Nitro anilines of general formula (35) can be treated with sodium nitrite and an acid including, but not limited to, acetic acid in water to provide indazoles of general formula (36). Indazoles of general formula (36) can be treated with chloroformates to provide indazoles of general formula (37). Indazoles of general formula (37) can be treated with a transition metal catalyst including, but not limited to, palladium on carbon under a hydrogen atmosphere (about 1 atm to about 60 atm) to provide indazoles of general formula (38). Indazoles of general formula (38) can be processed as described in Scheme 1-3 to provide indazoles of general formula (39). Indazoles of general formula (39) can be treated with a base including, but not limited to, sodium hydroxide or potassium hydroxide to provide indazoles of general formula (40).

Scheme 7

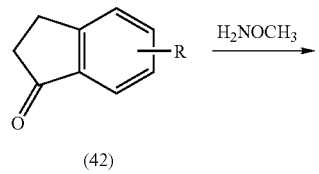

2,3-Dihydro-1H-inden-1-ylamines of general formula (44), wherein R is 1, 2, 3, 4, or 5 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkynyl, carboxy, carboxyalkyl, cyano, cyanoalkyl, formyl, formylalkyl, haloalkoxy, haloalkyl, haloalkylthio, halogen, hydroxy, hydroxyalkyl, mercapto, mercaptoalkyl, nitro, $(CF_3)_2(HO)$C—, $—NR_AS(O)_2R_B$, $—S(O)_2OR_A$, $—S(O)_2R_B$, $—NZ_AZ_B$, $(NZ_AZ_B)$alkyl, $(NZ_AZ_B)$carbonyl, $(NZ_AZ_B)$carbonylalkyl or $(NZ_AZ_B)$sulfonyl, wherein $Z_A$ and $Z_B$ are each independently hydrogen, alkyl, alkylcarbonyl, formyl, aryl, or arylalkyl, can be prepared as described in Scheme 7. Indan-1-ones of general formula (42) can be treated with hydroxylamines including, but not limited to, O-methylhydroxylamine to provide oximes of general formula (43). Oximes of general formula (43) can be treated with palladium on carbon under a hydrogen atmosphere (about 1 atm to about 60 atm) to provide 2,3-dihydro-1H-inden-1-ylamines of general formula (44).

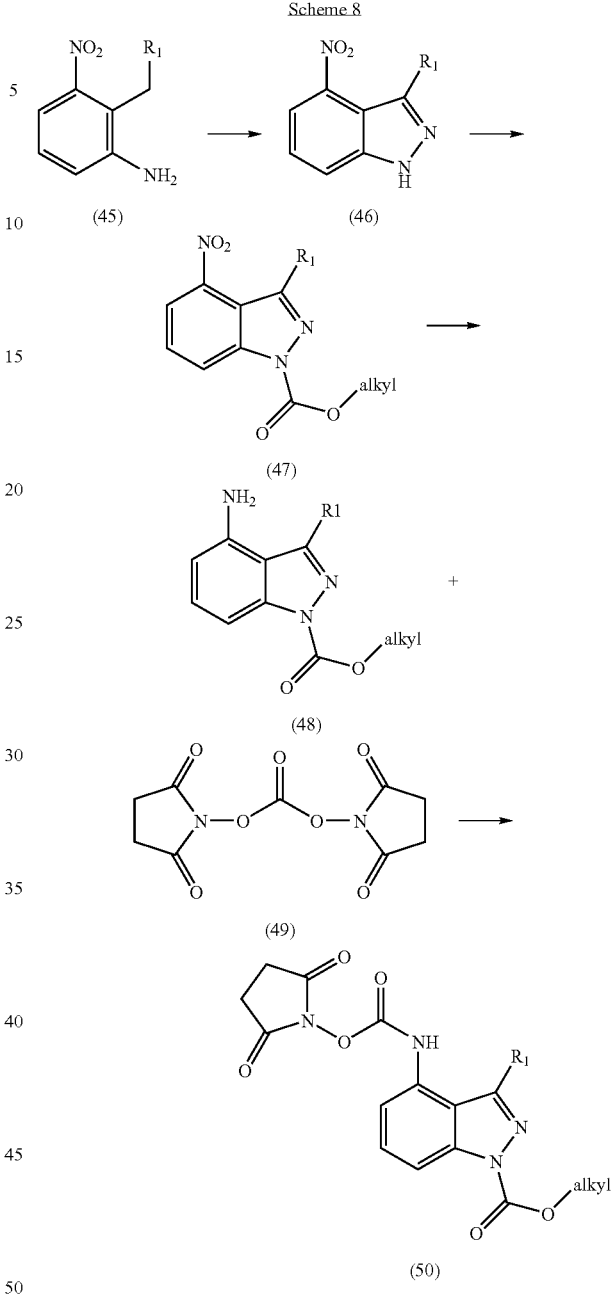

As shown in Scheme 8, 2-alkyl substituted 3-nitro-aniline compounds of formula (45) wherein $R_1$ is alkyl, when treated with sodium nitrite in acetic acid will provide a compound of formula (46). Compounds of formula (46) when treated with an alkyl chloroformate and a base such as but not limited to 1,8-diazabicyclo[5.4.0]undec-7-ene will provide a compound of formula (47). Compounds of formula (47) treated with an atmosphere of hydrogen in the presence of palladium on carbon in a solvent such as but not limited to methanol will provide a compound of formula (48). Alternative solvents may include mixtures of aqueous methanol containing 1% of acetic acid or methanol containing 6% acetic acid. Compounds of formula (48) when treated with compounds of formula (49) in solvents such as but not limited to acetonitrile will provide a compound of formula (50).

Scheme 9

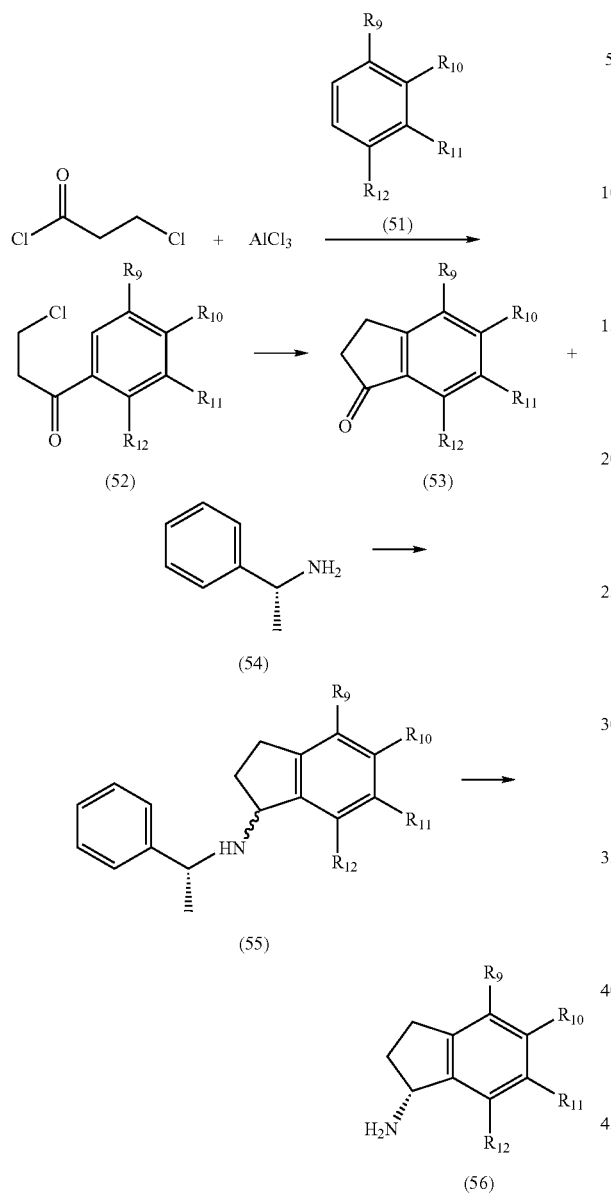

Scheme 10

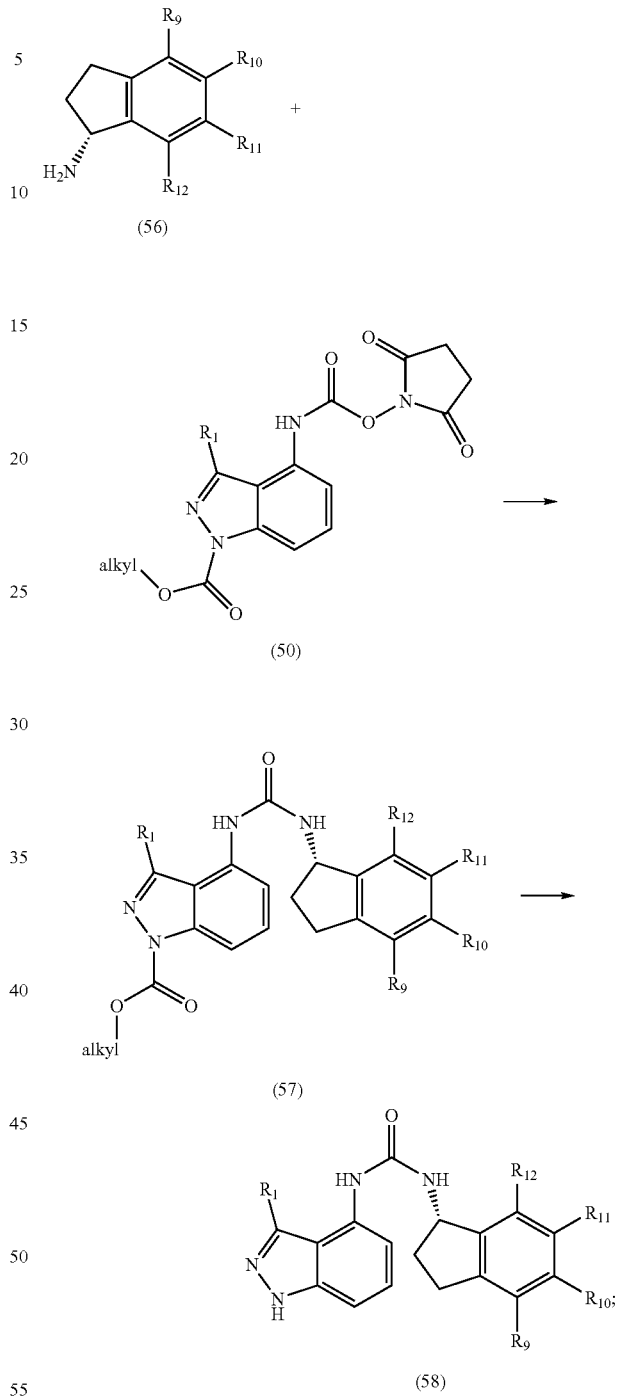

As shown in Scheme 9, chloropropionyl chloride when treated with aluminum chloride in a solvent such as but not limited to methylene chloride followed by the addition of a compound of formula (51) will provide a compound of formula (52). Compounds of formula (52) when treated with concentrated sulfuric acid followed by heating will provide compounds of formula (53). A compound of formula (53) and a compound of formula (54) in toluene heated under Dean-Stark conditions with or without a catalytic amount of acid over a period of time until a molar equivalent of water has been removed, followed by reduction with sodium borohydride in ethanol will provide a compound of formula (55). A compound of formula (55) when treated with a 40 psi atmosphere of hydrogen in the presence of a palladium on carbon catalyst in solvents such as but not limited to methanol or ethanol containing a catalytic amount of acetic acid will provide compounds of formula (56).

As shown in Scheme 10, compounds of formula (56) when treated with compounds of formula (50) will provide compounds of formula (57). Typical solvents include but are not limited to acetonitrile or DMF. Compounds of formula (57) when treated with sodium hydroxide will provide compounds of formula (58), which are representative of the compounds of the present invention. Typical solvents include but are not limited to methanol, ethanol and mixtures of solvents such as DMF and methanol. The two steps may be conducted sequentially with or without isolation of the product (57).

General Process Procedures as Outlined in Scheme 8-10

Compound of Formula (46)

4-nitro-3-substituted-1H-indazole

Sodium nitrite (1.5-2.7 equivalents) and water (0.5-2.5 mL/g of aniline) are stirred until all solids are dissolved, then cooled to about 0-10° C. 2-alkyl substituted-3-nitroaniline (compound of formula (45)) wherein the 3-position may be substituted with either hydrogen or alkyl) and acetic acid (10-50 mL/g of aniline) are mixed in a second reactor and cooled to about 10-30° C. The sodium nitrite solution is transferred to the second reactor as fast as possible. The mixture is stirred and monitored for the consumption of aniline. The mixture is concentrated under reduced pressure to provide an orange solid. The solid is reslurried in water (10-50 mL/g of aniline), filtered, washed with water, and dried at about 40-90° C. to provide 4-nitro-3-substituted-1-H-indazole (typically 80-85% yield).

Compound of Formula (47)

4-nitro-3-substituted-indazole-1-carboxylic acid alkyl ester 4-nitro-3-substituted-indazole (compound of formula (46)) wherein the 3 position is substituted with either hydrogen of alkyl) and DMF (5-15 mL/g of nitroindazole) in a reactor are stirred until all solids are dissolved, and cooled to about 0-20° C. 1,8-diazabicyclo[5.4.0]unde-7-ene (1.0-2.5 equivalents) is added to the reactor followed by methyl chloroformate (1.0-2.5 equivalents). The mixture is monitored for the consumption of nitroindazole after which 10% aqueous potassium dihydrogenphosphate solution (1-10 mL/g of nitroindazol) is added to the reactor. The solid is filtered and washed sequentially with 10% aqueous potassium dihydrogenphosphate solution, water, and dried in a tray drier at about 40-90° C. The dark brown solid is slurried in isopropyl acetate (5-30 mL/g of indazole), filtered, washed with fresh isopropyl acetate, and dried at about 40-90° C. to provide 4-nitro-3-substituted-indazole-1-carboxylic acid alkyl ester (compound of formula (47)) (typically 80-90% yield).

Compound of Formula (48)

4-amino-3-alkyl-indazole-1-carboxylic acid alkyl ester, HCl salt 4-nitro-3-substituted-indazole-1-carboxylic acid alkyl ester (compound of formula (47)) and THF (5-20 mL/g of nitroindazole) are added to a pressure reactor. 5% Palladium on carbon (0.1-0.5 g/g of nitroindazole carbamate) is added to the reactor. The mixture is degassed then shaken under a 20-60 psi hydrogen atmosphere. The mixture is monitored for the consumption of starting material. The catalyst is filtered and rinsed with fresh THF and the filtrate solution is treated with 12M HCl (1.0-3.0 equivalent of dry HCl). The solid that precipitates is filtered, washed with isopropanol, and dried at about 40-90° C. to provide 4-amino-3-substituted-indazole-1-carboxylic acid alkyl ester HCl salt, compound of formula (48) (typically 80-90% yield).

Compound of Formula 50

Activated Carbamate 3-alkyl-indazole 4-aminoindazole-1-carboxylic acid methyl ester, HCl salt (compound of formula (48)) (1.0 equivalent) and acetonitrile (5-20 mL/g of salt) are added to a pressure reactor. N,N'-Dissuccinimidylcarbonate (1.0-3.0 equivalents) is added to the reactor followed by pyridine (1.0-3.0 equivalents). The mixture is heated to about 25-60° C. for a minimum of 15-25 hours. The mixture is cooled to 15-35° C. The solid is filtered, washed with acetonitrile, and dried at about 40-90° C. to provide the activated carbamate indazole compound of formula (50) (typically 80-90% yield).

Compound of Formula (52)

1-(substituted-phenyl)-3-chloro-propan-1-one

3-Chloropropionyl chloride is added to a slurry of aluminum chloride (1.0-1.5 eq) in a solvent such as but not limited to methylene chloride between –10 and –20° C. The mixture is stirred for 1-3 hours after which compound of formula (51) (1.0-1.5 eq) is added to the mixture at a temperature between –10-25° C. and the mixture stirred for 1-15 hours. The mixture is diluted with aqueous hydrochloric acid solution and the layers are separated. The organic layer is concentrated under reduced pressure to provide the title compound.

Compound of Formula (53)

(4,5,6,7-substituted) indanone

Compound of formula (52) is added to 12 Molar sulfuric acid (3-15 ml/g) and heated between 70-110° C. for 1-3 hours. The mixture is diluted with water and extracted with organic solvent such as but not limited to ethyl acetate. The organic layer is separated, concentrated under reduced pressure to provide the title compound as an oil (typically 80% yield).

Compound of Formula (55)

N-[(1R)-2,3-dihydro-(4,5,6,7 substituted)-1H-inden-1-yl]-N-[(1R)-1-phenylethyl]amine To a reaction vessel was added compound of formula (53) (wherein the 4, 5, 6 and 7 position may be substituted as described by $R_9$, $R_{10}$, $R_{11}$ and $R_{12}$ of formula (I)) (1.0 equiv by assay), solvent (toluene or heptanes or THF, 5-15 vol; optimally 8 vol toluene), (R)-methylbenzylamine (1.0 to 5.0 equiv; optimally 2.0 equiv), with or without a catalyst such as but not limited to <1% TFA, <2% TsOH—$H_2O$, <2.0 equiv $MgSO_4$, <2 equiv $CaSO4$, <2.0 equiv $TiCl_4$, <2.0 equiv $Ti(OEt)_4$, <200 wt % 4 A molecular sieves. The solution was heated to 80-120° C. for 6-29 hours. A Dean-Stark apparatus or condenser or an atmospheric distillation configuration may be used with the set-up. A suspension of $NaBH_4$ (1.0-2.5 equiv; optimally 2.0 equiv) in EtOH (5-15 vol; optimally 10 vol) inside a reaction vessel was cooled to <10° C. (optimally 0° C.). The imine solution was added via an addition funnel while maintaining the internal temperature at <10° C. (optimally 0° C.). Ethanol was applied as a rinse and added to the reaction mixture. The mixture was allowed to stir at <10° C. (optimally 0-5° C.). The reaction was quenched by addition of water. The bulk of the mixture was concentrated under reduced pressure.

The distillation residue was taken up in water and EtOAc and separated. The aqueous layer was extracted again with EtOAc. The organic layers were combined, washed with 10% NaCl, and concentrated. The residue was dissolved in toluene and EtOAc. The product was extracted into 1 M $H_3PO_4$. The aqueous layers were combined and washed with MTBE.

To isolate the secondary amine, the aqueous fraction was combined with MTBE and the pH adjusted to 10. The organic layer obtained was concentrated to yield the crude oil. The crude oil was subjected to the next step without further purification.

Compound of Formula (56)

(1R)-2,3-(4,5,6,7 substituted)-dihydro-1H-inden-1-ylamine

To the reaction vessel was charged the compound of formula (55) (1.0 equiv), MeOH (4-10 vol; optimally 4 vol), acid (HOAc, $H_3PO_4$, $H_3BO_3$, 1-5 equiv; optimally 2.5 equiv HOAc), water (0-50 wt %), and catalyst (various loadings of Pd/C or Pd(OH)$_2$/C or Pt/C, PtO$_2$, 0-50 wt %). The mixture was pressured with $H_2$ (40-100 psi; optimally 40 psi) and shaken at ambient temperature. The mixture was filtered and the solvent removed to provide the title compound.

Resolution of Compound of Formula (56) Via N—Ac-D-Leucine Salt Formation

To a reaction vessel was charged N—Ac-D-leucine (0.8-1.5 equiv; optimally 1.1 equiv), amine (1.0 equiv by assay), and solvent (MeOH or EtOH, 8-20 vol; optimally 13 vol). After heating the mixture to reflux, more solvent was added in portions to dissolve all the solids. The solution was cooled to ambient, and the slurry was filtered. The wetcake was washed, dried in a vacuum oven.

The white solid was dissolved in a caustic solution, and the amine extracted with an aprotic organic solvent (IPAc or MTBE or toluene or $CH_2Cl_2$). The organic layers were combined and concentrated. The crude amine was subjected to coupling without further purification.

Alternative Preparation of Compound of Formula (56)

A mixture of compound of formula (53) (wherein the 4, 5, 6 and 7 position may be substituted as described by $R_9$, $R_{10}$, $R_{11}$ and $R_{12}$ of formula (I)) (1.0 equiv by assay), (R)-methylbenzylamine (1.0 to 5.0 equiv; optimally 2.0 equiv) in a solvent (toluene or heptanes or THF, 5-15 vol; optimally 8 vol toluene) with or without acetic acid, trifluoroacetic acid or p-toluene sulfonic acid, was heated to 80-120° C. for 6-29 hours. To the mixture was added catalyst (various loadings of Pd/C or Pd(OH)$_2$/C or Pt/C, PtO$_2$, 0-50 wt %), and solvent (MeOH or EtOH). The mixture was hydrogenated at 0-40° C. under $H_2$ pressure (40-100 psi). To the reaction mixture was then charged acid catalyst (HOAc, $H_3PO_4$, $H_3BO_3$, 1-5 equiv; optimally 2.5 equiv HOAc). The debenzylation reaction occurred under $H_2$ pressure at (40-100 psi) ambient –40° C. When the reaction was complete, the catalyst was filtered and washed with solvent.

A solution of the product and TsOH—$H_2O$ (0.8-2.0 equiv; optimally 1.0 equiv relative to product by solution assay) in a reaction vessel was concentrated under reduced pressure. The thick oil was heated, then water was added slowly to precipitate product. A heat/cool cycle is optional. The crude crystals were collected by filtration, and the wetcake was washed with water. The wetcake was returned to the flask along with toluene and methanol (0-3% relative to volume of toluene; optimally 1%). A heat/cool cycle is optional. The desired product was isolated by filtration, and the wetcake was washed with toluene. The material was dried in a vacuum oven.

Compound of Formula 58

N-[(1R)-2,3-dihydro-(4,5,6,7 substituted) 1H-inden-1-yl]-N'-1H-indazol-4-ylurea

Diisopropylethylamine (2-3 eq) is added at to a slurry containing compound of formula (57) and compound of formula (56) (wherein the 4, 5, 6 and 7 position may be substituted as described by $R_9$, $R_{10}$, $R_{11}$ and $R_{12}$ of formula (I)) (0.9-1.3 eq) in DMF between 0-40° C. Sodium hydroxide solution in methanol (2-3 eq) is then added to the mixture at 0-40° C. After an additional 10 minutes, the mixture is diluted with water and the title compound is collected by filtration.

(4) EXAMPLES

The following Examples are intended as an illustration of and not a limitation upon the scope of the invention as defined in the appended claims.

Example 1

N-(5-tert-butyl-2,3-dihydro-1H-inden-1-yl)-N'-5-isoquinolinylurea

Example 1A 1-(4-tert-butylphenyl)-3-chloro-1-propanone

A solution of tert-butyl benzene (31 ml, 200 mmol) and 3-chloro-propionyl chloride (19 ml, 200 mmol) in methylene chloride (75 ml) was added dropwise to a suspension of aluminum chloride (29.33 g, 220 mmol) in methylene chloride (300 ml) at 0° C. The reaction mixture was allowed to warm to ambient temperature, stirred for 16 hours, and quenched with water dropwise. The reaction mixture was washed with water, dried with magnesium sulfate, and the filtrate was evaporated under reduced pressure to provide the title compound which was used without further purification in the next step.

Alternatively, to a flask fitted with a mechanical stirrer, a nitrogen inlet, a thermocouple, and an addition funnel was charged aluminum trichloride (67.2 g, 0.505 mol) and dichloromethane (600 mL). The suspension was cooled to ~1° C. and 3-chloropropionyl chloride (64.1 g, 0.505 mol.) was added over 5 minutes. To the resulting clear solution, t-butylbenzene (64.4 g, 0.48 mol.) was added via addition funnel while keeping the internal temperature below 5° C. After stirring for 20 minutes at 0-1° C. the reaction was found complete by HPLC, and the mixture was slowly transferred into aqueous hydrochloric acid (prepared by mixing 960 mL of water with 240 ml of conc. hydrochloric acid) maintaining the internal temperature below 5° C. The organic layer was separated and washed with 5% hydrochloric acid (600 mL). The organic layer was separated, diluted with heptanes (150 ml) and dried with magnesium sulfate (10 g). Filtration and concentration in vacuo gave chloroketone intermediate 112 g (99% yield) which was diluted with 60 ml of methylene chloride and used in the cyclization step.

Example 1B 5-tert-butyl-1-indanone 1-(4-tert-Butylphenyl)-3-chloro-1-propanone (22.25 g, 99 mmol) was dissolved in concentrated sulfuric acid (100 ml) and heated on a water bath at 95° C. for 2.5 hours. The reaction mixture was cooled, poured onto ice, and extracted with diethyl ether. The combined organic extracts were washed with saturated aqueous sodium bicarbonate, dried with magnesium sulfate, and the filtrate was evaporated under reduced pressure to provide the title compound which was used without further purification in the next step.

Alternatively, chloroketone intermediate was added over 2 hours to concentrated sulfuric acid (600 mL) heated to 90° C. After additional 1 hour at 90° C., the reaction was complete by HPLC and the mixture was cooled to 15° C. The mixture was slowly transferred into a mixture of water (1.2 L), MTBE (0.3 L) and heptanes (0.3 L) precooled to 0° C., while maintaining the internal temperature <10° C. The organic layer was separated and washed with aqueous potassium carbonate solution (10%, 200 mL). The organic layer was concentrated in vacuo and chased with heptanes (100 mL). The resulting yellow oil crystallized upon cooling to ambient temperature to 71 g of indanone (89% yield). $^1$H-NMR (CDCl$_3$, 400 MHz): 7.68 ppm (br. d, 1H), 7.47 (br. s., 1H), 7.42 (br.d, 1 H), 4.14-4.06 (m, 2H), 3.12 (m, 2 H), 2.68 (m, 2H), 1.36 (s, 9H).

Example 1C 5-tert-butyl-1-indanone O-methyloxime 5-tert-Butyl-1-indanone (13.41 g, 71.23 mmol) and methoxyamine hydrochloride (6.68 g, 80 mmol) were dissolved in pyridine (75 ml) and stirred at ambient temperature for 16 hours. The mixture was evaporated under reduced pressure and the residue was partitioned between water and diethyl ether (X2). The combined organic layers were washed with 1N aqueous hydrochloric acid, dried with magnesium sulfate, and the filtrate was evaporated under reduced pressure to provide the title compound which was used without further purification in the next step.

Example 1D 5-tert-butyl-2,3-dihydro-1H-inden-1-ylamine 5-tert-Butyl-1-indanone O-methyloxime (4.37 g, 20.2 mmol) and 10% palladium on carbon (2.2 g) were combined in methanol (50 ml) and ammonia (10 ml) and placed in a Parr apparatus, which was charged with hydrogen to 60 psi. The reaction was shaken at 50° C. for 16 hours. The reaction mixture was filtered and the filtrate was evaporated under reduced pressure. The residue was treated with diethyl ether (100 ml) and extracted with hydrochloric acid (1N, 3×50 ml). The combined aqueous extracts were neutralized with sodium hydroxide (6 g) in water (25 ml) and extracted with diethyl ether. The organic extracts were combined, dried with magnesium sulfate, and the filtrate was evaporated under reduced pressure to provide the title compound, which was used without further purification in the next step.

Example 1E 5-isocyanatoisoquinoline

Phosgene (20 ml, 20% in toluene from Fluka) in CH$_2$Cl$_2$ (300 mL) at 0° C. was treated with DMAP (10 g) in CH$_2$Cl$_2$ (100 mL) slowly. After complete addition, the mixture was treated with 5-aminoisoquinoline (5 g) in CH$_2$Cl$_2$ (100 mL) dropwise. The mixture was allowed to warm to room temperature and then stirred overnight. The solvent was removed under reduced pressure. The solid residue was extracted with diethyl ether (400 mL). The diethyl ether was filtered to provide the title compound in diethyl ether as a pale yellow solution. The diethyl ether solution was used in subsequent reactions without further purification.

Example 1F

N-(5-tert-butyl-2,3-dihydro-1H-inden-1-yl)-N'-5-isoquinolinylurea 5-tert-Butyl-2,3-dihydro-1H-inden-1-ylamine (150 mg, 1.13 mmol) in diethyl ether (10 mL) was treated with 5-isocyanatoisoquinoline in diethyl ether. The mixture was stirred for 2 hours, filtered, and the filter cake was washed with diethyl ether to provide the title compound. NMR (DMSO-d$_6$) 1.29 (s, 9H), 1.78-1.90 (m, 1H), 2.43-2.54 (m, 1H, buried under DMSO), 2.76-3.05 (m, 2H), 5.19 (m, 1H), 7.27 (m, 2H), 7.31 (m, 1H), 7.43 (d, 1H), 7.89 (t, 1H), 8.05 (d, 1H), 8.63 (d, 1H), 8.69 (d, 1H), 9.33 (s, 1H), 9.73 (s, 1H); MS (ESI+) 360 (M+H)$^+$; Elemental: Calculated for C$_{23}$H$_{25}$N$_3$O.HCl.0.5H$_2$O: C, 68.22; H, 6.72; N, 10.38. Found: C, 68.31; H, 6.81; N, 10.16.

Example 2

N-(5-tert-butyl-2,3-dihydro-1H-inden-1-yl)-N'-(3-methyl-5-isoquinolinyl)urea

Example 2A 5-isocyanato-3-methylisoquinoline

The title compound was prepared using the procedure described in Example 1E using 3-methyl-5-isoquinolinamine instead of 5-aminoisoquinoline.

Example 2B

N-(5-tert-butyl-2,3-dihydro-1H-inden-1-yl)-N'-(3-methyl-5-isoquinolinyl)urea

The title compound was prepared using the procedure described in Example 1F using 5-isocyanato-3-methylisoquinoline instead of 5-isocyanatoisoquinoline. NMR (DMSO-d$_6$) 1.29 (s, 9H), 1.78-1.91 (m, 1H), 2.43-2.53 (m, 1H, buried under DMSO), 2.75 (s, 3H), 2.79-2.87 (m, 1H), 2.91-3.02 (m, 1H), 5.19 (m, 1H), 7.29 (m, 4H), 7.80 (t, 1H), 7.97 (d, 1H), 8.40 (s, 1H), 8.61 (d, 1H), 9.13 (s, 1H), 9.64 (s, 1H); MS (ESI+) 374 (M+H)$^+$; Elemental: Calculated for C$_{24}$H$_{27}$N$_3$O.HCl.0.8H$_2$O: C, 67.93, H, 7.03; N, 9.90. Found: C, 67.85; H, 7.06; N, 9.66.

Example 3

(+)N-(5-tert-butyl-2,3-dihydro-1H-inden-1-yl)-N'-(3-methyl-5-isoquinolinyl)urea

Racemic N-(5-tert-butyl-2,3-dihydro-1H-inden-1-yl)-N'-(3-methyl-5-isoquinolinyl)urea was resolved by chiral HPLC using a Chiralcel OD, 20 micron, 5 cm ID×25 cm column with a mobile phase of hexanes (with 0.1% DEA)/ethanol at a 90/10 to 92/8 ratio. The flow rate was 50 ml/min and the sample loading was 100-200 mg per run. [α]$_D$+14.4° (c 1.0; MeOH); NMR (DMSO-d$_6$) 1.29 (s, 9H), 1.78-1.91 (m, 1H), 2.43-2.53 (m, 1H, buried under DMSO), 2.75 (s, 3H), 2.79-2.87 (m, 1H), 2.91-3.02 (m, 1H), 5.19 (m, 1H), 7.29 (m, 4H), 7.80 (t, 1H), 7.97 (d, 1H), 8.40 (s, 1H), 8.61 (d, 1H), 9.13 (s, 1H), 9.64 (s, 1H); MS (ESI+) 374 (M+H)$^+$; Elemental: Calculated for C$_{24}$H$_{27}$N$_3$O.HCl.0.9H$_2$O: C, 67.64; H, 7.05; N, 9.86. Found: C, 67.77; H, 7.12; N, 9.77.

Example 4

(−)N-(5-tert-butyl-2,3-dihydro-1H-inden-1-yl)-N'-(3-methyl-5-isoquinolinyl)urea

The title compound was obtained using chiral HPLC as described in Example 3. [α]$_D$−15.3° (c 0.89; MeOH); NMR (DMSO-d$_6$) 1.29 (s, 9H), 1.78-1.91 (m, 1H), 2.43-2.53 (m, 1H, buried under DMSO), 2.75 (s, 3H), 2.79-2.87 (m, 1H), 2.91-3.02 (m, 1H), 5.19 (m, 1H), 7.29 (m, 4H), 7.80 (t, 1H), 7.97 (d, 1H), 8.40 (s, 1H), 8.61 (d, 1H), 9.13 (s, 1H), 9.64 (s, 1H); MS (ESI+) 374 (M+H)$^+$; Elemental: Calculated for C$_{24}$H$_{27}$N$_3$O.HCl.H$_2$O: C, 67.36; H, 7.07; N, 9.82. Found: C, 67.29; H, 7.20; N, 9.91.

Example 5

(−)N-(5-tert-butyl-2,3-dihydro-1H-inden-1-yl)-N'-5-isoquinolinylurea

Racemic N-(5-tert-butyl-2,3-dihydro-1H-inden-1-yl)-N'-5-isoquinolinylurea was resolved by chiral HPLC using a Chiralcel OD, 20 micron, 5 cm ID×25 cm column with a mobile phase of hexanes (with 0.1% DEA)/ethanol at a 90/10 to 92/8 ratio, the flow rate was 50 ml/minutes. [α]$_D$−29.4° (c 0.89; MeOH); NMR (DMSO-d$_6$) 1.06 (t, 0.3H (EtOH)), 1.29 (s, 9H), 1.78-1.90 (m, 1H), 2.43-2.54 (m, 1H, buried under DMSO), 2.76-3.05 (m, 2H), 3.44 (q, 0.2H (EtOH)), 5.19 (m, 1H), 7.27 (m, 2H), 7.31 (m, 1H), 7.43 (d, 1H), 7.89 (t, 1H), 8.05 (d, 1H), 8.63 (d, 1H), 8.69 (d, 1H), 9.33 (s, 1H), 9.73 (s, 1H); MS (ESI+) 360 (M+H)$^+$; Elemental: Calculated for C$_{23}$H$_{25}$N$_3$O.HCl.0.4H$_2$O0.1EtOH: C, 68.34; H, 6.77; N, 10.31. Found: C, 68.44; H, 6.77, N, 10.30.

Example 6

(+)N-(5-tert-butyl-2,3-dihydro-1H-inden-1-yl)-N'-5-isoquinolinylurea

Racemic N-(5-tert-butyl-2,3-dihydro-1H-inden-1-yl)-N'-5-isoquinolinylurea was resolved by chiral HPLC using a Chiralcel OD, 20 micron, 5 cm ID×25 cm column with a mobile phase of hexanes (with 0.1% DEA)/ethanol at a 90/10 to 92/8 ratio, the flow rate was 50 ml/minutes. [α]$_D$+33.3° (c 0.84; MeOH); NMR (DMSO-d$_6$) 1.06 (t, 0.6H (EtOH)), 1.29 (s, 9H), 1.78-1.90 (m, 1H), 2.43-2.54 (m, 1H, buried under DMSO), 2.76-3.05 (m, 2H), 3.44 (q, 0.4H (EtOH)), 5.19 (m, 1H), 7.27 (m, 2H), 7.31 (m, 1H), 7.43 (d, 1H), 7.89 (t, 1H), 8.05 (d, 1H), 8.63 (d, 1H), 8.69 (d, 1H), 9.33 (s, 1H), 9.73 (s, 1H); MS (ESI+) 360 (M+H)$^+$; Elemental: Calculated for C$_{23}$H$_{25}$N$_3$O.HCl.0.2H$_2$O.0.2EtOH: C, 68.76; H, 6.81; N, 10.28. Found: C, 68.69; H, 6.83; N, 10.27.

Example 7

N-(5-bromo-2,3-dihydro-1H-inden-1-yl)-N'-5-isoquinolinylurea

Example 7A 5-bromo-1-indanone O-methyloxime

5-Bromo-1-indanone and O-methylhydroxylamine hydrochloride were combined in pyridine and stirred at ambient temperature for 16 hours. The mixture was concentrated under reduced pressure and the residue was suspended in diethyl ether. The suspension was filtered and the filter cake was washed with diethyl ether. The filtrate was washed with water, 1N HCl, water, and concentrated to provide the title compound. $^1$H NMR (300 MHz, d$_6$-DMSO) 7.63 (m, 2H), 7.48 (m, 2H), 3.90 (s, 3H), 3.00 (m, 2H), 2.80 (m, 2H); MS (DCI/NH$_3$) m/e 240 (M+H)$^+$.

Example 7B 5-bromo-1-indanamine

The title compound was prepared using 5-bromo-1-indanone O-methyloxime and the procedure described in Synthesis, 995-996 (1988).

Example 7C

N-(5-bromo-2,3-dihydro-1H-inden-1-yl)-N'-5-isoquinolinylurea

The title compound was prepared using the procedure described in Example 1F using 5-bromo-1-indanamine instead of 5-tert-butyl-2,3-dihydro-1H-inden-1-ylamine. $^1$H NMR (300 MHz, d$_6$-DMSO) 9.80 (s, 1H), 9.52 (s, 1H), 8.72 (m, 3H), 8.08 (d, 1H), 7.90 (t, 1H), 7.67 (d, 1H), 7.49 (m, 1H), 7.40 (m, 1H), 7.31 (d, 1H), 5.20 (m, 1H), 3.02-2.80 (m, 3H), 1.83 (m, 1H); MS (DCI/NH$_3$) m/e 382 (M+H)$^+$; Anal. Calcd. For C$_{19}$H$_{16}$N$_3$OBr. 1.0HCl. 1.5H$_2$O: C, 51.20; H, 4.52; N, 9.43. Found: C, 51.21; H, 4.18; N, 8.90.

Example 8 methyl 4-({[(5-tert-butyl-2,3-dihydro-1H-inden-1-yl)amino]carbonyl}amino)-1H-indazole-1-carboxylate

Example 8A 4-nitro-1H-indazole

2-Methyl-3-nitroaniline (20 g) in acetic acid (~200 mL) was treated with NaNO$_2$ (20 g) in water (50 mL) at 4° C. (mechanical stirring). The reaction mixture was allowed to warm to room temperature and stir overnight. The solvent was removed under reduced pressure. The residue was treated with water (700 mL) and the mixture was filtered. The solid was dried at 45° C. in a vacuum oven overnight to provide the title compound. $^1$H NMR (DMSO) δ 8.56 (s, 1H), 8.2-8.05 (dd, 2H), 7.6 (t, 1H).

Alternatively, to a 4-necked 5-L jacketed round bottom flask fitted with a mechanical stirrer and a thermocouple was charged the nitroaniline (100 g, 1.0 equiv.) and acetic acid (2000 mL). The solution was cooled to 14° C. A chilled to ~1° C. (ice-water bath) solution of sodium nitrite (100 g, 2.2 equiv.) in water (250 mL) was added quickly in one portion. The internal temperature rose from 14° C. to 27.6° C. over 5 min., stayed at this temperature for 5 min. before gradually cooling to 15° C. The mixture was stirred for 24 h after which it was concentrated in vacuo to an approximate volume of 500 mL. The residue was reslurried in water (1800 mL) at ambient temperature for 21 hours. The orange solid was filtered, washed with water (3×250 mL), and dried in a vacuum oven at 70° C. to afford 97.0 g of 4-nitroindazole as a bright orange solid.

Example 8B methyl 4-nitro-1H-indazole-1-carboxylate

NaH (0.3 g, 12.5 mmol) in DMF (5 mL) was treated with 4-nitro-1H-indazole (1.33 g, 10 mmol) at 0° C. The reaction mixture was allowed to warm to room temperature and stir for 1 hour. The mixture was treated with methyl chloroformate (0.9 mL) and stirred at room temperature for 3 hours. The mixture was treated with water and filtered to provide the title compound as a solid. $^1$H NMR (300 MHz, DMSO-d$_6$) δ 4.19 (s, 3H), 7.9 (t, 1H), 8.38 (d, 1H), 8.62 (d, 1H), 8.85 (s, 1H).

Alternatively, to a 3-necked 2-L jacketed flask fitted with a mechanical stirrer, a thermocouple, and an addition funnel was charged 95.2 g of 4-nitroindazole and DMF (650 mL). The dark solution was cooled to 10° C. and DBU (96.0 g, 1.1 equiv.) was added via addition funnel so that the internal temperature did not go beyond 15° C. After cooling the mixture back to 10° C., methyl chloroformate (108.5 g, 2.0 equiv.) was added via addition funnel so that the internal temperature did not go beyond 25° C. After 1 hour stirring at 10° C., aqueous 10% potassium phosphate diacid in water (500 mL) was added and the mixture was stirred for 15 hours. The resulting brown solid was filtered and the reaction vessel rinsed with aqueous 10% potassium phosphate diacid in water (2×150 mL). The rinses were added to the solid on the filter. The resulting solid was washed with aqueous 10% potassium phosphate diacid in water (2×200 mL), water (2×200 mL), dried in a vacuum oven at 70° C. to afford 122.2 g of a dark brown solid. The solid was reslurried in IPAc (2000 mL) for 2 hours. The solid was filtered, washed with fresh IPAc (2×250 mL), and dried in a vacuum oven at 70° C. to afford 110.2 g of 4-nitroindazole-1-carboxylic acid methyl ester as a light brown solid.

Example 8C methyl 4-amino-1H-indazole-1-carboxylate

Methyl 4-nitro-1H-indazole-1-carboxylate 1.66 g, 7.5 mmol) and 10% Pd/C were combined in ethanol (20 mL) and exposed to a hydrogen atmosphere. The reaction mixture was heated at 80° C. for 20 minutes, allowed to cool to room temperature, and filtered through Celite. The filtrate was evaporated to provide title compound. $^1$H NMR (300 MHz, DMSO-d$_6$) δ 6.1 (s, 2H), 6.41 (dd, 1H), 7.21 (m, 2H), 8.42 (s, 1H).

Alternatively, to the reaction vessel was charged the nitroindazole carbamate, MeOH (2000 mL), and 5% Pd/C (10.6 g). The mixture was pressured with H$_2$ (40 psi) and shaken at ambient temperature. The reaction was completed in 1.5 hours. The mixture was filtered to obtain the product in MeOH. Conc., 37% HCl (100 mL) was added to the reaction mixture. The product solution was concentrated to furnish a light brown solid. The solid was reslurried in IPA (200 mL) for 15 minutes. The solid was filtered and washed with fresh IPA (3×50 mL), and dried in a vacuum oven to provide 94.9 g of 4-aminoindazole-1-carboxylic acid methyl ester, HCl salt as a light brown solid.

Example 8D methyl 4-({[(5-tert-butyl-2,3-dihydro-1H-inden-1-yl) amino]carbonyl}amino)-1H-indazole-1-carboxylate Methyl 4-amino-1H-indazole-1-carboxylate (4.59 g, 24 mmol) in toluene (800 ml) was treated with phosgene (20% in toluene, 25.4 ml, 48 mmol). The mixture was heated at reflux for 3 hours, cooled, and the solvent removed under vacuum. The residue in diethyl ether (800 ml) and triethyl amine (20 ml) was filtered and then treated with 5-tert-butyl-2,3-dihydro-1H-inden-1-ylamine (20 mmol, free base prepared from 4.52 g of the HCl salt). After stirring at ambient temperature for 16 hours, the solvent was removed under vacuum and the residue triturated with a 1:1 mixture of diethyl ether and hexanes to provide the title compound. $^1$H NMR (DMSO-d$_6$) δ 1.28 (s, 9H), 1.78-1.91 (m, 1H), 2.39-2.48 (m, 1H), 2.75-2.88 (m, 1H), 2.91-3.02 (m, 1H), 4.04 (s, 3H), 5.17 (m, 1H), 6.73 (d, 1H), 7.27 (s, 2H), 7.30 (m, 1H), 7.50 (m, 1H), 7.69 (d, 1H), 7.88 (d, 1H), 8.41 (s, 1H), 8.87 (s, 1H); MS (ESI+): 407 (M+H)$^+$; Elemental: Calculated for C$_{23}$H$_{26}$N$_4$O$_3$.0.35Et$_2$O.0.15toluene: C, 68.50; H, 6.93; N, 12.56. Found: C, 68.42; H, 6.66; N, 12.42.

Example 9

N-(5-tert-butyl-2,3-dihydro-1H-inden-1-yl)-N'-1H-indazol-4-ylurea

Methyl 4-({[(5-tert-butyl-2,3-dihydro-1H-inden-1-yl) amino]carbonyl}amino)-1H-indazole-1-carboxylate (5.67 g, 14 mmol) in tetrahydrofuran (20 ml) was treated with A 5M solution of sodium hydroxide in methanol (8 ml, 40 mmol). After stirring for 30 minutes, the reaction mixture was diluted with water and filtered. The solid was air-dried and then treated with ethanolic HCl to provide the title compound as the hydrochloride salt. $^1$H NMR (DMSO-d$_6$) δ 1.06 (t, 1.8H, EtOH), 1.27 (s, 9H), 1.75-1.88 (m, 1H), 2.40-2.48 (m, 1H), 2.76-2.88 (m, 1H), 2.90-3.01 (m, 1H), 3.44 (q, 1.2H, EtOH), 5.12 (m, 1H), 6.84 (br d, 1H), 7.05 (d, 1H), 7.20, (m, 1H), 7.26 (s, 2H), 7.31 (s, 1H), 7.69 (d, 1H), 8.10 (s, 1H), 8.70 (s, 1H); MS (ESI+): 349 (M+H)$^+$; Elemental: Calculated for C$_{21}$H$_{24}$N$_4$O.HCl.0.6EtOH0.6H$_2$O: C, 62.98; H, 7.09; N, 13.23. Found: C, 63.09; H, 6.97; N, 13.18.

Example 10 methyl 4-[({[(1S)-5-tert-butyl-2,3-dihydro-1H-inden-1-yl]amino}carbonyl)amino]-1H-indazole-1-carboxylate

Example 10A (1S)-5-tert-butyl-2,3-dihydro-1H-inden-1-ylamine 5-tert-Butyl-2,3-dihydro-1H-inden-1-ylamine (25.51 g, 93% potency), N-acetyl-(L)-leucine (23.34 g), and methanol (315 mL) were combined and heated at 65° C. for 1 hour. The solution was allowed to cool to ambient temperature. The solids were filtered and washed with toluene. The solid was then resuspended in methanol (125 mL) and brought to reflux. The solution was allowed to cool to ambient temperature and the solids were filtered. The solid was dried at 40° C. under reduced pressure to provide the title compound (98.7% ee).

Example 10B methyl 4-[({[(1S)-5-tert-butyl-2,3-dihydro-1H-inden-1-yl]amino}carbonyl)amino]-1H-indazole-1-carboxylate The title compound was prepared using the procedure in Example 8D, except using (1S)-5-tert-butyl-2,3-dihydro-1H- inden-1-ylamine (free base prepared from the N-acetyl-(L)-Leucine salt), instead of 5-tert-butyl-2,3-dihydro-1H-inden-1-ylamine.

$^1$H NMR (DMSO-d$_6$) δ 1.28 (s, 9H), 1.78-1.91 (m, 1H), 2.39-2.48 (m, 1H), 2.75-2.88 (m, 1H), 2.91-3.02 (m, 1H), 4.04 (s, 3H), 5.17 (m, 1H), 6.73 (d, 1H), 7.27 (s, 2H), 7.30 (m, 1H), 7.50 (m, 1H), 7.69 (d, 1H), 7.88 (d, 1H), 8.39 (s, 1H), 8.84 (s, 1H); MS (ESI+): 407 (M+H)$^+$.

Example 11 methyl 4-[({[(1R)-5-tert-butyl-2,3-dihydro-1H-inden-1-yl]amino}carbonyl)amino]-1H-indazole-1-carboxylate Example 11A (1R)-5-tert-butyl-2,3-dihydro-1H-inden-1-ylamine 5-tert-Butyl-2,3-dihydro-1H-inden-1-ylamine (11.70 g, 44.4% ee), N-acetyl-(D)-leucine (11.78 g), and methanol (120 mL) were combined and heated at 65° C. for 1 hour. The solution was allowed to cool to ambient temperature. The solids were filtered and washed with toluene. The solid was then resuspended in methanol (125 mL) and brought to reflux. The solution was allowed to cool to ambient temperature and the solids were filtered. The solid was dried at 40° C. under reduced pressure to provide the title compound (98.7% ee).

Alternative Preparation of (1R)-5-tert-butyl-2,3-dihydro-1H-inden-1-ylamine (1R)-(5-tert-butyl-indan-1-ylidene)-(1-phenyl-ethyl)-amine To a 5 L round bottom flask was added 5-tert-butyl-indan-1-one (370 g, 95% pure), toluene (3.2 L, 9 vol), (R)-methyl-benzylamine (266 mL, 1.05 equiv), and TFA (0.5 mL). The solution was heated to reflux via a Dean-Stark apparatus. The heating mantle was removed after 9.5 hrs at reflux (~5% unreacted ketone by HPLC assay). The brown imine solution was further cooled in an ice bath in preparation for the reduction step.

(1R)-(5-tert-butyl-indan-1-yl)-(1-phenyl-ethyl)-amine

A suspension of NaBH$_4$ (148.7 g, 2.0 equiv) in EtOH (3.0 L) inside a 12 L round bottom flask was cooled to <0° C. The imine solution was added via an addition funnel over ~100 minutes. The addition rate was controlled so the internal temperature did not exceed 0° C. during the addition. Ethanol (200 mL) was applied as a rinse and added to the reaction mixture. The mixture was allowed to stir at 0±5° C. The reaction was quenched after 2.75 hours by addition of water (470 mL). The bulk of the mixture was concentrated under reduced pressure to ~2.2 L. Some white solids left in the reaction vessel dissolved slowly in water (additional 200 mL).

The distillation residue was taken up in water (1 L) and EtOAc (2 L) and separated. The aqueous layer was extracted again with EtOAc (0.5 L). Bubbles were observed from the aqueous layer during the extractions. The organic layers were combined, washed with 10% NaCl (1 L), and concentrated. The residue was dissolved in toluene (1 L) and EtOAc (1 L). The product was extracted into 1 M H$_3$PO$_4$ (2×2 L). The aqueous layers were combined and washed with MTBE (1 L).

To isolate the secondary amine, the aqueous fraction was combined with MTBE (2 L) and the pH adjusted to 10 by addition of 10% K$_2$CO$_3$ (3.5 L) and 50% NaOH (225 mL). The organic layer (green) obtained was concentrated to yield 405 g of oil. The crude oil was subjected to the next step without further purification. 1H-NMR (CDCl$_3$, 400 MHz): 7.43-7.38 ppm (m, 2H), 7.35-7.28 (m, 3H), 7.25-7.19 (m, 3H), 4.14-4.06 (m, 2H), 2.92 (m, 1H), 2.69 (m, 1H), 2.21 (m, 1H), 1.70 (m, 1H), 1.37 (d, J=6.5 Hz, 3H), 1.31 (s, 9H). 13C-NMR(CDCl$_3$, 100 MHz): 150.0 ppm, 146.0, 143.1, 143.0, 128.1, 126.5, 123.3, 123.0, 121.4, 60.8, 56.7, 35.5, 34.8, 31.8, 30.7, 25.0.

Alternatively, the tosylate salt of the secondary amine may be isolated from imine reduction. 4.3 Kg of secondary amine was concentrated to produce an oil. It was redissolved in EtOAc (7.2 Kg) and added to a solution of TsOH—H$_2$O (1.25 equiv) in EtOAc (26.2 Kg). A lot of solids precipitated. The mixture was heated to ~65 C then cooled back to room temp. The salt was collected by filtration. The wetcake was washed with EtOAc (2×6.5 Kg), then dried overnight in a 40° C. vacuum oven. Yield=6.0 Kg, white solid, 88% w/w yield.

5-tert-butyl-indan-ylamine

To the reaction vessel was charged the secondary amine (380 g, 75242-165), MeOH (1900 mL), HOAc (10.5 g), water (190 mL), and 20% Pd(OH)$_2$/C (190 g). The mixture was pressured with H$_2$ (40 psi) and shaken at ambient temperature. The mixture was filtered after 6.5 hours to obtain the product in MeOH. The product solution was concentrated to furnish the acetate salt (clear oil that gradually solidified).

Crude assay yield was 212.0 g amine, 86.5% yield. The corresponding indane was observed by GC as a minor component of the product mixture, >30 to 1 aminoindane to indane. Mosher's amides were prepared from the acetate salt to determine the amine mixture as having 80.2% ee (9.1 to 1 favoring the R-amine).

The crude product was extracted into the aqueous layer by partitioning between aqueous HCl solution (~1200 mL) and organic solvents (675 mL, 2:1 IPAc/MTBE). The pH of the aqueous layer was adjusted to >11 with 6N NaOH, and the product amine was recovered with multiple CH$_2$Cl$_2$ extractions. The organic layers were combined, washed once with saturated NaCl solution (400 mL), and dried over Na$_2$SO$_4$. After removing the solvent, the oil was assayed to be 230.5 g amine by HPLC. This material was carried forward without additional purification. 1H-NMR (CD$_3$OD, 400 MHz): 7.42-7.32 ppm (m, 3H), 4.87 (bs, 3H), 4.72 (dd, J=4.8 Hz, 7.8 Hz, 1H), 4.32 (dd, J=4.2 Hz, 9.9 Hz, 1H), 3.05 (dddd, J=8.6 Hz, 9.6 Hz, 15.3 Hz, 72.5 Hz, 2H), 2.58 (m, 1H), 2.08 (m, 1H), 1.95 (s, 3H), 1.75-1.45 (m, 3H), 1.31 (s, 9H), 0.93 (dd, J=3.6 Hz, 6.2 Hz, 6H). 13C-NMR (CD$_3$OD, 100 MHz): 179.2 ppm, 171.8, 153.7, 144.8, 136.7, 125.0, 124.6, 122.7, 56.6, 54.7, 43.2, 35.7, 32.1, 31.9, 31.2, 26.4, 23.9, 22.9, 22.3.

Alternatively, the tosylate salt of the amine may be isolated as follows: The product solution from debenzylation (38.33 g 5-t-Butyl-aminoindan) was distilled under reduced pressure to ~390 mL. Toluene (460 mL) was added, then the mixture was distilled again under reduced pressure ~390 mL. The chase distillation with toluene was repeated three more times (460 mL each) to effectively reduce the levels of methanol and acetic acid. Product precipitated during these chase distillations. The product was obtained by filtration. The wetcake was washed with toluene and dried in a vacuum oven. Yield=96.4% (w/w), 99.2% pure, 99.6% ee.

Resolution of 5-tert-butyl-indan-ylamine via N—Ac-D-leucine Salt Formation

To a 5 L jacketed round bottom flask was charged N—Ac-D-leucine (232.0 g, 1.1 equiv), amine (230.5 g by assay), and MeOH (3 L). After heating the mixture to reflux, more MeOH was added in portions to dissolve all the solids. A total of 4025 mL MeOH (17.5 vol) was needed to obtain a clear solution.

The solution was cooled to ambient over 13 hours via the jacket temperature control. After stirring at room temp for at least 4 hrs, the slurry was filtered. The wetcake was washed with toluene (460 mL), then dried in a 40° C. vacuum oven for ~20 hours.

The white solid obtained was 243.9 g, 55.3% yield, 100% potent (127.4 g amine). By Mosher's amides, the material was 98.8% ee (170 to 1 favoring the R-amine). The filtrates were combined, concentrated and set aside. This material was 76.5% potent (contained 92.0 g amine), 61.5% ee (4.2 to 1 favoring the R-amine).

The white solid was dissolved in 0.5 M NaOH (1.5 L), and the amine extracted with $CH_2Cl_2$ (2 L, 2×250 mL). The organic layers were combined, dried over $Na_2SO_4$, and concentrated.

The crude amine weighed 132.56 g, 93.7% pure. This yellow oil was subjected to coupling without further purification.

N-Acetyl-D-leucine can be recovered from the aqueous layer from above (free-basing with 0.5 M NaOH). To the solution was added conc HCl until the pH reached ~1. The white solids were filtered and dried overnight in a 40° C. vacuum oven. Approximately 75 mL of conc HCl was needed to accomplish the pH adjustment. The recovered white solid was 107.97 g (93.0% w/w recovery), 95.7% PA (0.7% PA of amine). The remaining aqueous solution still contained some N—Ac-D-leucine.

Second Alternative Preparation of (1R)-5-tert-butyl-2,3-dihydro-1H-inden-1-ylamine To a 2 L 3-neck round bottom flask was charged 5-tert-butyl-indan-1-one (120.84 g), toluene (906 mL, 7.5 vol), and (R)-methylbenzylamine (165.5 mL, 2.0 equiv). The solution was heated to 110±10° C. under a slight nitrogen sweep to achieve a slow atmospheric distillation for ~22 hours. The total volume was further reduced by vacuum distillation to ~420 mL.

To a 1 L reactor was charged 5% Pd/C (14.0 g), imine solution (148 g of solution made above), and methanol (350 mL). The mixture was adjusted to ~0° C., then hydrogenated under 40 psi $H_2$ pressure overnight. To the reaction mixture was then charged glacial acetic acid (34.4 mL, 2.5 equiv). The debenzylation reaction occurred under 40 psi of $H_2$ pressure at ~40° C. When the reaction was complete, the catalyst was filtered and washed with methanol.

A solution of the product and TsOH—$H_2O$ (43.31 g, 1.0 equiv relative to product by solution assay) in a 1 L 3-necked round bottom flask was concentrated under reduced pressure to ~245 mL. The thick oil was heated to >60° C., then water (410 mL) was added slowly while maintaining the internal temperature at NLT 60° C. After mixing at ~65° C. for ~30 min, the mixture was cooled to room temperature. The crude crystals were collected by filtration, and the wetcake was washed with water (2×205 mL). The wetcake was returned to the flask along with toluene (300 mL) and methanol (3.0 mL). The mixture was heated to ~65° C. for ~30 min, then cooled back to room temperature. The desired product was isolated by filtration, and the wetcake was washed with toluene (2×100 mL). The material was dried in a 65° C. vacuum oven. Yield=77.9% (w/w), 100% ee.

Example 11B methyl 4-[({[(1R)-5-tert-butyl-2,3-dihydro-1H-inden-1-yl]amino}carbonyl)amino]-1H-indazole-1-carboxylate The title compound was prepared using the procedure in Example 8D, except using (1R)-5-tert-butyl-2,3-dihydro-1H-inden-1-ylamine (free base prepared from the N-acetyl-(D)-Leucine salt) instead of 5-tert-butyl-2,3-dihydro-1H-inden-1-ylamine.

$^1$H NMR (DMSO-$d_6$) δ 1.28 (s, 9H), 1.78-1.91 (m, 1H), 2.39-2.48 (m, 1H), 2.75-2.88 (m, 1H), 2.91-3.02 (m, 1H), 4.04 (s, 3H), 5.17 (m, 1H), 6.73 (d, 1H), 7.27 (s, 2H), 7.30 (m, 1H), 7.50 (m, 1H), 7.69 (d, 1H), 7.88 (d, 1H), 8.39 (s, 1H), 8.84 (s, 1H); MS (ESI+) 407 (M+H)$^+$; Elemental: Calculated for $C_{23}H_{26}N_4O_3$: C, 67.96; H, 6.45; N, 13.78; Found: C, 67.85; H, 6.51; N, 13.56.

Example 12

N-[(1S)-5-tert-butyl-2,3-dihydro-1H-inden-1-yl]-N'-1H-indazol-4-ylurea

The title compound was prepared using the procedure in Example 9, except using methyl 4-[({[(1S)-5-tert-butyl-2,3-dihydro-1H-inden-1-yl]amino}carbonyl)amino]-1H-indazole-1-carboxylate instead of methyl 4-[({[5-tert-butyl-2,3-dihydro-1H-inden-1-yl]amino}carbonyl)amino]-1H-indazole-1-carboxylate (Ex. 10B). $^1$H NMR (DMSO-$d_6$) δ 1.27 (s, 9H), 1.75-1.88 (m, 1H), 2.40-2.48 (m, 1H), 2.76-2.88 (m, 1H), 2.90-3.01 (m, 1H), 5.15 (m, 1H), 6.84 (br d, 1H), 7.05 (d, 1H), 7.20, (m, 1H), 7.26 (s, 2H), 7.31 (s, 1H), 7.69 (d, 1H), 8.11 (s, 1H), 8.72 (s, 1H); MS (ESI+): 349 (M+H)$^+$; Elemental: Calculated for $C_{21}H_{24}N_4O·HCl·0.17$hexane: C, 66.19; H, 6.91; N, 14.02. Found: C, 66.11; H, 6.94; N, 13.96.

Example 13

N-[(1R)-5-tert-butyl-2,3-dihydro-1H-inden-1-yl]-N'-1H-indazol-4-ylurea

The title compound was prepared using the procedure in Example 9, except using methyl 4-[({[(1R)-5-tert-butyl-2,3-dihydro-1H-inden-1-yl]amino}carbonyl)amino]-1H-indazole-1-carboxylate instead of methyl 4-[({[5-tert-butyl-2,3-dihydro-1H-inden-1-yl]amino}carbonyl)amino]-1H-indazole-1-carboxylate (Ex. 11B). $^1$H NMR (DMSO-$d_6$) δ 1.27 (s, 9H), 1.75-1.88 (m, 1H), 2.40-2.48 (m, 1H), 2.76-2.88 (m, 1H), 2.90-3.01 (m, 1H), 5.15 (m, 1H), 6.84 (br, 1H), 7.05 (d, 1H), 7.20, (m, 1H), 7.26 (s, 2H), 7.31 (s, 1H), 7.69 (d, 1H), 8.17 (s, 1H), 8.83 (s, 1H); MS (ESI+): 349 (M+H)$^+$; Elemental: Calculated for $C_{21}H_{24}N_4O·HCl$: C, 65.53; H, 6.55; N, 14.56. Found: C, 65.29; H, 6.63; N, 14.23.

Alternative Method of Preparing N-[(1R)-5-tert-butyl-2,3-dihydro-1H-inden-1-yl]-N'-1H-indazol-4-ylurea Step A 4-(2,5-dioxo-pyrrolidin-1-yloxycarbonylamino)-indazole-1-carboxylic acid methyl ester To a 3-necked 2-L flask fitted with a mechanical stirrer and a nitrogen inlet were charged the aminoindazole carbamate (94.5 g, 1.0 equiv.), N,N'-disuccinimidyl carbonate (113.8 g, 1.07 eq), and dry acetonitrile (950 mL, KF=0.06%). Pyridine (32.8 g, 1.0 eq) was added to the mixture and it was heated to 40° C. and stirred for 15 h during which time a solid precipitated. The solid was filtered, washed with fresh dry acetonitrile (3×100 mL), and dried in a vacuum oven at 40° C. to afford 130.1 g (92.9% potency adjusted) of the activated succinimidyl carbamate as a light brown solid.

Step B (1R)-4-[3-(5-tert-butyl-indan-1-yl)-ureido]-indazole-1-carboxylic acid methyl ester Indazole succinimidylcarbamate (33 g, 0.1 mol) was added in 2 portions (over 5 min) to a solution of indanylamine (20.4 g, 0.105 mol, 1.05 eq) and diisopropylethylamine (13.4 g, 0.104 mol) in DMF (165 mL), which was cooled to 20° C. in a water bath under nitrogen atmosphere. An exotherm to 24° C. was observed. After ~1 hour, a clear dark brown solution was formed and the reaction was found complete by HPLC.

Step C

4-[3-(5-tert-butyl-indan-1-yl)-ureido]-indazole-1-carboxylic acid methyl ester

Sodium hydroxide solution in methanol [prepared by dissolving sodium hydroxide (4.8 g 1.2 eq) in methanol (100 mL)] was added to the solution of the penultimate urea, which was precooled to 20° C. on a water bath. After stirring for 0.5 hour, the reaction was found complete by HPLC, and the mixture was poured into water (825 mL). An exotherm to 30° C. was observed. After cooling to ambient temperature, the precipitate was filtered off and washed with (1:1) methanol/water (200 mL). The washes were slow, as the wet cake tended to absorb the solvent. The wet cake was dried under vacuum overnight at 65° C. to give 34.1 g of the material, which was assayed for 30.7 g of the product by HPLC method. The crude was dissolved in 600 mL of methanol at reflux. The solution was filtered hot and distilled to ~180 mL volume. The resulting slurry was cooled to ambient temperature, mixed for 2 hours, filtered, washed with methanol (50 mL) and dried under vacuum at 65° C. for 15 hours to provide 27.8 of the title compound (80% yield).

Example 13A

N-[(1R)-5-tert-butyl-2,3-dihydro-1H-inden-1-yl]-N'-1H-indazol-4-ylurea

The amorphous form of Example 13 was prepared by evaporating a solution of Example 13 in THF (1 g/30 mL) at ambient temperature under vacuum. Differential scanning calorimetry and X-ray diffraction results are shown in FIGS. 1 and 2, respectively.

Example 13B

N-[(1R)-5-tert-butyl-2,3-dihydro-1H-inden-1-yl]-N'-1H-indazol-4-ylurea, hydrochloride Hydrochloric acid (37% aq, 17 mg) was added to a solution of compound of Example 13 (60 mg, 0.17 mmol) in THF 4 mL. After mixing for additional 15 h the precipitate was filtered off and dried to provide 27 mg (40%) of the salt. Differential scanning calorimetry and X-ray diffraction results are shown in FIGS. 3 and 4, respectively.

Example 13C

N-[(1R)-5-tert-butyl-2,3-dihydro-1H-inden-1-yl]-N'-1H-indazol-4-ylurea, tosylate Tosylic acid monohydrate (33 mg, 0.17 mmol) was added to a solution of compound of Example 13 (60 mg, 0.17 mmol) in THF 4 mL. After mixing for additional 15 h the precipitate was filtered off and dried to provide 65 mg (73%) of the salt. Differential scanning calorimetry and X-ray diffraction results are shown in FIGS. 5 and 6, respectively.

Example 13D

N-[(1R)-5-tert-butyl-2,3-dihydro-1H-inden-1-yl]-N'-1H-indazol-4-ylurea, benzenesulfonate Benzenesulfonic acid (26 mg) was added to a solution of compound of Example 13 (60 mg, 0.17 mmol) in THF 4 mL. After mixing for additional 15 h the precipitate was filtered off and dried to provide 45 mg (52%) of the salt. Differential scanning calorimetry and X-ray diffraction results are shown in FIGS. 7 and 8, respectively.

Example 14 methyl 4-[({[5-(trifluoromethyl)-2,3-dihydro-1H-inden-1-yl]amino}carbonyl)amino]-1H-indazole-1-carboxylate The title compound was prepared using the procedure in Example 8D, except using 5-(trifluoromethyl)-2,3-dihydro-1H-inden-1-ylamine instead of 5-tert-butyl-2,3-dihydro-1H-inden-1-ylamine. $^1$H NMR (DMSO-$d_6$) δ 1.85-1.98 (m, 1H), 2.50-2.61 (m, 1H), 2.86-2.97 (m, 1H), 3.00-3.12 (m, 1H), 4.04 (s, 3H), 5.29 (m, 1H), 6.85 (d, 1H), 7.51 (m, 1H), 7.57 (m, 2H), 7.64 (s, 1H), 7.70 (d, 1H), 7.85 (d, 1H), 8.42 (s, 1H), 8.96 (s, 1H); MS (ESI+): 419 (M+H)$^+$; Elemental: Calculated for $C_{20}H_{17}N_4O_3F_3$: C, 57.42; H, 4.10; N, 13.39. Found: C, 57.44; H, 4.21; N, 13.03.

Example 15

N-1H-indazol-4-yl-N'-[5-(trifluoromethyl)-2,3-dihydro-1H-inden-1-yl]urea

The title compound was prepared using the procedure in Example 9, except using methyl 4-[({[5-(trifluoromethyl)-2,3-dihydro-1H-inden-1-yl]amino}carbonyl)amino]-1H-indazole-1-carboxylate instead of methyl 4-[({[5-tert-butyl-2,3-dihydro-1H-inden-1-yl]amino}carbonyl)amino]-1H-indazole-1-carboxylate.

$^1$H NMR (DMSO-$d_6$) δ 1.06 (t, 2.4H, EtOH), 1.82-1.94 (m, 1H), 2.52-2.60 (m, 1H), 2.85-2.97 (m, 1H), 2.98-3.10 (m, 1H), 3.44 (q, 1.6H, EtOH), 5.28 (m, 1H), 7.08 (m, 2H), 7.21

(m, 1H), 7.56 (m, 2H), 7.63 (s, 1H), 7.69 (d, 1H), 8.17 (s, 1H), 8.91 (s, 1H); MS (ESI+) 361 (M+H)$^+$; Elemental: Calculated for $C_{18}H_{15}N_4OF_3 \cdot HCl \cdot 0.8EtOH \cdot 0.1H_2O$: C, 54.06; H, 4.86; N, 12.87. Found: C, 54.02; H, 4.58; N, 12.62.

Example 16 methyl 4-({[(5-piperidin-1-yl-2,3-dihydro-1H-inden-1-yl)amino]carbonyl}amino)-1H-indazole-1-carboxylate

Example 16A 5-piperidin-1-ylindan-1-one

5-Fluoroindan-1-one (5 g, 33.3 mmol) and piperidine (8.52 g, 100 mmol, 10 ml) were dissolved in pyridine (20 ml) and heated to reflux for 3 hours. The reaction mixture was cooled, the solvent removed under vacuum, and the residue taken in diethyl ether. The ether solution was washed with 1N aqueous sodium hydroxide and with water, dried with magnesium sulfate, filtered, and the filtrate was removed under vacuum to provide the title compound which was used without further purification.
$^1$H NMR (CDCl$_3$) δ 1.67 (m, 6H), 2.63 (m, 2H), 3.02 (m, 2H), 3.40 (m, 4H), 6.78 (d, 1H), 6.86 (dd, 1H), 7.62 (d, 1H); MS (DCI) 216 (M+H)$^+$.

Example 16B 5-piperidin-1-ylindan-1-one O-methyloxime

5-Piperidin-1-ylindan-1-one (4.31 g, 20 mmol) in pyridine (20 ml) was treated with methoxyamine hydrochloride (1.84 g, 22 mmol). After stirring at ambient temperature for 40 hours, the solvent was removed under vacuum and the residue taken in water and extracted with diethyl ether. The combined organic layers were washed with water, dried with magnesium sulfate, filtered, and the filtrate was removed under vacuum to provide the title compound which was used without further purification. $^1$H NMR (CDCl$_3$) δ 1.56-1.73 (m, 6H), 2.78-2.89 (m, 1H), 2.91-3.02 (m, 1H), 3.20-3.30 (m, 2H), 3.95 (s, 3H), 6.78 (m, 1H), 6.84 (m, 1H), 7.54 (d, 1H); MS (DCI): 245 (M+H)$^+$.

Example 16C 5-piperidin-1-yl-2,3-dihydro-1H-inden-1-ylamine

5-Piperidin-1-ylindan-1-one O-methyloxime (2.95 g, 12 mmol), 10% palladium on carbon (1.45 g), and 20% ammonia in methanol (80 ml), were placed in a Parr apparatus, which was charged with hydrogen to 60 psi. The mixture was shaken for 1 hour at ambient temperature and filtered. The filtrate was removed under vacuum to provide the title compound which was used without further purification.
$^1$H NMR (CDCl$_3$) δ 1.53-1.60 (m, 2H), 1.65-1.79 (m, 4H), 2.42-2.53 (m, 1H), 2.69-2.81 (m, 1H), 2.86-2.96 (m, 1H), 3.12 (t, 4H), 4.31 (t, 1H), 6.82 (m, 2H), 7.20 (d, 1H); MS (DCI) 217 (M+H)$^+$.

Example 16D methyl 4-({[(5-piperidin-1-yl-2,3-dihydro-1H-inden-1-yl)amino]carbonyl}amino)-1H-indazole-1-carboxylate The title compound was prepared using the procedure in Example 8D, except using 5-piperidin-1-yl-2,3-dihydro-1H-inden-1-ylamine instead of 5-tert-butyl-2,3-dihydro-1H-inden-1-ylamine. $^1$H NMR (DMSO-d$_6$) δ 1.48-1.66 (m, 6H), 1.75-1.89 (m, 1H), 2.39-2.47 (m, 1H), 2.70-2.82 (m, 1H), 2.85-2.95 (m, 1H), 3.10 (m, 4H), 4.04 (s, 3H), 6.61 (d, 1H), 6.81 (m, 2H), 7.12 (d, 1H), 7.49 (m, 1H), 7.68 (d, 1H), 7.88 (d, 1H), 8.38 (s, 1H), 8.82 (s, 1H); MS (ESI+) 434 (M+H)$^+$; Elemental: Calculated for $C_{24}H_{27}N_5O_3 \cdot 0.3CH_2Cl_2$: C, 63.59; H, 6.06; N, 15.26. Found: C, 63.68; H, 6.02; N, 15.14.

Example 17

N-1H-indazol-4-yl-N'-(5-piperidin-1-yl-2,3-dihydro-1H-inden-1-yl)urea

The title compound was prepared using the procedure in Example 9, except using methyl 4-({[(5-piperidin-1-yl-2,3-dihydro-1H-inden-1-yl)amino]carbonyl}amino)-1H-indazole-1-carboxylate instead of methyl 4-[({[5-tert-butyl-2,3-dihydro-1H-inden-1-yl]amino}carbonyl)amino]-1H-indazole-1-carboxylate.
$^1$H NMR (DMSO-d$_6$) δ 1.09 (t, 1.2H, Et$_2$O), 1.40-2.20 (br m, 7H), 2.52-2.59 (m, 1H), 2.84-2.96 (m, 1H), 2.96-3.07 (m, 1H), 3.38 (q, 0.8H, Et$_2$O), 3.52 (m, 4H), 5.24 (m, 1H), 5.76 (s, 0.2H, CH$_2$Cl$_2$), 7.05 (d, 1H), 7.21 (m, 1H), 7.33 (m, 1H), 7.50 (d, 1H), 7.65-7.77 (m, 3H), 8.29 (s, 1H), 9.15 (s, 1H); MS (ESI+) 376 (M+H)$^+$; Elemental: Calculated for $C_{22}H_{25}N_5O \cdot 2HCl \cdot 0.1CH_2Cl_2 \cdot 0.2Et_2O$: C, 58.31; H, 6.24; N, 14.85. Found: C, 58.22; H, 6.54; N, 15.00.

Example 18 methyl 4-({[(5-hexahydro-1H-azepin-1-yl-2,3-dihydro-1H-inden-1-yl)amino]carbonyl}amino)-1H-indazole-1-carboxylate

Example 18A 5-hexahydro-1H-azepin-1-ylindan-1-one

5-Fluoroindan-1-one (5 g, 33.3 mmol) and azepane (9.92 g, 100 mmol) were dissolved in pyridine (20 ml) and heated at reflux for 3 hours, stirred at ambient temperature for 16 hours, and then heated at reflux for an additional 6 hours. The solvent was removed under vacuum and the residue partitioned between methylene chloride and water. The organic layer was washed with 1N aqueous sodium hydroxide, dried with magnesium sulfate, filtered, and the filtrate was concentrated under vacuum. The residue was filtered through a pad of silica gel with 1:1 ethyl acetate:hexanes, and the solvent evaporated under vacuum to provide the title compound which was used without further purification. $^1$H NMR (CDCl$_3$) δ 1.56 (m, 4H), 1.81 (m, 4H), 2.62 (m, 2H), 3.02 (m, 2H), 3.55 (t, 4H), 6.59 (d, 1H), 6.68 (dd, 1H), 7.61 (d, 1H); MS (DCI) 230 (M+H)$^+$.

Example 18B 5-hexahydro-1H-azepin-1-ylindan-1-one O-methyloxime

The title compound was prepared using the procedure in Example 16B, except using 5-hexahydro-1H-azepin-1-ylindan-1-one instead of 5-piperidin-1-ylindan-1-one. $^1$H NMR (CDCl$_3$) δ 1.55 (m, 4H), 1.79 (m, 4H), 2.77-2.88 (m, 1H), 2.92-3.00 (m, 1H), 3.48 (m, 2H), 3.94 (s, 3H), 6.55 (m, 1H), 6.61 (m, 1H), 7.51 (d, 1H) MS (DCI): 259 (M+H)$^+$.

Example 18C 5-hexahydro-1H-azepin-1-yl-2,3-dihydro-1H-inden-1-ylamine

The title compound was prepared using the procedure in Example 16C, except using 5-hexahydro-1H-azepin-1-ylindan-1-one O-methyloxime instead of 5-piperidin-1-ylindan-1-one O-methyloxime. $^1$H NMR (CDCl$_3$) δ 1.55 (m, 4H), 1.60-1.74 (m, 1H), 1.77 (m, 4H), 2.41-2.52 (m, 1H), 2.69-2.69 (m, 1H), 2.86-2.97 (m, 1H), 3.43 (t, 4H), 4.31 (t, 1H), 6.57 (m, 2H), 7.16 (d, 1H); MS (DCI) 231 (M+H)$^+$.

Example 18D methyl 4-({[(5-hexahydro-1H-azepin-1-yl-2,3-dihydro-1H-inden-1-yl)amino]carbonyl}amino)-1H-indazole-1-carboxylate The title compound was prepared using the procedure in Example 16D, except using 5-hexahydro-1H-azepin-1-yl-2,3-dihydro-1H-inden-1-ylamine instead of 5-piperidin-1-yl-2,3-dihydro-1H-inden-1-ylamine. $^1$HNMR (DMSO-d$_6$) δ 1.17 (t, 0.21H, EtOAc), 1.45 (m, 4H), 1.71 (m, 4H), 1.76-1.86 (m, 1H), 1.99 (s, 0.21H, EtOAc), 2.35-2.48 (m, 1H), 2.69-2.80 (m, 1H), 2.84-2.95 (m, 1H), 3.45 (t, 4H), 4.03 (q, 0.14H, EtOAc), 4.04 (s, 3H), 5.06 (m, 1H), 6.56 (m, 3H), 7.12 (d, 2H), 7.50 (m, 1H), 7.67 (d, 1H), 7.89 (d, 1H), 8.38 (s, 1H). 8.79 (s, 1H); MS (ESI+) 448 (M+H)$^+$; Elemental: Calculated for C$_{25}$H$_{29}$N$_5$O$_3$.0.07EtOAc: C, 66.92; H, 6.57; N, 15.44. Found: C, 66.62; H, 6.85; N, 15.70.

Example 19

N-(5-hexahydro-1H-azepin-1-yl-2,3-dihydro-1H-inden-1-yl)-N'-1H-indazol-4-ylurea

The title compound was prepared using the procedure in Example 9, except using methyl 4-({[(5-hexahydro-1H-azepin-1-yl-2,3-dihydro-1H-inden-1-yl)amino]carbonyl}amino)-1H-indazole-1-carboxylate instead of methyl 4-[({[5-tert-butyl-2,3-dihydro-1H-inden-1-yl]amino}carbonyl)amino]-1H-indazole-1-carboxylate. 1H NMR (DMSO-d$_6$) δ 1.45 (m, 4H), 1.71 (m, 4H), 1.75-1.81 (m, 1H), 2.38-2.45 (m, 1H), 2.86-2.93 (m, 1H), 3.45 (t, 4H), 5.07 (m, 1H), 6.58 (m, 3H), 7.05 (d, 1H), 7.12 (d, 1H), 7.21 (m, 1H), 7.68 (d, 1H), 8.03 (s, 1H), 8.51 (s, 1H), 12.97 (s, 1H); MS (ESI+) 390 (M+H)$^+$.

Example 20

N-1H-indazol-4-yl-N'-[(1R)-5-piperidin-1-yl-2,3-dihydro-1H-inden-1-yl]urea

The title compound was obtained from the preparative chiral separation (ChiralPak AD, Hex(0.2% diethylamine): EtOH:MeOH=8:1:1) of N-1H-indazol-4-yl-N'-(5-piperidin-1-yl-2,3-dihydro-1H-inden-1-yl)urea. $^1$H NMR (300 MHz, d$_6$-DMSO) 13.00 (broad s, 1H), 8.60 (s, 1H), 8.04 (s, 1H), 7.67 (d, 1H), 7.18 (m, 2H), 7.03 (d, 1H), 6.80 (m, 2H), 6.66 (d, 1H), 5.05 (m, 1H), 3.10 (m, 4H), 2.78 (m, 1H), 2.41 (m, 1H), 1.80 (m, 1H), 1.68-1.45 (m, 7H); MS (DCI/NH$_3$) m/e 376 (M+H)$^+$.

Example 21

N-1H-indazol-4-yl-N'-[(1S)-5-piperidin-1-yl-2,3-dihydro-1H-inden-1-yl]urea

The title compound was obtained from the preparative chiral separation (ChiralPak AD, Hex(0.2% diethylamine): EtOH:MeOH=8:1:1) of N-1H-indazol-4-yl-N'-(5-piperidin-1-yl-2,3-dihydro-1H-inden-1-yl)urea. $^1$H NMR (300 MHz, d$_6$-DMSO) δ 13.00 (broad s, 1H), 8.61 (s, 1H), 8.04 (s, 1H), 7.67 (d, 1H), 7.18 (m, 2H), 7.03 (d, 1H), 6.80 (m, 2H), 6.66 (d, 1H), 5.05 (m, 1H), 3.10 (m, 4H), 2.78 (m, 1H), 2.41 (m, 1H), 1.80 (m, 1H), 1.68-1.45 (m, 7H); MS (DCI/NH$_3$) m/e 376 (M+H)$^+$.

Example 22 isopropyl 4-({[(5-tert-butyl-2,3-dihydro-1H-inden-1-yl)amino]carbonyl}amino)-1H-indazole-1-carboxylate

Example 22A isopropyl 4-nitro-1H-indazole-1-carboxylate

The title compound was prepared using the procedure in Example 8B, except using isopropyl chloroformate instead of methyl chloroformate.

Example 22B isopropyl 4-amino-1H-indazole-1-carboxylate

The title compound was prepared using the procedure in Example 8C, except using isopropyl 4-nitro-1H-indazole-1-carboxylate instead of methyl 4-nitro-1H-indazole-1-carboxylate.

Example 22C isopropyl 4-({[(5-tert-butyl-2,3-dihydro-1H-inden-1-yl)amino]carbonyl}amino)-1H-indazole-1-carboxylate The title compound was prepared using the 4 step procedure described in Ex. 8 except using isopropyl chloroformate instead of methyl chloroformate in Ex. 8B. $^1$H NMR (300 MHz, d$_6$-DMSO) 8.82 (s, 1H), 8.40 (s, 1H), 7.90 (d, 1H), 7.68 (d, 1H), 7.50 (m, 1H), 7.29 (d, 2H), 6.67 (d, 1H), 5.20 (m, 2H), 2.92 (m, 1H), 2.83 (m, 1H), 2.41 (m, 1H), 1.84 (m, 1H), 1.40 (d, 6H), 1.30 (s, 9H); MS (DCI/NH$_3$) m/e 435 (M+H)$^+$; Anal. Calcd. For C$_{25}$H$_{30}$N$_4$O$_3$: C, 69.10; H, 6.96; N, 12.89. Found: C, 68.89; H, 6.90; N, 12.83.

Example 23 isobutyl 4-({[(5-tert-butyl-2,3-dihydro-1H-inden-1-yl)amino]carbonyl}amino)-1H-indazole-1-carboxylate

Example 23A isobutyl 4-nitro-1H-indazole-1-carboxylate

The title compound was prepared using the procedure in Example 8B, except using isobutyl chloroformate instead of methyl chloroformate.

Example 23A isobutyl 4-amino-1H-indazole-1-carboxylate

The title compound was prepared using the procedure in Example 8C, except using isobutyl 4-nitro-1H-indazole-1-carboxylate instead of methyl 4-nitro-1H-indazole-1-carboxylate.

Example 23C isobutyl 4-({[(5-tert-butyl-2,3-dihydro-1H-inden-1-yl)amino]carbonyl}amino)-1H-indazole-1-carboxylate The title compound was prepared using the 4 step procedure described in Ex. 8 except using isobutyl chloroformate instead of methyl chloroformate in Ex. 8B $^1$H NMR (300 MHz, d$_6$-DMSO) 8.82 (s, 1H), 8.40 (s, 1H), 7.90 (d, 1H), 7.68 (d, 1H), 7.50 (m, 1H), 7.29 (d, 2H), 6.70 (d, 1H), 5.19 (m, 1H), 4.23 (d, 2H), 2.88 (m, 1H), 2.80 (m, 1H), 2.41 (m, 1H), 2.10 (m, 1H), 1.84 (m, 1H), 1.40 (d, 6H), 1.27 (s, 9H), 1.00 (d, 6H); MS (DCI/NH$_3$) m/e 435 (M+H)$^+$; Anal. Calcd. For C$_{26}$H$_{32}$N$_4$O$_3$ 0.2 Et$_2$O: C, 69.47; H, 7.40; N, 12.09. Found: C, 69.49; H, 7.72; N, 12.21.

Example 24

N-(5-chloro-2,3-dihydro-1H-inden-1-yl)-N'-1H-indazol-4-ylurea

Example 24A

5-chloro-2,3-dihydro-1H-inden-1-ylamine

The title compound was made according to the conditions described in Example 57D, except using 5-chloro-1-indanone instead of 2-methyl-2-(1-oxoindan-5-yl)-propionitrile

Example 24B

N-(5-chloro-2,3-dihydro-1H-inden-1-yl)-N'-1H-indazol-4-ylurea

The title compound was made first according to the conditions described in Ex. 8D except using 5-chloro-2,3-dihydro-1H-inden-1-ylamine instead of 5-tert-butyl-2,3-dihydro-1H-inden-1-ylamine (MS 385 (M+1)). Deprotection of the product obtained by using 5M NaOH in methanol according to Ex. 9 afforded the title compound. NMR (DMSO-d$_6$): 8.92 (s, 1H), 8.20 (s, 1H), 7.68 (d, J 7.5 Hz, 1H), 7.40-7.18 (m, 6H), 7.06 (d, J 8 Hz, 2H), 5.20 (m, 1H), 3.00-2.78 (m, 3H), 1.83 (m, 1H). MS (DCI): 327 (M+1). Elemental: Calculated for C17H15N4ClO.1.0HCl.0.6H2O: C, 54.59; H, 4.63; N, 14.98. Found: C, 54.22; H, 4.42; N, 15.18.

Example 25

N-(5-fluoro-2,3-dihydro-1H-inden-1-yl)-N'-1H-indazol-4-ylurea

Example 25A

5-fluoro-2,3-dihydro-1H-inden-1-ylamine

The title compound was made according to the conditions described in Example 1C and 1D, except using 5-fluoro-1-indanone instead of 5-tert-butyl-1-indanone.

Example 25B

N-(5-fluoro-2,3-dihydro-1H-inden-1-yl)-N'-1H-indazol-4-ylurea

The title compound was made first according to the conditions described in Ex. 8D except using 5-fluoro-2,3-dihydro-1H-inden-1-ylamine instead of 5-tert-butyl-2,3-dihydro-1H-inden-1-ylamine (MS 369 (M+1)). Deprotection of the product obtained by using 5M NaOH in methanol according to Ex. 9 afforded the title compound. NMR (DMSO-d$_6$): 8.9 (s, 1H), 8.20 (s, 1H), 7.70 (d, J 7.5 Hz, 1H), 7.38 (m, 1H), 7.23-7.00 (m 5H), 5.20 (m, 1H), 3.00-2.78 (m, 3H), 1.83 (m, 1H). MS (DCI): 311 (M+1). Elemental: Calculated for C17H15N4FO.1.0HCl.0.6H2O: C, 57.10; H, 4.85; N, 15.67. Found: C, 56.90; H, 4.78; N, 15.94.

Example 26

N-(4,5-dimethoxy-2,3-dihydro-1H-inden-1-yl)-N'-1H-indazol-4-ylurea

Example 26A

4,5-Dimethoxy-2,3-dihydro-1H-inden-1-ylamine

The title compound was made according to the conditions described in Example 1C and 1D, except using 4,5-dimethoxy-1-indanone instead of 5-tert-butyl-1-indanone.

Example 26B

4-[3-(4,5-dimethoxy-indan-1-yl)-ureido]-indazole-1-carboxylic acid methyl ester The title compound was made according to the conditions described in Example 36I except using 4,5-Dimethoxy-2,3-dihydro-1H-inden-1-ylamine instead of 5-(2-methoxy-1,1-dimethyl-ethyl)-indan-1-ylamine. MS (DCI) 411 (M+1).

Example 26C

N-(4,5-dimethoxy-2,3-dihydro-1H-inden-1-yl)-N'-1H-indazol-4-ylurea

The title compound was made from 4-[3-(4,5-dimethoxy-indan-1-yl)-ureido]-indazole-1-carboxylic acid methyl ester according to the deprotection procedure by using 5M NaOH in methanol (example 9). NMR (DMSO-d$_6$): 13.0 (broad s, 1H), 8.60 (s, 1H), 8.07 (s, 1H), 7.67 (d, J 7.5 Hz, 1H), 7.20 (m, 1H), 7.04 (m, 2H), 6.92 (d, J 8 Hz, 1H), 6.65 (d, J 8 Hz, 1H), 5.15 (m, 1H), 3.78 (s, 3H), 3.76 (s, 3H), 2.92 (m, 1H), 2.80 (m, 1H), 2.43 (m, 1H), 1.82 (m, 1H). MS (DCI): 353 (M+1). Elemental: Calculated for C19H20N4O3: C, 64.76; H, 5.72; N, 15.90. Found: C, 64.41; H, 5.80; N, 16.26.

Example 27

N-1H-indazol-4-yl-N'-(5-methoxy-2,3-dihydro-1H-inden-1-yl)urea

Example 27A

5-Methoxy-2,3-dihydro-1H-inden-1-ylamine

The title compound was made according to the conditions described in Example 1C and 1D, except using 5-methoxy-1-indanone instead of 5-tert-butyl-1-indanone.

Example 27B

4-[3-(5-dimethoxy-indan-1-yl)-ureido]-indazole-1-carboxylic acid methyl ester

The title compound was made according to the conditions described in Example 36I except using 5-methoxy-2,3-dihydro-1H-inden-1-ylamine instead of 5-(2-methoxy-1,1-dimethyl-ethyl)-indan-1-ylamine. MS (DCI) 380 (M+1).

Example 27C

N-1H-indazol-4-yl-N'-(5-methoxy-2,3-dihydro-1H-inden-1-yl)urea

The title compound was made from 4-[3-(5-methoxy-indan-1-yl)-ureido]-indazole-1-carboxylic acid methyl ester according to the deprotection procedure by using 5M NaOH in methanol (example 9). NMR (DMSO-$d_6$): 13.0 (broad s, 1H), 8.60 (s, 1H), 8.07 (s, 1H), 7.67 (d, J 7.5 Hz, 1H), 7.22 (m, 2H), 7.06 (d, J 8 Hz, 1H), 6.88 (d, J 1.5 Hz, 1H), 6.80 (dd, J 1.5 and 8 Hz, 1H), 6.63 (d, J 8 Hz, 1H), 5.13 (m, 1H), 3.72 (s, 3H), 3.00-2.70 (m, 2H), 2.42 (m, 1H), 1.80 (m, 1H). MS (DCI): 323 (M+1). Elemental: Calculated for C18H18N4O2.0.2H2O: C, 66.32; H, 5.69; N, 17.19. Found: C, 65.99; H, 5.64; N, 17.84.

Example 28

N-(5,6-dimethoxy-2,3-dihydro-1H-inden-1-yl)-N'-1H-indazol-4-ylurea

Example 28A 5,6-Dimethoxy-2,3-dihydro-1H-inden-1-ylamine

The title compound was made according to the conditions described in Example 1C and 1D, except using 5,6-dimethoxy-1-indanone instead of 5-tert-butyl-1-indanone.

Example 28B

4-[3-(5,6-dimethoxy-indan-1-yl)-ureido]-indazole-1-carboxylic acid methyl ester

The title compound was made according to the conditions described in Example 36I except using 5,6-Dimethoxy-2,3-dihydro-1H-inden-1-ylamine instead of 5-(2-methoxy-1,1-dimethyl-ethyl)-indan-1-ylamine. MS (DCI) 411 (M+1).

Example 28C

N-(5,6-dimethoxy-2,3-dihydro-1H-inden-1-yl)-N'-1H-indazol-4-ylurea

The title compound was made from 4-[3-(5,6-dimethoxy-indan-1-yl)-ureido]-indazole-1-carboxylic acid methyl ester according to the deprotection procedure by using 5M NaOH in methanol (example 9). NMR (DMSO-$d_6$): 13.0 (broad s, 1H), 8.60 (s, 1H), 8.07 (s, 1H), 7.70 (d, J 7.5 Hz, 1H), 7.20 (m, 1H), 7.04 (d, J, 8 Hz, 1H), 6.92 (d, J 8 Hz, 1H), 6.65 (d, J 8 Hz, 1H), 5.17 (m, 1H), 3.78 (s, 3H), 3.76 (s, 3H), 3.00-2.70 (m, 2H), 2.43 (m, 1H), 1.80 (m, 1H). MS (DCI): 353 (M+1). Elemental: Calculated for C19H20N4O3.0.4H2O: C, 63.47; H, 5.83; N, 15.58. Found: C, 63.21; H, 5.82; N, 15.77.

Example 29

N-1H-indazol-4-yl-N'-(6-methoxy-2,3-dihydro-1H-inden-1-yl)urea

Example 29A

6-Methoxy-2,3-dihydro-1H-inden-1-ylamine

The title compound was made according to the conditions described in Example 1C and 1D, except using 6-methoxy-1-indanone instead of 5-tert-butyl-1-indanone.

Example 29B

4-[3-(6-methoxy-indan-1-yl)-ureido]-indazole-1-carboxylic acid methyl ester

The title compound was made according to the conditions described in Example 36I except using 6-methoxy-2,3-dihydro-1H-inden-1-ylamine instead of 5-(2-methoxy-1,1-dimethyl-ethyl)-indan-1-ylamine. MS (DCI) 381 (M+1).

Example 29C

N-1H-indazol-4-yl-N'-(6-methoxy-2,3-dihydro-1H-inden-1-yl)urea

The title compound was made from 4-[3-(6-methoxy-indan-1-yl)-ureido]-indazole-1-carboxylic acid methyl ester according to the deprotection procedure by using 5M NaOH in methanol (example 9). NMR (DMSO-$d_6$): 13.0 (broad s, 1H), 8.60 (s, 1H), 8.07 (s, 1H), 7.67 (d, J 7.5 Hz, 1H), 7.20 (m, 2H), 7.05 (d, J 8 Hz, 1H), 6.90 (s, 1H), 6.82 (d, J 1.5 Hz, 1H), 6.72 (dd, J 1.5 and 8 Hz, 1H), 5.18 (m, 1H), 3.72 (s, 3H), 2.95-2.68 (m, 2H), 2.42 (m, 1H), 1.82 (m, 1H). MS (DCI) 323 (M+1) Elemental: Calculated for C18H18N4O2.0.4H2O: C, 65.60; H, 5.75; N, 17.00. Found: C, 65.20; H, 5.49; N, 17.39.

Example 30

N-(1-acetyl-1H-indazol-4-yl)-N'-(5,6-dimethoxy-2,3-dihydro-1H-inden-1-yl)urea

To the solution of 1-(5,6-dimethoxy-indan-1-yl)-3-(1H-indazol-4-yl)-urea (0.1 g, 0.28 mmol) in pyridine (2 mL) was added acetyl chloride (0.5 mL) and mixture stirred for 15 hours at ambient temperature. The mixture was suspended with ethyl acetate and filtered. The precipitate was triturated with ether twice and dried to obtain 42 mg (38%) of desired product as a yellow solid. NMR (DMSO-$d_6$): 8.98 (s, 1H), 8.72 (s, 1H), 7.60 (d, J 7.5 Hz, 1H), 7.32-7.18 (m, 2H), 6.90 (d, J 8 Hz, 2H), 6.53 (d, J 8 Hz, 1H), 5.16 (m, 1H), 3.76 (s, 3H), 3.72 (s, 3H), 3.00-2.70 (m, 5H), 2.43 (m, 1H), 1.82 (m, 1H). MS (DCI): 395 (M+1). Elemental: Calculated for C18H18N4O2.0.2H2O: C, 63.37; H, 5.67; N, 14.08. Found: C, 63.07; H, 5.49; N, 13.94.

Example 31

N-(1-acetyl-1H-indazol-4-yl)-N'-[(1R)-5-tert-butyl-2,3-dihydro-1H-inden-1-yl]urea To the solution of 1-(5-tert-butyl-indan-4-yl)-3-(1H-indazol-4-yl)-urea (0.34 g, 0.98 mmol) in pyridine (3 mL) was added acetyl chloride (1.0 mL) and mixture stirred for 15 hours at ambient temperature. The reaction mixture was concentrated and chromatographed (EtOAc-hexane, 1:4) to obtain 54 mg (14%) of desired product. NMR (DMSO-$d_6$): 8.92 (s, 1H), 8.40 (s, 1H), 7.85 (m, 2H), 7.50 (m, 1H), 7.28 (m, 3H), 6.71 (d, J 8 Hz, 1H), 5.18 (m, 1H), 3.00-2.78 (m, 2H), 2.70 (s, 3H), 2.43 (m, 1H), 1.83 (m, 1H). MS (DCI): 391 (M+1). Elemental: Calculated for C18H18N4O2: C, 70.75; H, 6.71; N, 14.35. Found: C, 70.72; H, 7.11; N, 14.44.

Example 32

N-[(1S)-4,5-dimethoxy-2,3-dihydro-1H-inden-1-yl]-N'-1H-indazol-4-ylurea

The title compound was prepared by chiral separation of the corresponding racemic compound N-(4,5-dimethoxy-2,3-dihydro-1H-inden-1-yl)-N'-1H-indazol-4-ylurea (ex. 26) using a chiral column ChiralCel OD. NMR (DMSO-$d_6$): 13.0 (broad s, 1H), 8.60 (s, 1H), 8.07 (s, 1H), 7.67 (d, J 7.5 Hz, 1H), 7.20 (m, 1H), 7.04 (m, 2H), 6.92 (d, J 8 Hz, 1H), 6.65 (d, J 8 Hz, 1H), 5.15 (m, 1H), 3.78 (s, 3H), 3.76 (s, 3H), 2.92 (m, 1H), 2.80 (m, 1H), 2.43 (m, 1H), 1.82 (m, 1H). MS (DCI): 353 (M+1).

Example 33

N-[(1R)-4,5-dimethoxy-2,3-dihydro-1H-inden-1-yl]-N'-1H-indazol-4-ylurea

The title compound was prepared by chiral separation of the corresponding racemic compound N-(4,5-dimethoxy-2,3-dihydro-1H-inden-1-yl)-N'-1H-indazol-4-ylurea (ex. 26) using a chiral column ChiralCel OD. NMR (DMSO-$d_6$): 13.0 (broad s, 1H), 8.60 (s, 1H), 8.07 (s, 1H), 7.67 (d, J 7.5 Hz, 1H), 7.20 (m, 1H), 7.04 (m, 2H), 6.92 (d, J 8 Hz, 1H), 6.65 (d, J 8 Hz, 1H), 5.15 (m, 1H), 3.78 (s, 3H), 3.76 (s, 3H), 2.92 (m, 1H), 2.80 (m, 1H), 2.43 (m, 1H), 1.82 (m, 1H). MS (DCI): 353 (M+1).

Example 34

N-1H-indazol-4-yl-N'-[(1S)-5-methoxy-2,3-dihydro-1H-inden-1-yl]urea

The title compound was prepared by chiral separation of the corresponding racemic compound N-1H-indazol-4-yl-N'-(5-methoxy-2,3-dihydro-1H-inden-1-yl)urea (ex. 27) using a chiral column ChiralCel OD. NMR (DMSO-$d_6$): 13.0 (broad s, 1H), 8.60 (s, 1H), 8.07 (s, 1H), 7.67 (d, J 7.5 Hz, 1H), 7.22 (m, 2H), 7.06 (d, J 8 Hz, 1H), 6.88 (d, J 1.5 Hz, 1H), 6.80 (dd, J 1.5 and 8 Hz, 1H), 6.63 (d, J 8 Hz, 1H), 5.13 (m, 1H), 3.72 (s, 3H), 3.00-2.70 (m, 2H), 2.42 (m, 1H), 1.80 (m, 1H). MS (DCI): 323 (M+1).

Example 35

N-1H-indazol-4-yl-N'-[(1R)-5-methoxy-2,3-dihydro-1H-inden-1-yl]urea

The title compound was prepared by chiral separation of the corresponding racemic compound N-1H-indazol-4-yl-N'-(5-methoxy-2,3-dihydro-1H-inden-1-yl)urea (ex. 27) using a chiral column ChiralCel OD. NMR (DMSO-$d_6$): 13.0 (broad s, 1H), 8.60 (s, 1H), 8.07 (s, 1H), 7.67 (d, J 7.5 Hz, 1H), 7.22 (m, 2H), 7.06 (d, J 8 Hz, 1H), 6.88 (d, J 1.5 Hz, 1H), 6.80 (dd, J 1.5 and 8 Hz, 1H), 6.63 (d, J 8 Hz, 1H), 5.13 (m, 1H), 3.72 (s, 3H), 3.00-2.70 (m, 2H), 2.42 (m, 1H), 1.80 (m, 1H). MS (DCI): 323 (M+1).

Example 36

N-1H-indazol-4-yl-N'-[5-(2-methoxy-1,1-dimethyl-ethyl)-2,3-dihydro-1H-inden-1-yl]urea Example 36A (3-bromo-phenyl)-acetic acid methyl ester To a solution of 3-brophenylacetic acid (5.0 g, 23.3 mmol) in MeOH (50 mL) was added acetyl chloride (5.0 mL) and resulting solution refluxed for 2.5 h. The mixture was cooled to ambient temperature, diluted with ether and washed with water twice. Organic layer was separated and concentrated to obtain 5.4 g of the crude material as an oil. NMR (DMSO-$d_6$): 7.50 (m, 2H), 7.28 (m, 2H), 3.72 (s, 2H), 3.61 (s, 3H).

MS (DCI): 246 (M+NH$_4$).

Example 36B 2-(3-bromo-phenyl)-2-methyl-propionic acid methyl ester

To the suspension of NaH (1.65 g, 68.8 mmol, 95%) in THF (100 mL) was added dropwise crude (3-bromo-phenyl)-acetic acid methyl ester (~23.3 mmol) and after 20 min MeI (7.8 g, 55.0 mmol) was added. The milky solution was stirred for 15 h at ambient temperature and quenched with i-PrOH and H$_2$O. Resulting mixture was extracted with ether. Organic layer was washed with aq. NH$_4$Cl and water, separated and evaporated to obtain desired product (5.0 g, 85%) as an oil. NMR (DMSO-$d_6$): 7.48 (m, 2H), 7.30 (m, 2H), 3.60 (s, 3H), 1.50 (s, 6H).

MS (DCI): 274 (M+NH$_4$).

Example 36C 2-(3-bromo-phenyl)-2-methyl-propan-1-ol

To a stirred suspension of LiAlH$_4$ (0.71 g, 18.7 mmol) in THF (100 mL) was added dropwise 2-(3-bromo-phenyl)-2-methyl-propionic acid methyl ester (4.0 g, 15.6 mmol). After 2 h the mixture was quenched with i-PrOH and H$_2$O and extracted with ether. Organic layer was washed twice with water, separated and concentrated to obtain desired alcohol (3.5 g, 98%). NMR (DMSO-$d_6$): 7.52 (m, 1H), 7.38 (m, 2H), 7.24 (m, 1H), 4.72 (t, J 3.5 Hz, 1H), 3.40 (d, J 3.5 Hz, 2H), 1.10 (s, 6H). MS (DCI): 246 (M+NH$_4$).

Example 36D 1-bromo-3-(2-methoxy-1,1-dimethyl-ethyl)-benzene

To a suspension of NaH (0.22 g, 9.00 mmol, 95%) in THF (30 mL) was added dropwise at ambient temperature the solution of 2-(3-bromo-phenyl)-2-methyl-propan-1-ol (1.7 g, 7.46 mmol) in THF (10 mL). After 10 min MeI (0.8 mL, 15 mmol) was added and the mixture stirred for 3 h at ambient temperature. The mixture was diluted with ether and washed twice with water. Organic layer was separated and concentrated to obtain the desired product (1.64 g, 91%) as a clear oil. NMR (DMSO-d$_6$): 7.52 (m, 1H), 7.40 (m, 2H), 7.26 (m, 1H), 3.38 (s, 2H), 3.20 (s, 3H), 1.12 (s, 6H). MS (DCI): 260 (M+NH$_4$).

Example 36E

[3-(2-methoxy-1,1-dimethyl-ethyl)-phenylethynyl]-trimethyl-silane

To a solution of 1-bromo-3-(2-methoxy-1,1-dimethyl-ethyl)-benzene (1.62 g, 6.69 mmol) and trimethylsilylacetylene (1.2 mL, 8.7 mmol, 1.3 eq.) in MeCN-Et3N (50 mL, 7:3) was added Pd(PPh3)2Cl2 (0.23 g, 0.33 mmol. 0.05 eq.), CuI (0.038 g, 0.2 mmol, 0.03 eq.) and the mixture refluxed for 16 h. After cooling to ambient temperature and concentration under reduced pressure the residue was chromatographed (EtOAc-hexane, 2:98) to obtain 1.54 g (89%) of the desired product. NMR (DMSO-d$_6$): 7.28-7.00 (m, 4H), 3.16 (s, 2H), 2.98 (s, 3H), 1.00 (s, 6H), 0.1 (s, 9H). MS (DCI): 261 (M+1).

Example 36F 5-(2-methoxy-1,1-dimethyl-ethyl)-indan-1-one

The title compound was prepared by cyclocarbonylation procedure described in Ex. 57C except using [3-(2-methoxy-1,1-dimethyl-ethyl)-phenylethynyl]-trimethyl-silane instead of 2-methyl-2-(3-trimethylsilanylethynylphenyl)-propionitrile NMR (DMSO-d$_6$): 7.58 (m, 2H), 7.43 (m, 1H), 3.42 (s, 2H), 3.20 (s, 3H), 3.09 (m, 2H), 2.60 (m, 2H), 1.24 (s, 6H). MS (DCI): 219 (M+1).

Example 36G 5-(2-methoxy-1,1-dimethyl-ethyl)-indan-1-ylamine

The title compound was made according to the conditions described in Example 1C and 1D, except using 5-(2-methoxy-1,1-dimethyl-ethyl)-indan-1-one instead of 5-tert-butyl-1-indanone. NMR (DMSO-d$_6$): 7.26-7.11 (m, 3H), 4.18 (t, J 7.5 Hz, 1H), 3.31 (s, 2H), 3.20 (s, 3H), 2.80 (m, 1H), 2.66 (m, 1H), 2.30 (m, 1H), 1.55 (m, 1H), 1.11 (s, 6H).
MS (DCI): 220 (M+1).

Example 36H 4-(2,5-dioxo-pyrrolidin-1-yloxycarbonylamino)-indazole-1-carboxylic acid methyl ester 4-Amino-indazole-1-carboxylic acid methyl ester (1.9 g, 10 mmol) and disuccinimidylcarbonate (2.8 g, 11 mmol) were mixed in MeCN (100 mL) for 48 hours under nitrogen atmosphere. The solid was filtered off, washed with MeCN (10 mL) and dried under vacuum at ambient temperature to give desired product (2.56 g, 77%) as off-white solid.

Example 36I

4-{3-[5-(2-methoxy-1,1-dimethyl-ethyl)-indan-1-yl]-ureido}-indazole-1-carboxylic acid methyl ester 4-(2,5-dioxo-pyrrolidin-1-yloxycarbonylamino)-indazole-1-carboxylic acid methyl ester (0.66 g, 2.00 mmol) was added to a solution of 5-(2-methoxy-1,1-dimethyl-ethyl)-indan-1-ylamine (0.46 g, 2.1 mmol) and diisopropylethylamine (0.26 g, 2.00 mmol) in DMF (6 mL) under nitrogen atmosphere at ambient temperature. After 30 minutes the mixture was diluted with water (6 mL). The resulting precipitate was filtered off, washed with aqueous MeCN twice and dried to obtain desired product (0.48 g, 55%). NMR (DMSO-d$_6$): 8.82 (s, 1H), 8.40 (s, 1H), 7.95 (s, 1H), 7.88 (d, J 7.5 Hz, 1H), 7.69 (d, J 8 Hz, 1H), 7.52 (t, J 8 Hz, 1H), 7.24 (m, 2H), 6.70 (d, J 7.5 Hz, 1H), 5.18 (m, 1H), 4.02 (m, 3H), 3.38 (s, 2H), 3.20 (s, 3H), 3.10-2.72 (m, 2H), 2.42 (m, 1H), 1.83 (m, 1H), 1.14 (s, 6H). MS (DCI): 437 (M+1).

Example 36

N-1H-indazol-4-yl-N'-[5-(2-methoxy-1,1-dimethyl-ethyl)-2,3-dihydro-1H-inden-1-yl]urea The title compound was made according to the conditions described in Example 9, substituting 4-{3-[5-(2-methoxy-1,1-dimethyl-ethyl)-indan-1-yl]-ureido}-indazole-1-carboxylic acid methyl ester for N-(5-tert-butyl-2,3-dihydro-1H-inden-1-yl)-N'-1H-indazol-4-ylurea. NMR (DMSO-d$_6$): 13.0 (broad s, 1H), 8.58 (s, 1H), 8.02 (s, 1H), 7.68 (d, J 7.5 Hz, 1H), 7.23 (m, 4H), 7.08 (d, J 8 Hz, 1H), 6.70 (d, J 8 Hz, 1H), 5.19 (m, 1H), 3.38 (s, 2H), 3.20 (s, 3H), 3.01-2.70 (m, 2H), 2.42 (m, 1H), 1.82 (m, 1H), 1.23 (s, 6H). MS (DCI): 379 (M+1).

Example 37

N-[5-(2-hydroxy-1,1-dimethylethyl)-2,3-dihydro-1H-inden-1-yl]-N'-1H-indazol-4-ylurea The title compound was prepared by procedure described in Example 36, substituting 1-bromo-3-(2-tert-butyl-dimethylsilyl-1,1-dimethyl-ethyl)-benzene for 1-bromo-3-(2-methoxy-1,1-dimethyl-ethyl)-benzene. Deprotection by using 5M NaOH in methanol (example 9) afforded title compound. NMR (DMSO-d$_6$): 8.80 (broad s, 1H), 8.08 (s, 1H), 7.70 (d, J 7.5 Hz, 1H), 7.23 (m, 4H), 7.06 (d, J 8 Hz, 1H), 6.86 (d, J 8 Hz, 1H), 5.18 (m, 1H), 3.40 (s, 2H), 3.00-2.73 (m, 2H), 2.41 (m, 1H), 1.80 (m, 1H), 1.10 (s, 6H). MS (DCI): 365 (M+1).

Example 38

N-6,7-dihydro-5H-cyclopenta[b]pyridin-7-yl-N'-1H-indazol-4-ylurea

Example 38A 6,7-Dihydro-5H-[1]pyrindin-7-ylamine

The title compound was made according to the conditions described in Example 1C and 1D, except using 5,6-dihydro-[1]pyridin-7-one (*J. Org. Chem.* Vol 49, page 2208 (1984)) instead of 5-tert-butyl-1-indanone.

Example 38B

4-[3-(6,7-Dihydro-5H-[1]pyrindin-7-yl)-ureido]indazole-1-carboxylic acid methyl ester The title compound was made according to the conditions described in Example 36I except using 6,7-Dihydro-5H-[1]pyrindin-7-ylamine-instead of 5-(2-methoxy-1,1-dimethyl-ethyl)-indan-1-ylamine. MS (DCI) 352 (M+1).

Example 38C

N-6,7-dihydro-5H-cyclopenta[b]pyridin-7-yl-N'-1H-indazol-4-ylurea

The title compound was made from 4-[3-(6,7-Dihydro-5H-[1]pyrindin-7-yl)-ureido]indazole-1-carboxylic acid methyl ester according to the deprotection procedure by using 5M NaOH in methanol (example 9). NMR (DMSO-$d_6$): 13.0 (s, 1H), 8.80 (s, 1H), 8.40 (m, 1H), 8.02 (s, 1H), 7.70 (m, 2H), 7.30-6.80 (m, 4H), 5.04 (m, 1H), 3.02-2.58 (m, 3H), 1.82 (m, 1H). MS (DCI): 294 (M+1). Elemental: Calculated for C16H15N5O.1.5H2O: C, 59.99; H, 5.66; N, 21.86. Found: C, 60.06; H, 5.12; N, 21.49.

Example 39

N-(5-tert-butyl-2-fluoro-2,3-dihydro-1H-inden-1-yl)-N'-1H-indazol-4-ylurea

Example 39A 5-tert-Butyl-2-fluoro-indan-1-one 5-tert-butyl-indan-1-one (7.53 g, 40 mmol) was dissolved in methanol (400 ml). Accufluor (32.18 g) was added, and the reaction heated to reflux for 2 hours. After cooling and removing the solvent under vacuum, the residue was taken in methylene chloride and filtered. The filtrate was washed with water, dried with magnesium sulfate, and filtered, and the solvent removed under vacuum to give 5-tert-Butyl-2-fluoro-indan-1-one, which was used without further purification. $^1$H NMR (300 MHz, CDCl$_3$) 7.73 (d, 1H), 7.48 (d, 1H), 7.45 (s, 1H), 5.18-5.35 (m, 1H), 3.54-3.65 (m, 1H), 3.12-3.29 (m, 1H), 1.36 (s, 9H). MS (CSI) m/e 224 (M+NH$_4$)$^+$ Example 39B 5-tert-Butyl-2-fluoro-indan-1-ylamine The title compound was made according to the conditions described in Example 57D, except using 5-tert-Butyl-2-fluoro-indan-1-one instead of 2-methyl-2-(1-oxoindan-5-yl)-propionitrile. $^1$H NMR (300 MHz, CDCl$_3$) 7.24-7.37 (m, 3H), 4.83-5.29 (m, 1H, 2 diastereomers), 4.27-4.46 (m, 1H, 2 diastereomers), 2.97-3.37 (m, 2H), 1.20-1.34 (m, 9H, 2 diastereomers+rotomers)
MS (CSI) m/e 208 (M+H)$^+$ Example 39C 4-[3-(5-tert-Butyl-2-fluoro-indan-1-yl)-ureido]-indazole-1-carboxylic acid methyl ester The title compound was made according to the conditions described in Example 36I except using 5-tert-Butyl-2-fluoro-indan-1-ylamine instead of 5-(2-methoxy-1,1-dimethyl-ethyl)-indan-1-ylamine. MS (DCI) 425 (M+1).

Example 39

N-(5-tert-butyl-2-fluoro-2,3-dihydro-1H-inden-1-yl)-N'-1H-indazol-4-ylurea

The title compound was made from 4-[3-(5-tert-Butyl-2-fluoro-indan-1-yl)-ureido]-indazole-1-carboxylic acid methyl ester according to the deprotection procedure by using 5M NaOH in methanol (example 9). $^1$H NMR (300 MHz, d$_6$-DMSO) [shows two diastereomers]
MS (DCI/NH$_3$) m/e 367 (M+H)$^+$. Anal. Calcd. For C$_{21}$H$_{23}$FN$_4$O.1.6H$_2$O: C, 63.81; H, 6.68; N, 14.17. Found: C, 63.93; H, 6.79; N, 14.00.

Example 40

N-[(1R,2S)-5-tert-butyl-2-fluoro-2,3-dihydro-1H-inden-1-yl]-N'-1H-indazol-4-ylurea The title compound was prepared by chiral separation of the corresponding racemic compound N-(5-tert-butyl-2-fluoro-2,3-dihydro-1H-inden-1-yl)-N'-1H-indazol-4-ylurea (Ex. 39) using a chiral column ChiralCel OD. $^1$H NMR (300 MHz, d$_6$-DMSO) 13.01 (broad s, 1H), 8.87 (s, 1H), 8.08 (s, 1H), 7.71 (d, 1H), 7.33 (s, 1H), 7.30 (d, 1H), 7.21 (m, 2H), 7.09 (d, 1H), 6.87 (d, 1H), 5.33-5.46 (m, 2H), 3.05-3.27 (m, 2H), 1.27 (s, 9H). MS (DCI/NH$_3$) m/e 367 (M+H)$^+$. [α]$_D$–32.75° (c=0.800, 1:1 MeOH:CH$_2$Cl$_2$). Structure is cis by ROESY NMR, absolute stereochemistry assigned arbitrarily.

Example 41

N-[(1S,2S)-5-tert-butyl-2-fluoro-2,3-dihydro-1H-inden-1-yl]-N'-1H-indazol-4-ylurea The title compound was prepared by chiral separation of the corresponding racemic compound N-(5-tert-butyl-2-fluoro-2,3-dihydro-1H-inden-1-yl)-N'-1H-indazol-4-ylurea (Ex. 39) using a chiral column ChiralCel OD. $^1$H NMR (300 MHz, d$_6$-DMSO) 13.01 (broad s, 1H), 8.87 (s, 1H), 8.08 (s, 1H), 7.71 (d, 1H), 7.33 (s, 1H), 7.30 (d, 1H), 7.21 (m, 2H), 7.09 (d, 1H), 6.87 (d, 1H), 5.33-5.46 (m, 2H), 3.05-3.27 (m, 2H), 1.27 (s, 9H). MS (DCI/NH$_3$) m/e 367 (M+H)$^+$. [α]$_D$+19.69° (c=0.975, 1:1 MeOH:CH$_2$Cl$_2$). Structure is trans by ROESY NMR, absolute stereochemistry assigned arbitrarily.

Example 42

N-[(1S,2R)-5-tert-butyl-2-fluoro-2,3-dihydro-1H-inden-1-yl]-N'-1H-indazol-4-ylurea The title compound was prepared by chiral separation of the corresponding racemic compound N-(5-tert-butyl-2-fluoro-2,3-dihydro-1H-inden-1-yl)-N'-1H-indazol-4-ylurea (Ex. 39) using a chiral column ChiralCel OD. $^1$H NMR (300 MHz, d$_6$-DMSO) 13.01 (broad s, 1H), 8.87 (s, 1H), 8.08 (s, 1H), 7.71 (d, 1H), 7.33 (s, 1H), 7.30 (d, 1H), 7.21 (m, 2H), 7.09 (d, 1H), 6.87 (d, 1H), 5.33-5.46 (m, 2H), 3.05-3.27 (m, 2H), 1.27 (s, 9H). MS (DCI/NH$_3$) m/e 367 (M+H)$^+$. [α]$_D$+22.67° (c=0.935, 1:1 MeOH:CH$_2$Cl$_2$). Structure is cis by ROESY NMR, absolute stereochemistry assigned arbitarily. Contains 17% of trans (–) diastereomer.

Example 43

N-1H-indazol-4-yl-N'-(6-fluoro-2,3-dihydro-1H-inden-1-yl)urea

Example 43A

6-Fluoro-2,3-dihydro-1H-inden-1-ylamine

The title compound was made according to the conditions described in Example 1C and 1D, except using 6-fluoro-indan-1-one instead of 5-tert-butyl-1-indanone. $^1$H NMR (300 MHz, CDCl$_3$) 7.15 (m, 1H), 7.02 (m, 1H), 6.88 (m, 1H), 4.35 (t, 1H), 2.90 (m, 1H), 2.75 (m, 1H), 2.52 (m, 1H), 1.75 (m, 1H, under H$_2$O peak). MS (CSI) m/e 152 (M+H)$^+$

Example 43B

4-[3-(6-fluoro-indan-1-yl)-ureido]-indazole-1-carboxylic acid methyl ester

The title compound was made according to the conditions described in Example 36I except using 6-fluoro-2,3-dihydro-1H-inden-1-ylamine instead of 5-(2-methoxy-1,1-dimethyl-ethyl)-indan-1-ylamine. MS (DCI) 369 (M+1).

Example 43C

N-1H-indazol-4-yl-N'-(6-fluoro-2,3-dihydro-1H-inden-1-yl)urea

The title compound was made from 4-[3-(6-fluoro-indan-1-yl)-ureido]-indazole-1-carboxylic acid methyl ester (Ex. 43B) according to the deprotection procedure by using 5M NaOH in methanol (example 9). $^1$H NMR (300 MHz, d$_6$-DMSO) 13.00 (broad s, 1H), 8.63 (s, 1H), 8.05 (s, 1H), 7.68 (d, 1H), 7.30 (dd, 1H), 7.22 (m, 1H), 7.03-7.15 (m, 3H), 6.80 (d, 1H), 5.20 (m, 1H), 2.88-2.99 (m, 1H), 2.75-2.87 (m, 1H), 2.46-2.58 (m, 1H, under DMSO), 1.80-1.93 (m, 1H). MS (DCI/NH$_3$) m/e 311 (M+H)$^+$. Anal. Calcd. For C$_{17}$H$_{15}$FN$_4$O: C, 65.80; H, 4.87; N, 18.05. Found: C, 65.55; H, 4.71; N, 17.76.

Example 44

N-1H-indazol-4-yl-N'-(6-methyl-2,3-dihydro-1H-inden-1-yl)urea

Example 44A

6-Methyl-2,3-dihydro-1H-inden-1-ylamine

The title compound was made according to the conditions described in Example 1C and 1D, except using 6-methyl-indan-1-one instead of 5-tert-butyl-1-indanone. $^1$H NMR (300 MHz, CDCl$_3$) 7.15 (s, 1H), 7.11 (d, 1H), 7.01 (d, 1H), 4.32 (t, 1H), 3.47 (MeOH), 2.86-2.96 (m, 1H), 2.70-2.81 (m, 1H), 2.44-2.55 (m, 1H), 2.35 (s, 3H), 1.64-1.75 (m, 1H) MS (CSI) m/e 148 (M+H)$^+$

Example 44B

4-[3-(6-methyl-indan-1-yl)-ureido]-indazole-1-carboxylic acid methyl ester

The title compound was made according to the conditions described in Example 36I except using 6-methyl-2,3-dihydro-1H-inden-1-ylamine (Ex. 44A) instead of 5-(2-methoxy-1,1-dimethyl-ethyl)-indan-1-ylamine. MS (DCI) 365 (M+1).

Example 44C

N-1H-indazol-4-yl-N'-(6-methyl-2,3-dihydro-1H-inden-1-yl)urea

The title compound was made from 4-[3-(6-fluoro-indan-1-yl)-ureido]-indazole-1-carboxylic acid methyl ester (Ex. 44B) according to the deprotection procedure by using 5M NaOH in methanol (example 9). $^1$H NMR (300 MHz, d$_6$-DMSO) 12.99 (broad s, 1H), 8.62 (s, 1H), 8.06 (s, 1H), 7.70 (d, 1H), 7.03-7.25 (m, 5H), 6.71 (d, 1H), 5.16 (m, 1H), 2.69-2.97 (m, 2H), 2.41-2.54 (m, 1H, under DMSO), 2.30 (s, 3H), 1.73-1.87 (m, 1H). MS (DCI/NH$_3$) m/e 307 (M+H)$^+$. Anal. Calcd. For C$_{18}$H$_{18}$N$_4$O.0.8H$_2$O: C, 67.40; H, 6.16; N, 17.47. Found: C, 67.35; H, 5.82; N, 17.34.

Example 48

N-(6-fluoro-5-piperidin-1-yl-2,3-dihydro-1H-inden-1-yl)-N'-1H-indazol-4-ylurea

Example 48A 5,6-difluoro-indan-1-one 3-(3,4-Difluoro-phenyl)-propionic acid (5 g, 26.9 mmol) and polyphosphoric acid (50 g) were heated together for 2 hours at 90 C. The reaction mixture was poured onto ice, and extracted with ethyl ether. The organic layer was washed with saturated sodium bicarbonate solution, dried with magnesium sulfate, and the solvent removed under vacuum to give a mixture of product and starting material (~3:2 by NMR).

This mixture was taken in ethyl ether-hexane (~1:1), washed with 3M aqueous potassium carbonate, dried with magnesium sulfate, and the solvent removed under vacuum to give 2.49 g of the desired product which was used without further purification. $^1$H NMR (300 MHz, CDCl$_3$) 7.53 (t, 1H), 7.27 (t, 1H), 3.11 (m, 2H), 2.73 (m, 2H). MS (CSI) m/e 169 (M+H)$^+$

Example 48B

6-Fluoro-5-piperidin-1-yl-indan-1-one 5,6-difluoro-indan-1-one (2.49 g, 14.8 mmol) and piperidine (4.4 ml, 3.78 g, 44.4 mmol) were dissolved in pyridine (10 ml) and heated to reflux for 16 hours. The reaction was cooled, and the solvent removed under vacuum. The residue was taken in ethyl ether, washed with 1N aqueous sodium hydroxide and water, dried with magnesium sulfate, and the solvent removed under vacuum to give the desired product as 2.97 g of a black solid that was used without further purification. $^1$H NMR (300 MHz, CDCl$_3$) 7.32 (d, 1H), 6.88 (d, 1H), 3.19 (m, 4H), 3.03 (m, 2H), 2.66 (m, 2H), 1.73 (m, 4H), 1.62 (m, 2H). MS (CSI) m/e 234 (M+H)$^+$

Example 48C

6-Fluoro-5-piperidin-1-yl-indan-1-ylamine

The title compound was made according to the conditions described in Example 1C and 1D, except using 6-fluoro-5-piperidin-1-yl-indan-1-one instead of 5-tert-butyl-1-indanone. $^1$H NMR (300 MHz, d$_6$-DMSO) 7.06 (d, 1H), 6.84 (d, 1H), 4.13 (t, 1H), 3.03 (m, 1H), 2.89 (m, 4H), 2.74-2.84 (m, 1H), 2.56-2.71 (m, 1H), 2.26-2.38 (m, 1H), 1.45-1.68 (m, 6H). MS (DCI/NH$_3$) m/e 235 (M+H)$^+$.

Example 48D

4-[3-(6-fluoro-5-piperidino-indan-1-yl)-ureido]-indazole-1-carboxylic acid methyl ester The title compound was made according to the conditions described in Example 36I except using 6-fluoro-5-piperidin- 1-yl-2,3-dihydro-1H-inden-1-ylamine (Ex. 48C) instead of 5-(2-methoxy-1,1-dimethyl-ethyl)-indan-1-ylamine. MS (DCI) 452 (M+1)

Example 48C

N-(6-fluoro-5-piperidin-1-yl-2,3-dihydro-1H-inden-1-yl)-N'-1H-indazol-4-ylurea The title compound was made from 4-[3-(6-fluoro-5-piperidino-indan-1-yl)-ureido]-indazole-1-carboxylic acid methyl ester (Ex. 48D) according to the deprotection procedure by using 5M NaOH in methanol (example 9). $^1$H NMR (300 MHz, d$_6$-DMSO) 8.88 (s, 1H), 8.18 (s, 1H), 7.68 (d, 1H), 7.00-7.25 (m, 5H), 5.08 (m, 1H), 3.09 (br, 4H), 2.87-3.00 (m, 1H), 2.72-2.85 (m, 1H), 2.43-2.55 (m, 1H, buried under DMSO), 1.81-1.92 (m, 1H), 1.73 (br, 4H), 1.55 (m, 2H). MS (DCI/NH$_3$) m/e 394 (M+H)$^+$. Anal. Calcd. For C$_{22}$H$_{24}$FN$_5$O.2HCl: C, 56.66; H, 5.62; N, 15.02. Found: C, 57.02; H, 5.74; N, 15.39.

Example 50

N-(5-tert-butyl-2,2-difluoro-2,3-dihydro-1H-inden-1-yl)-N'-1H-indazol-4-ylurea

Example 50A

5-tert-Butyl-2,2-difluoro-indan-1-one 5-tert-Butyl-2-fluoro-indan-1-one (0.21 g, 1 mmol) and triethyl amine (0.84 ml, 0.61 g, 6 mmol) were dissolved in 4 ml of methylene chloride. The solution was cooled to 0 C, and tert-butyl-dimethylsilyl trifluorosulfonate was added. The reaction was allowed to warm to ambient temperature, stirred 16 hours, and diluted with ethyl ether. The organic solution was washed sequentially with saturated sodium bicarbonate solution, 1N hydrochloric acid, saturated sodium bicarbonate, and brine, and dried with magnesium sulfate. The solvent was removed under vacuum to give the silyl enol ether which was used at once. The silyl enol ether was dissolved in 10 ml acetonitrile, and Accuflor (0.64 g, 1 mmol) was added. The reaction was stirred at ambient temperature for three hours. The solvent was then evaporated under vacuum, and the residue taken in methylene chloride and filtered. The filtrate was washed with water, dried with magnesium sulfate, and the solvent evaporated under reduced pressure to give 0.35 g of 5-tert-Butyl-2,2-difluoro-indan-1-one. $^1$H NMR (300 MHz, CDCl$_3$) 7.80 (d, 1H), 7.52 (d, 1H), 7.46, (s, 1H), 3.54 (t, 2H), 1.37 (s, 9H). MS (CSI) m/e 242 (M+NH$_4$)$^+$

Example 50B

5-tert-Butyl-2,2-difluoro-indan-1-ylamine

The title compound was made according to the conditions described in Example 57D, except using 5-tert-butyl-2,2-difluoro-1-indanone instead of 2-methyl-2-(1-oxoindan-5-yl)-propionitrile. $^1$H NMR (300 MHz, CDCl$_3$) 7.35 (s, 2H), 7.23 (s, 1H), 4.41 (t, 1H), 3.30-3.40 (m, 2H), 1.31 (s, 9H). MS (CSI) m/e 226 (M+H)$^+$

Example 50C

4-[3-(5-tert-Butyl-2,2-difluoro-indan-1-yl)-ureido]-indazole-1-carboxylic acid methyl ester The title compound was made according to the conditions described in Example 36I except using 5-tert-Butyl-2,2-difluoro-indan-1-ylamine instead of 5-(2-methoxy-1,1-dimethyl-ethyl)-indan-1-ylamine. MS (DCI) 443 (M+1).

Example 50D

N-(5-tert-butyl-2,2-difluoro-2,3-dihydro-1H-inden-1-yl)-N'-1H-indazol-4-ylurea The title compound was made from the compound in Ex. 50C according to the deprotection procedure by using 5M NaOH in methanol (example 9). $^1$H NMR (300 MHz, d$_6$-DMSO) 13.06 (br s, 1H), 8.81 (s, 1H), 8.06 (s, 1H), 7.70 (d, 1H), 7.37 (m, 2H), 7.25 (m, 2H), 7.11 (d, 1H), 7.00 (d, 1H), 5.49-5.61 (m, 1H) 4.03 (q, EtOAc), 3.27-3.66 (m, 2H), 1.99 (s, EtOAc), 1.29 (s, 9H), 1.17 (t, EtOAc). MS (DCI/NH$_3$) m/e 385 (M+H)$^+$. Anal. Calcd. For C$_{21}$H$_{22}$F$_2$N$_4$O.0.1H2O.0.1EtOAc: C, 65.07; H, 5.87; N, 14.18. Found: C, 65.08; H, 5.86; N, 14.13.

Example 51

1-(5-tert-butyl-indan-2-yl)-3-(1H-indazol-4-yl)-urea

Example 51A

5-tert-Butyl-indan-1,2-dione 2-oxime 5-tert-butyl-indan-1-one (9.39 g, 39 mmol) was dissolved in 150 ml methanol. Isoamyl nitrite (5 g, 43 mmol) and conc. HCl (5 ml) were added, and the reaction stirred at ambient temperature for 44 hours. The solvents were removed under vacuum to give 11.67 grams of crude product which was used without further purification. $^1$H NMR (300 MHz, CDCl$_3$) 7.82 (d, 1H), 7.51 (s, 1H), 7.49 (d, 1H), 3.83 (s, 2H), 3.50 (s, 1H, OH) 1.34 (s, 9H). MS (CSI) m/e 218 (M+H)$^+$, 235 (M+NH$_4$)$^+$

Example 51B

5-tert-Butyl-indan-2-ylamine 5-tert-Butyl-indan-1,2-dione 2-oxime (11.67 g) was hydrogenated over 10% palladium on carbon catalyst (2.95 g) using a mixture of 233 ml acetic acid and 15.6 ml concentrated sulfuric acid as solvent. The reaction was run at ambient temperature for 17 hours, under 60 psi hydrogen. After removal of catalyst by filtration, the filtrate was quenched by dropwise addition of 30 ml conc. ammonium hydroxide. The quenched mixture was then extracted with ethyl ether, the organic extracts dried with magnesium sulfate, and the solvent removed under vacuum to give 3.50 g of the product which was used without further purification. $^1$H NMR (300 MHz, CDCl$_3$) 7.17 (m, 3H), 3.84 (m, 1H), 3.14 (m, 2H), 2.67 (m, 2H), 1.31 (s, 9H). MS (CSI) m/e 190 (M+H)$^+$.

Example 51C.

4-[3-(5-tert-butyl-indan-2-yl)-ureido]-indazole-1-carboxylic acid methyl ester The title compound was made according to the conditions described in Example 36I except using 5-tert-Butyl-indan-2- ylamine (Ex. 51B) instead of 5-(2-methoxy-1,1-dimethylethyl)-indan-1-ylamine. MS (DCI) 407 (M+1).

Example 51D 1-(5-tert-butyl-indan-2-yl)-3-(1H-indazol-4-yl)-urea

The title compound was made from the compound in Ex. 51C. according to the deprotection procedure by using 5M NaOH in methanol (example 9). $^1$H NMR (300 MHz, d$_6$-DMSO) 8.66 (s, 1H), 8.07 (s, 1H), 7.67 (d, 1H), 7.32 (s, 1H), 7.19 (m, 2H), 7.03 (d, 1H), 6.81 (br, 1H), 4.46 (br, 1H), 3.44 (q, EtOH) 3.14-3.26 (m, 2H), 2.71-2.82 (m, 2H), 1.27 (s, 9H), 1.06 (t, EtOH). MS (DCI/NH$_3$) m/e 349 (M+H)$^+$. Anal. Calcd. For C$_{21}$H$_{24}$N$_4$O.HCl.0.33H2O.0.5EtOH: C, 63.84; H, 6.98; N, 13.54. Found: C, 63.89; H, 7.30; N, 13.75.

Example 52

N-1H-indazol-4-yl-N'-(7-methyl-2,3-dihydro-1H-inden-1-yl)urea

Example 52A

7-Methyl-indan-1-one

Polyphosphoric acid (15 g) was heated in a water bath to 85 C. 3-m-tolyl-propionic acid (2.0 g, 12.2 mmol) was added, and the reaction stirred at 75-85 C for 1 hour. The reaction was cooled, and quenched with ice and water. The quenched mixture was extracted with ethyl ether and the organics washed with saturated sodium bicarbonate. The solution was dried with magnesium sulfate and the solvent evaporated under vacuum. The residue was chromatographed using 1:10 ethyl acetate:hexane as the eluent, to give 0.66 g of 7-methyl-indan-1-one and 0.76 g of 5-methyl-indan-1-one. 7-methyl-indan-1-one: $^1$H NMR (300 MHz, CDCl$_3$) 7.42 (t, 1H), 7.23 (d, 1H), 7.10 (d, 1H), 3.09 (m, 2H), 2.66 (m, 2H), 2.64 (s, 3H). MS (CSI) m/e 147 (M+H)$^+$.

Example 52B

7-Methyl-indan-1-ylamine

The title compound was made according to the conditions described in Example 1C and 1D, except using 7-methyl-indan-1-one instead of 5-tert-butyl-1-indanone. $^1$H NMR (300 MHz, CDCl$_3$) 7.05-7.15 (m, 3H), 6.97 (d, 1H), 4.48 (dd, 1H), 3.07-3.18 (m, 1H), 2.80 (ddd, 1H), 2.41 (s, 3H), 2.26-2.40 (m, 1H), 1.81-1.91 (m, 1H). MS (CSI) m/e 148 (M+H)$^+$.

Example 52C

4-[3-(−7-Methyl-indan-1-yl)-ureido]-indazole-1-carboxylic acid methyl ester

The title compound was made according to the conditions described in Example 36I except using 7-methyl-indan-1-ylamine (Ex. 52B) instead of 5-(2-methoxy-1,1-dimethylethyl)-indan-1-ylamine. MS (DCI) 365 (M+1).

Example 52D

N-1H-indazol-4-yl-N'-(7-methyl-2,3-dihydro-1H-inden-1-yl)urea

The title compound was made from the compound in Ex. 52C according to the deprotection procedure by using 5M NaOH in methanol (example 9). $^1$H NMR (300 MHz, d$_6$-DMSO) 12.97 (br s, 1H), 8.50 (s, 1H), 8.01 (s, 1H), 7.70 (d, 1H), 7.12-7.24 (m, 3H), 7.05 (m, 2H), 6.67 (d, 1H), 5.26 (m, 1H), 2.99-3.10 (m, 1H), 2.81 (ddd, 1H), 2.24-2.37 (m, 1H), 2.31 (s, 3H), 1.92-2.02 (m, 1H). MS (DCI/NH$_3$) m/e 307 (M+H)$^+$.

Anal. Calcd. For C$_{21}$H$_{24}$N$_4$O.HCl.0.4 THF: C, 70.23; H, 6.37; N, 16.71. Found: C, 70.03; H, 6.30; N, 16.52.

Example 53

N-1H-indazol-4-yl-N'-(5-methyl-2,3-dihydro-1H-inden-1-yl)urea

Example 53A

5-Methyl-indan-1-one

Polyphosphoric acid (15 g) was heated in a water bath to 85 C. 3-m-tolyl-propionic acid (2.0 g, 12.2 mmol) was added, and the reaction stirred at 75-85 C for 1 hour. The reaction was cooled, and quenched with ice and water. The quenched mixture was extracted with ethyl ether and the organics washed with saturated sodium bicarbonate. The solution was dried with magnesium sulfate and the solvent evaporated under vacuum. The residue was chromatographed using 1:10 ethyl acetate:hexane as the eluent, to give 0.66 g of 7-methyl-indan-1-one and 0.76 g of 5-methyl-indan-1-one. 5-methyl-indan-1-one: $^1$H NMR (300 MHz, CDCl$_3$) 7.65 (d, 1H), 7.28 (s, 1H), 7.18 (d, 1H), 3.09 (m, 2H), 2.67 (m, 2H), 2.44 (s, 3H). MS (CSI) m/e 147 (M+H)$^+$.

Example 53B

5-Methyl-indan-1-ylamine

The title compound was made according to the conditions described in Example 1C and 1D, except using 5-methyl-indan-1-one instead of 5-tert-butyl-1-indanone. $^1$H NMR (300 MHz, CDCl$_3$) 7.22 (d, 1H), 7.04 (s, 1H), 7.03 (d, 1H), 4.34 (t, 1H), 2.93 (ddd, 1H), 2.71-2.83 (m, 1H), 2.44-2.55 (m, 1H), 2.33 (s, 3H), 1.64-1.75 (m, 1H). MS (CSI) m/e 148 (M+H)$^+$.

Example 53C

4-[3-(−5-Methyl-indan-1-yl)-ureido]-indazole-1-carboxylic acid methyl ester

The title compound was made according to the conditions described in Example 36I except using 5-methyl-indan-1-ylamine (Ex. 53B) instead of 5-(2-methoxy-1,1-dimethylethyl)-indan-1-ylamine. MS (DCI) 365 (M+1).

Example 53D

N-1H-indazol-4-yl-N'-(5-methyl-2,3-dihydro-1H-inden-1-yl)urea

The title compound was made from the compound in Ex. 53C according to the deprotection procedure by using 5M NaOH in methanol (example 9). $^1$H NMR (300 MHz, d$_6$-DMSO) 8.65 (s, 1H), 8.06 (s, 1H), 7.68 (d, 1H), 7.22 (m, 2H), 7.06 (m, 2H), 6.75 (d, 1H), 5.15 (m, 1H), 2.87-2.97 (m, 1H), 2.73-2.84 (m, 1H), 2.41-2.51 (m, 1H, buried under DMSO), 2.30 (s, 3H), 1.74-1.87 (m, 1H). MS (DCI/NH$_3$) m/e 307 (M+H)⁺, 329 (M+Na)⁺. Anal. Calcd. For C₂₁H₂₄N₄O.HCl.0.25 THF: C, 71.57; H, 6.86; N, 15.90. Found: C, 71.82; H, 6.90; N, 15.73.

Example 54

N-1H-indazol-4-yl-N'-(5-isopropyl-2,3-dihydro-1H-inden-1-yl)urea

Example 54A

3-Chloro-1-(4-isopropyl-phenyl)-propan-1-one

The title compound was prepared according to the procedure described in Ex. 1A, except using isopropylbenzene instead of t-butyl benzene. ¹H NMR (300 MHz, CDCl₃) 7.90 (d, 2H), 7.33 (d, 2H), 3.92 (t, 2H), 3.43 (t, 2H), 2.97 (septet, 1H), 1.27 (d, 6H). MS (CSI) m/e 211 (M+H)⁺, Cl isotope pattern seen.

Example 54B

5-Isopropyl-indan-1-one

The title compound was prepared according to the procedure described in Ex. 1B, except using compound from Ex. 54A instead of 1-(4-tert-butylphenyl)-3-chloro-1-propanone. ¹H NMR (300 MHz, CDCl₃) 7.69 (d, 1H), 7.32 (s, 1H), 7.23 (d, 1H), 3.11 (m, 2H), 2.99 (septet, 1H), 2.68 (m, 2H), 1.27 (d, 6H). MS (CSI) m/e 175 (M+H)⁺.

Example 54C

5-Isopropyl-indan-1-ylamine

The title compound was made according to the conditions described in Example 1C and 1D, except using 5-isopropyl-indan-1-one (Ex. 54B) instead of 5-tert-butyl-1-indanone. ¹H NMR (300 MHz, CDCl₃) 7.69 (d, 1H), 7.32 (s, 1H), 7.23 (d, 1H), 3.11 (m, 2H), 2.99 (septet, 1H), 2.68 (m, 2H), 1.27 (d, 6H). MS (CSI) m/e 175 (M+H)⁺

Example 54D

4-[3-(-5-Isopropyl-indan-1-yl)-ureido]-indazole-1-carboxylic acid methyl ester

The title compound was made according to the conditions described in Example 36I except using 5-isopropyl-indan-1-ylamine (Ex. 54C) instead of 5-(2-methoxy-1,1-dimethyl-ethyl)-indan-1-ylamine. MS (DCI) 393 (M+1).

Example 54E

N-1H-indazol-4-yl-N'-(5-isopropyl-2,3-dihydro-1H-inden-1-yl)urea

The title compound was made from the compound in Ex. 54D according to the deprotection procedure by using 5M NaOH in methanol (example 9). ¹H NMR (300 MHz, d₆-DMSO) 12.97 (br s, 1H), 8.56 (s, 1H), 8.03 (s, 1H), 7.67 (d, 1H), 7.05-7.27 (m, 5H), 6.68 (d, 1H), 5.15 (m, 1H), 2.73-3.00 (m, 2H), 2.40-2.50 (m, 1H, buried under DMSO), 1.77-1.88 (m, 1H), 1.20 (d, 6H). MS (DCI/NH₃) m/e 335 (M+H)⁺. Anal. Calcd. For C₂₁H₂₄N₄O.HCl.0.2 THF.0.2 NaOH: C, 68.68; H, 6.07; N, 17.04. Found: C, 68.61; H, 5.75; N, 16.95.

Example 56

N-1H-indazol-4-yl-N'-(4-piperidin-1-yl-2,3-dihydro-1H-inden-1-yl)urea

Example 56A

4-Bromo-indan-1-one O-methyl-oxime

4-Bromoindan-1-one (5.08 g, 24.1 mmol) was added to a mixture of methoxyamine hydrochloride (2.21 g, 26.5 mmol) in pyridine (40 mL) under nitrogen atmosphere and stirred overnight at ambient temperature. The reaction mixture was concentrated, added ethyl acetate (200 mL), washed with 3N hydrochloric acid (200 mL), dried with brine and anhydrous sodium sulfate, and concentrated. Obtained 4-bromoindan-1-one O-methyloxime (5.66 g, 98%) as an orange liquid. MS (DCI/NH₃) m/z: 239.94 [M+H]⁺. ¹H NMR (DMSO-d₆) □: 2.83 (m, 2H), 2.96 (m, 2H), 3.91 (s, 3H), 7.25 (t, 1H), 7.56 (d, 1H), 7.60 (d, 1H).

Example 56B

4-Piperidin-1-yl-indan-1-one O-methyl-oxime

4-Bromoindan-1-one O-methyloxime (6.40 g, 26.7 mmol) was added to a mixture of piperidine (2.72 g, 31.9 mmol), sodium tert-butoxide (3.84 g, 40.0 mmol), Pd₂(dba)₃ (0.74 g, 0.81 mmol) and BINAP (1.49 g, 2.39 mmol) in dioxane (50 mL) under nitrogen atmosphere. The stirred mixture was heated at 170° C. for 5 minutes on the microwave. After cooling to ambient temperature, the reaction mixture was filtered through celite, then silica gel with 25% ethyl acetate in hexane. The filtrate was concentrated to a brown oil and chromatographed on silica gel with 4% ethyl acetate in hexane. Obtained 4-piperidin-1-ylindan-1-one O-methyloxime (4.33 g, 66%) as an orange oil. MS (ESI) m/z: 245.00 [M+H]⁺. ¹H NMR (DMSO-d₆) □: 1.55 (m, 2H), 1.64 (m, 4H), 2.79 (m, 2H), 2.91 (m, 6H), 3.87 (s, 3H), 6.94 (dd, 1H), 7.19 (m, 2H).

Example 56C

4-Piperidin-1-yl-indan-1-ylamine

4-Piperidin-1-ylindan-1-one O-methyloxime (4.33 g, 17.7 mmol) was added to a mixture of 20% ammonia in methanol (200 mL) and Raney 2800 nickel (43 g) in a stainless steel autoclave. The reactor was sealed and flushed with nitrogen, and then it was pressurized with hydrogen (60 psi). The mixture was stirred at ambient temperature for 90 minutes. The Raney nickel was filtered off, washed with methanol and the filtrate was concentrated. Obtained 4-piperidin-1-ylindan-1-yl-amine (3.81 g, 99%) as a yellow oil. MS (DCI/NH₃) m/z: 217.13 [M+H]⁺. ¹H NMR (DMSO-d₆) δ: 1.51 (m, 3H), 1.62 (m, 4H), 1.77 (s, 2H), 2.28 (m, 1H), 2.62 (m, 1H), 2.80 (m, 3H), 2.94 (m, 2H), 4.14 (t, 1H), 6.71 (d, 1H), 6.95 (d, 1H), 7.09 (t, 1H).

Example 56D

4-[3-(4-Piperidin-1-yl-indan-1-yl)-ureido]indazole-1-carboxylic acid methyl ester The title compound was made according to the conditions described in Example 36I except using 4-piperidin-1-yl-indan-1-ylamine (Ex. 56C) instead of 5-(2-methoxy-1,1-dimethyl-ethyl)-indan-1-ylamine. MS (DCI) 434 (M+1).

Example 56E 1-(1H-Indazol-4-yl)-3-(4-piperidin-1-yl-indan-1-yl)-urea 4-(2,5-Dioxopyrrolidin-1-yl-oxycarbonylamino)-indazole-1-carboxylic acid methyl ester (5.57 g, 16.8 mmol) was added to a solution of 4-piperidin-1-ylindan-1-ylamine (3.81 g, 17.6 mmol) and DIPEA (3.0 mL, 17.2 mmol) in DMF (80 mL) under nitrogen atmosphere at ambient temperature. After 30 minutes the reaction solution was diluted with water (350 mL), the resulting beige precipitate was filtered off, washed with water and air-dried. The wet cake was added to a solution of methanol (200 mL), water (3 mL) and TEA (7.0 mL, 50.2 mmol). The mixture was refluxed for 90 minutes, cooled to room temperature, diluted with water (200 mL), collected the beige precipitate by filtration, rinsed with water and air-dried. The wet cake was vacuum dried to constant weight, yielding 1-(1H-indazol-4-yl)-3-(4-piperidin-1-ylindan-1-yl)-urea (5.89 g, 93%) as a beige solid. MS (ESI) m/z: 376.00 [M+H]$^+$. $^1$H NMR (DMSO-d$_6$) δ: 1.56 (m, 2H), 1.65 (m, 4H), 1.78 (m, 1H), 2.44 (m, 1H), 2.77 (m, 1H), 2.85 (m, 3H), 2.95 (m, 2H), 5.16 (q, 1H), 6.66 (d, 1H), 6.81 (d, 1H), 6.95 (d, 1H), 7.07 (d, 1H), 7.22 (m, 2H), 7.68 (d, 1H), 8.05 (s, 1H), 8.62 (s, 1H), 13.00 (s, 1H). Anal Calcd for C$_{22}$H$_{25}$N$_5$O: C, 70.38; H, 6.71; N, 18.65. Found: C, 70.24; H, 6.72; N, 18.47.

Example 57

1-[5-(Cyano-isopropyl)-indan-1-yl]-3-(1H-indazol-4-yl)-urea

Example 57A 2-(3-Bromo-phenyl)-2-methyl-propionitrile

The title compound was made according to the procedure described in Ex. 36B except using 3-bromophenyl-acetonitrile instead of 3-bromophenyl-acetic acid methyl ester.

Example 57B

2-Methyl-2-(3-trimethylsilanylethynyl-phenyl)-propionitrile

Ethynyltrimethylsilane (4.0 mL, 28.9 mmol) was added to a mixture of ACN (100 mL), TEA (25 mL), 2-(3-bromophenyl)-2-methylpropionitrile (5.0 g, 22.3 mmol), (Ph$_3$P)$_2$PdCl$_2$ (780 mg, 1.11 mol) and copper(I) iodide (130 mg, 0.68 mmol) under nitrogen atmosphere. The reaction mixture was refluxed for 3 hours, cooled to ambient temperature, concentrated to a black residue and filtered through silica gel with 20% ethyl acetate in hexane. The filtrate was concentrated to a red oil and chromatographed on silica gel with 2% ethyl acetate in hexane. Obtained 2-methyl-2-(3-trimethylsilanylethynylphenyl)-propionitrile (4.00 g, 74%) as an orange oil. $^1$H NMR (DMSO-d$_6$) δ: 0.24 (s, 9H), 1.69 (s, 6H), 7.43 (m, 2H), 7.56 (m, 2H).

Example 57C

2-Methyl-2-(1-oxo-indan-5-yl)-propionitrile

2-Methyl-2-(3-trimethylsilanylethynylphenyl)-propionitrile (4.00 g, 16.6 mmol) was added to a mixture of THF (35 mL), TEA (4.82 mL, 34.6 mmol), water (3.12 mL, 173 mmol), [Rh(COD)Cl]$_2$ (83 mg, 168 µmol) and triphenylphosphine (1.81 g, 6.90 mmol) in a stainless steel autoclave. The reactor was sealed and flushed with carbon monoxide, and then it was pressurized with carbon monoxide (500 psi). The stirred mixture was heated at 160° C. for 4 hours. After cooling to ambient temperature, the reaction mixture was concentrated to a black residue and chromatographed on silica gel with 20-40% ethyl acetate in hexane. Obtained 2-methyl-2-(1-oxo-indan-5-yl)-propionitrile (2.71 g, 82%) as a brown solid. MS (DCI/NH$_3$) m/z: 200.0 [M+H]$^+$. $^1$H NMR (DMSO-d$_6$) δ: 1.73 (s, 6H), 2.65 (m, 2H), 3.14 (m, 2H), 7.60 (dd, 1H), 7.68 (d, 1H), 7.74 (d, 1H).

Example 57D 2-(1-Amino-indan-5-yl)-2-methyl-propionitrile

2-Methyl-2-(1-oxoindan-5-yl)-propionitrile (6.00 g, 30.1 mmol) was added to a mixture of ammonium acetate (69.6 g, 903 mmol) in IPA (600 mL) under nitrogen atmosphere at ambient temperature. After stirring 1 hour, sodium cyanoborohydride (6.62 g, 105 mmol) was added to the mixture and refluxed for 2 hours. The reaction solution was cooled to room temperature, added 3N sodium hydroxide (300 mL), extracted with TBME (2×500 mL) and concentrated the organic extracts to an oil. Dissolved in ethyl acetate (500 mL), extracted with 1N hydrochloric acid (3×300 mL), combined the aqueous layers, added 3N sodium hydroxide (400 mL), extracted with ethyl acetate (2×1 L), dried with brine and anhydrous sodium sulfate, and concentrated. Obtained 2-(1-aminoindan-5-yl)-2-methylpropionitrile (4.26 g, 71%) as a yellow oil. MS (DCI/NH$_3$) m/z: 201.10 [M+H]$^+$. $^1$H NMR (DMSO-d$_6$) δ: 1.60 (m, 1H), 1.66 (s, 6H), 1.93 (br, 2H), 2.35 (m, 1H), 2.74 (m, 1H), 2.86 (m, 1H), 4.17 (t, 1H), 7.32 (m, 3H).

Example 57E

1-[5-(Cyano-isopropyl)-indan-1-yl]-3-(1H-indazol-4-yl)-urea 4-(2,5-Dioxopyrrolidin-1-yl-oxycarbonylamino)-indazole-1-carboxylic acid methyl ester (3.31 g, 9.96 mmol) was added to a solution of 2-(1-aminoindan-5-yl)-2-methylpropionitrile (2.09 g, 10.5 mmol) and DIPEA (1.8 mL, 10.3 mmol) in DMF (40 mL) under nitrogen atmosphere at ambient temperature. After 1 hour the reaction solution was diluted with water (200 mL), the resulting white precipitate was filtered off, washed with water and air-dried. The wet cake was added to a solution of methanol (100 mL), water (3 mL) and TEA (2.8 mL, 20.1 mmol). The mixture was refluxed for 30 minutes, cooled the solution to room temperature, diluted with water (500 mL), collected the white precipitate by filtration, rinsed with water and air-dried. The wet cake was vacuum dried to constant weight, yielding 1-[5-(cyano-isopropyl)-indan-1-yl]-3-(1H-indazol-4-yl)-urea (3.32 g, 93%) as a white solid. MS (ESI) m/z: 360.07 [M+H]$^+$. $^1$H NMR (DMSO-d$_6$) δ: 1.69 (s, 6H), 1.87 (m, 1H), 2.47 (m, 1H), 2.89 (m, 1H), 2.98 (m, 1H), 5.19 (q, 1H), 6.73 (d, 1H), 7.08 (d, 1H), 7.22 (t, 1H), 7.39 (s, 2H), 7.44 (s, 1H), 7.66 (d, 1H), 8.04 (s, 1H), 8.59 (s, 1H), 13.00 (s, 1H). Anal Calcd for C$_{21}$H$_{21}$N$_5$O.0.4H$_2$O: C, 68.80; H, 5.99; N, 19.10. Found: C, 68.94; H, 5.72; N, 18.95.

Example 58

N-1H-indazol-4-yl-N'-{5-[4-(trifluoromethyl)piperidin-1-yl]-2,3-dihydro-1H-inden-1-yl}urea

Example 58A 5-(4-Trifluoromethyl-piperidin-1-yl)-indan-1-ylamine

The title compound was made according to the conditions described in Examples 16A-16C, except using 4-trifluoromethylpiperidine instead of piperidine in ex. 16A.

Example 58B

4-{3-[5-(4-trifluoromethyl-piperidin-1-yl)-indan-1-yl]-ureido}-indazol-1-carboxylic acid methyl ester The title compound was made according to the conditions described in Example 36I except using 5-(4-trifluoromethylpiperidin-1-yl)-indan-1-ylamine (Ex. 58A) instead of 5-(2-methoxy-1,1-dimethyl-ethyl)-indan-1-ylamine. MS (DCI) 502 (M+1).

Example 58C

N-1H-indazol-4-yl-N'-{5-[4-(trifluoromethyl)piperidin-1-yl]-2,3-dihydro-1H-inden-1-yl}urea The title compound was made from the compound in Ex. 58B according to the deprotection procedure by using 5M NaOH in methanol (example 9). MS (ESI) m/z: 444.1 [M+H]$^+$. $^1$H NMR (DMSO-d$_6$) □, 1.56 (m, 2H), 1.79 (m, 1H), 1.83 (m, 2H), 2.46 (m, 1H), 2.71 (t, 2H), 2.80 (m, 1H), 2.91 (m, 1H), 3.73 (d, 2H), 5.09 (q, 1H), 6.61 (d, 1H), 6.87 (m, 2H), 7.07 (d, 1H), 7.21 (m, 2H), 7.67 (d, 1H), 8.04 (s, 1H), 8.55 (s, 1H), 12.99 (s, 1H).

Example 59

N-1H-indazol-4-yl-N'-(5-cis-octahydroisoquinolin-2(1H)-yl-2,3-dihydro-1H-inden-1-yl)urea

Example 59A 5-(cis-Octahydro-isoquinolin-2-yl)-indan-1-ylamine

The title compound was made according to the conditions described in Examples 16A-16C, except using octahydroisoquinoline instead of piperidine in ex. 16A.

Example 59B

4-{3-[5-(cis-Octahydro-isoquinolin-2-yl)-indan-1-yl]-ureido}-indazol-1-carboxylic acid methyl ester The title compound was made according to the conditions described in Example 36I except using 5-(Octahydro-isoquinolin-2-yl)-indan-1-ylamine (Ex. 59A) instead of 5-(2-methoxy-1,1-dimethyl-ethyl)-indan-1-ylamine. MS (DCI) 488 (M+1).

Example 59C

N-1H-indazol-4-yl-N'-(5-cis-octahydroisoquinolin-2(1H)-yl-2,3-dihydro-1H-inden-1-yl)urea The title compound was made from the compound in Ex. 59B according to the deprotection procedure by using 5M NaOH in methanol (example 9). 1H NMR (DMSO-d$_6$) □, 1.33 (m, 1H), 1.47 (m, 4H), 1.57 (m, 3H), 1.78 (m, 4H), 2.44 (m, 1H), 2.78 (m, 1H), 2.88 (m, 3H), 5.09 (q, 1H), 6.60 (d, 1H), 6.81 (m, 2H), 7.07 (d, 1H), 7.14 (d, 1H), 7.21 (t, 1H), 7.67 (d, 1H), 8.04 (s, 1H), 8.56 (s, 1H), 12.98 (s, 1H).

Example 60

N-[5-(1,4'-bipiperidin-1'-yl)-2,3-dihydro-1H-inden-1-yl]-N'-1H-indazol-4-ylurea

Example 60A

5-[1,4']Bipiperidinyl-1'-yl-indan-1-ylamine

The title compound was made according to the conditions described in Examples 16A-16C, except using [1,4']bipiperidinyl instead of piperidine in ex. 16A.

Example 60B

4-[3-(5-[1,4']Bipiperidinyl-1'-yl-indan-1-yl)-ureido]-indazole-1-carboxylic acid methyl ester The title compound was made according to the conditions described in Example 36I except using 5-[1,4']Bipiperidinyl-1'-yl-indan-1-ylamine (Ex. 60A) instead of 5-(2-methoxy-1,1-dimethyl-ethyl)-indan-1-ylamine. MS (DCI) 517 (M+1).

Example 60C

N-[5-(1,4'-bipiperidin-1'-yl)-2,3-dihydro-1H-inden-1-yl]-N'-1H-indazol-4-ylurea

The title compound was made from the compound in Ex. 60B according to the deprotection procedure by using 5M NaOH in methanol (example 9). MS (ESI) m/z: 459.20 [M+H]$^+$. $^1$H NMR (DMSO-d$_6$) δ: 1.39 (m, 2H), 1.48 (m, 5H), 1.75 (m, 3H), 2.32 (m, 1H), 2.45 (m, 5H), 2.61 (t, 2H), 2.78 (m, 1H), 2.88 (m, 1H), 3.67 (d, 2H), 5.07 (q, 1H), 6.60 (d, 1H), 6.83 (m, 2H), 7.07 (d, 1H), 7.21 (m, 2H), 7.67 (d, 1H), 8.03 (s, 1H), 8.55 (s, 1H), 12.99 (s, 1H). Anal Calcd for C$_{27}$H$_{34}$N$_6$O.0.25H$_2$O: C, 70.03; H, 7.51; N, 18.15. Found: C, 69.97; H, 7.36; N, 18.29.

Example 61

N-1H-indazol-4-yl-N'-[5-(4-phenylpiperidin-1-yl)-2,3-dihydro-1H-inden-1-yl]urea

Example 61A 5-(4-Phenyl-piperidin-1-yl)-indan-1-ylamine

The title compound was made according to the conditions described in Examples 16A-16C, except using 4-phenyl-piperidine instead of piperidine in ex. 16A.

Example 61B

4-{3-[5-(4-Phenyl-piperidin-1-yl)-indan-1-yl]-ureido}-indazole-1-carboxylic acid methyl ester The title compound was made according to the conditions described in Example 36I except using 5-(4-phenyl-piperidin-1-yl)-indan-1-ylamine (Ex. 61A) instead of 5-(2-methoxy-1,1-dimethyl-ethyl)-indan-1-ylamine. MS (DCI) 510 (M+1).

Example 61C

N-1H-indazol-4-yl-N'-[5-(4-phenylpiperidin-1-yl)-2,3-dihydro-1H-inden-1-yl]urea The title compound was made from the compound in Ex. 61B according to the deprotection procedure by using 5M NaOH in methanol (example 9). MS (ESI) m/z: 452.20 [M+H]$^+$. $^1$H NMR (DMSO-d$_6$) δ: 1.8 (m, 5H), 2.44 (m, 1H), 2.75 (m, 3H), 2.92 (m, 1H), 3.76 (d, 2H), 5.12 (q, 1H), 6.64 (d, 1H), 6.89 (m, 2H), 7.07 (d, 1H), 7.21 (m, 3H), 7.29 (m, 4H), 7.67 (d, 1H), 8.04 (s, 1H), 8.56 (s, 1H), 12.99 (s, 1H). Anal Calcd for C$_{28}$H$_{29}$N$_5$O.0.1H$_2$O: C, 74.18; H, 6.49; N, 15.45. Found: C, 74.09; H, 6.35; N, 15.58.

Example 62

N-1H-indazol-4-yl-N'-[5-(4-phenylpiperazin-1-yl)-2,3-dihydro-1H-inden-1-yl]urea

Example 62A

5-(4-Phenyl-piperazin-1-yl)-indan-1-ylamine

The title compound was made according to the conditions described in Examples 16A-16C, except using 4-phenyl-piperazine instead of piperidine in ex. 16A.

Example 62B

4-{3-[5-(4-Phenyl-piperazin-1-yl)-indan-1-yl]-ureido}-indazole-1-carboxylic acid methyl ester The title compound was made according to the conditions described in Example 36I except using 5-(4-phenyl-piperazin-1-yl)-indan-1-ylamine (Ex. 62A) instead of 5-(2-methoxy-1,1-dimethyl-ethyl)-indan-1-ylamine. MS (DCI) 511 (M+1).

Example 62C

N-1H-indazol-4-yl-N'-[5-(4-phenylpiperazin-1-yl)-2,3-dihydro-1H-inden-1-yl]urea The title compound was made from the compound in Ex. 62B according to the deprotection procedure by using 5M NaOH in methanol (example 9). MS (ESI) m/z: 453.16 [M+H]$^+$. $^1$H NMR (DMSO-d$_6$) δ: 1.82 (m, 1H), 2.44 (m, 1H), 2.82 (m, 1H), 2.93 (m, 1H), 3.27 (s, 8H), 5.10 (q, 1H), 6.62 (d, 1H), 6.81 (t, 1H), 6.92 (m, 2H), 7.01 (d, 2H), 7.07 (d, 1H), 7.21 (q, 4H), 7.67 (d, 1H), 8.04 (s, 1H), 8.56 (s, 1H), 12.99 (s, 1H). Anal Calcd for C$_{27}$H$_{28}$N$_6$O: C, 71.66; H, 6.24; N, 18.57. Found: C, 71.40; H, 6.10; N, 18.62.

Example 63

N-1H-indazol-4-yl-N'-[5-(4-methylpiperidin-1-yl)-2,3-dihydro-1H-inden-1-yl]urea

Example 63A

5-(4-Methyl-piperidin-1-yl)-indan-1-ylamine

The title compound was made according to the conditions described in Examples 16A-16C, except using 4-methyl-piperidine instead of piperidine in ex. 16A.

Example 63B

4-{3-[5-(4-Methyl-piperidin-1-yl)-indan-1-yl]-ureido}-indazole-1-carboxylic acid methyl ester The title compound was made according to the conditions described in Example 36I except using 5-(4-methyl-piperidin-1-yl)-indan-1-ylamine (Ex. 63A) instead of 5-(2-methoxy-1,1-dimethyl-ethyl)-indan-1-ylamine. MS (DCI) 448 (M+1).

Example 63C

N-1H-indazol-4-yl-N'-[5-(4-methylpiperidin-1-yl)-2,3-dihydro-1H-inden-1-yl]urea The title compound was made from the compound in Ex. 62B according to the deprotection procedure by using 5M NaOH in methanol (example 9). MS (ESI) m/z: 390.12 [M+H]$^+$. $^1$H NMR (DMSO-d$_6$) δ: 0.94 (d, 3H), 1.23 (m, 2H), 1.48 (m, 1H), 1.65 (d, 2H), 1.80 (m, 1H), 2.45 (m, 1H), 2.63 (t, 2H), 2.78 (m, 1H), 2.90 (m, 1H), 3.60 (d, 2H), 5.10 (q, 1H), 6.59 (d, 1H), 6.83 (m, 2H), 7.07 (d, 1H), 7.15 (d, 1H), 7.21 (t, 1H), 7.67 (d, 1H), 8.03 (s, 1H), 8.54 (s, 1H), 12.98 (s, 1H). Anal Calcd for C$_{23}$H$_{27}$N$_5$O: C, 70.92; H, 6.99; N, 17.98. Found: C, 70.75; H, 6.63; N, 17.74.

Example 64

N-1H-indazol-4-yl-N'-[5-(3-methylpiperidin-1-yl)-2,3-dihydro-1H-inden-1-yl]urea

Example 64A

5-(3-Methyl-piperidin-1-yl)-indan-1-ylamine

The title compound was made according to the conditions described in Examples 16A-16C, except using 3-methyl-piperidine instead of piperidine in ex. 16A.

Example 64B

4-{3-[5-(3-Methyl-piperidin-1-yl)-indan-1-yl]-ureido}-indazole-1-carboxylic acid methyl ester The title compound was made according to the conditions described in Example 36I except using 5-(3-Methyl-piperidin-1-yl)-indan-1-ylamine (Ex. 64A) instead of 5-(2-methoxy-1,1-dimethyl-ethyl)-indan-1-ylamine. MS (DCI) 448 (M+1).

Example 64C

N-1H-indazol-4-yl-N'-[5-(3-methylpiperidin-1-yl)-2,3-dihydro-1H-inden-1-yl]urea

The title compound was made from the compound in Ex. 64B according to the deprotection procedure by using 5M NaOH in methanol (example 9). MS (ESI) m/z: 390.10 [M+H]$^+$. $^1$HNMR (DMSO-d$_6$) δ: 0.92 (d, 3H), 1.02 (m, 1H), 1.58 (m, 1H), 1.72 (m, 4H), 2.28 (t, 1H), 2.45 (m, 1H), 2.57 (m, 1H), 2.78 (m, 1H), 2.90 (m, 1H), 3.56 (m, 2H), 5.10 (q, 1H), 6.61 (d, 1H), 6.83 (m, 2H), 7.07 (d, 1H), 7.18 (q, 2H), 7.67 (d, 1H), 8.03 (s, 1H), 8.55 (s, 1H), 12.97 (s, 1H). Anal Calcd for $C_{23}H_{27}N_5O.0.2H_2O$: C, 70.27; H, 7.03; N, 17.82. Found: C, 70.15; H, 6.63; N, 17.74.

Example 65

N-1H-indazol-4-yl-N'-[5-(2-oxopiperidin-1-yl)-2,3-dihydro-1H-inden-1-yl]urea

Example 65A 1-(1-Amino-indan-5-yl)-piperidin-2-one

The title compound was made according to the conditions described in Examples 16A-16C, except using piperidin-2-one instead of piperidine in ex. 16A.

Example 65B

4-{3-[5-(2-Oxo-piperidin-1-yl)-indan-1-yl]-ureido}-indazole-1-carboxylic acid methyl ester The title compound was made according to the conditions described in Example 36I except using 1-(1-amino-indan-5-yl)-piperidin-2-one (Ex. 65A) instead of 5-(2-methoxy-1,1-dimethyl-ethyl)-indan-1-ylamine. MS (DCI) 448 (M+1).

Example 65C

N-1H-indazol-4-yl-N'-[5-(2-oxopiperidin-1-yl)-2,3-dihydro-1H-inden-1-yl]urea

The title compound was made from the compound in Ex. 65B according to the deprotection procedure by using 5M NaOH in methanol (example 9). MS (ESI) m/z: 390.07 [M+H]$^+$. $^1$H NMR (DMSO-d$_6$) δ: 1.85 (m, 5H), 2.37 (t, 2H), 2.47 (m, 1H), 2.85 (m, 1H), 2.94 (m, 1H), 3.57 (t, 2H), 5.17 (q, 1H), 6.73 (d, 1H), 7.08 (t, 2H), 7.16 (s, 1H), 7.22 (t, 1H), 7.32 (d, 1H), 7.67 (d, 1H), 8.05 (s, 1H), 8.60 (s, 1H), 13.00 (s, 1H). Anal Calcd for $C_{22}H_{23}N_5O_2.0.8H_2O$: C, 65.43; H, 6.14; N, 17.34. Found: C, 65.40; H, 6.45; N, 17.41.

Example 66

N-1H-indazol-4-yl-N'-[5-(2-methylpiperidin-1-yl)-2,3-dihydro-1H-inden-1-yl]urea

Example 66A 5-(2-Methyl-piperidin-1-yl)-indan-1-ylamine

The title compound was made according to the conditions described in Examples 16A-16C, except using 2-methyl-piperidine instead of piperidine in ex. 16A.

Example 66B

4-{3-[5-(2-Methyl-piperidin-1-yl)-indan-1-yl]-ureido}-indazole-1-carboxylic acid methyl ester The title compound was made according to the conditions described in Example 36I except using 5-(2-Methyl-piperidin-1-yl)-indan-1-ylamine (Ex. 66A) instead of 5-(2-methoxy-1,1-dimethyl-ethyl)-indan-1-ylamine. MS (DCI) 448 (M+1).

Example 66C

N-1H-indazol-4-yl-N'-[5-(2-methylpiperidin-1-yl)-2,3-dihydro-1H-inden-1-yl]urea

The title compound was made from the compound in Ex. 66B according to the deprotection procedure by using 5M NaOH in methanol (example 9). MS (ESI) m/z: 390.17 [M+H]$^+$. $^1$H NMR (DMSO-d$_6$) δ: 0.93 (d, 3H), 1.54 (m, 4H), 1.77 (m, 3H), 2.43 (m, 1H), 2.79 (m, 1H), 2.87 (m, 2H), 3.13 (m, 1H), 3.91 (m, 1H), 5.08 (q, 1H), 6.61 (d, 1H), 6.82 (m, 2H), 7.07 (d, 1H), 7.18 (q, 2H), 7.67 (d, 1H), 8.03 (s, 1H), 8.55 (s, 1H), 12.99 (s, 1H). Anal Calcd for $C_{23}H_{27}N_5O.0.6H_2O$: C, 69.01; H, 7.10; N, 17.49. Found: C, 68.78; H, 6.71; N, 17.48.

Example 68

N-(4-azepan-1-yl-2,3-dihydro-1H-inden-1-yl)-N'-1H-indazol-4-ylurea

Example 68A

4-Azepan-1-yl-indan-1-ylamine

The title compound was made according to the conditions described in Examples 56B-56C, except using azepane instead of piperidine in ex. 56B.

Example 68B

4-[3-(4-Azepan-1-yl-indan-1-yl)-ureido]-indazole-1-carboxylic acid methyl ester

The title compound was made according to the conditions described in Example 36I except using 4-azepan-1-yl-indan-1-ylamine (Ex. 68A) instead of 5-(2-methoxy-1,1-dimethyl-ethyl)-indan-1-ylamine. MS (DCI) 434 (M+1).

Example 68C

N-(4-azepan-1-yl-2,3-dihydro-1H-inden-1-yl)-N'-1H-indazol-4-ylurea

The title compound was made from the compound in Ex. 68B according to the deprotection procedure by using 5M NaOH in methanol (example 9). MS (ESI) m/z: 390.14 [M+H]$^+$. $^1$H NMR (DMSO-d$_6$) δ: 1.59 (s, 4H), 1.75 (s, 5H), 2.44 (m, 1H), 2.85 (m, 1H), 2.94 (m, 1H), 5.11 (q, 1H), 6.66 (d, 1H), 6.74 (d, 1H), 6.79 (d, 1H), 7.07 (m, 2H), 7.21 (t, 1H), 7.67 (d, 1H), 8.05 (s, 1H), 8.61 (s, 1H), 12.99 (s, 1H). Anal Calcd for $C_{23}H_{27}N_5O \cdot 0.6H_2O$: C, 69.01; H, 7.10; N, 17.49. Found: C, 69.26; H, 6.95; N, 16.89.

Example 69

N-1H-indazol-4-yl-N'-[4-(4-methylpiperidin-1-yl)-2,3-dihydro-1H-inden-1-yl]urea

Example 69A 4-(4-Methyl-piperidin-1-yl)-indan-1-ylamine

The title compound was made according to the conditions described in Examples 56B-56C, except using 4-methyl-piperidine instead of piperidine in ex. 56B.

Example 69B

4-{3-[4-(4-Methyl-piperidin-1-yl)-indan-1-yl]-ureido}-indazole-1-carboxylic acid methyl ester The title compound was made according to the conditions described in Example 36I except using 4-(4-methyl-piperidin-1-yl)-indan-1ylamine (Ex. 69A) instead of 5-(2-methoxy-1,1-dimethyl-ethyl)-indan-1-ylamine. MS (DCI) 448 (M+1).

Example 69C

N-1H-indazol-4-yl-N'-[4-(4-methylpiperidin-1-yl)-2,3-dihydro-1H-inden-1-yl]urea

The title compound was made from the compound in Ex. 69B according to the deprotection procedure by using 5M NaOH in methanol (example 9). MS (ESI) m/z: 390.15 [M+H]$^+$. $^1$H NMR (DMSO-d$_6$) δ: 0.98 (d, 3H), 1.28 (m, 2H), 1.49 (m, 1H), 1.74 (m, 3H), 2.43 (m, 1H), 2.55 (m, 1H), 2.67 (m, 1H), 2.77 (m, 1H), 2.84 (m, 1H), 3.20 (d, 1H), 5.18 (q, 1H), 6.66 (d, 1H), 6.81 (d, 1H), 6.95 (d, 1H), 7.07 (d, 1H), 7.15 (t, 1H), 7.21 (t, 1H), 7.67 (d, 1H), 8.05 (s, 1H), 8.61 (s, 1H), 12.99 (s, 1H). Anal Calcd for $C_{23}H_{27}N_5O \cdot 0.2H_2O$: C, 70.27; H, 7.03; N, 17.82. Found: C, 70.36; H, 7.20; N, 17.69.

Example 70

N-1H-indazol-4-yl-N'-[4-(3-methylpiperidin-1-yl)-2,3-dihydro-1H-inden-1-yl]urea

Example 70A 4-(3-Methyl-piperidin-1-yl)-indan-1-ylamine

The title compound was made according to the conditions described in Examples 56B-56C, except using 3-methyl-piperidine instead of piperidine in ex. 56B.

Example 70B

4-{3-[4-(3-Methyl-piperidin-1-yl)-indan-1-yl]-ureido}-indazole-1-carboxylic acid methyl ester The title compound was made according to the conditions described in Example 36I except using 4-(3-methyl-piperidin-1-yl)-indan-1-ylamine (Ex. 70A) instead of 5-(2-methoxy-1,1-dimethyl-ethyl)-indan-1-ylamine. MS (DCI) 448 (M+1).

Example 70C

N-1H-indazol-4-yl-N'-[4-(4-methylpiperidin-1-yl)-2,3-dihydro-1H-inden-1-yl]urea

The title compound was made from the compound in Ex. 70B according to the deprotection procedure by using 5M NaOH in methanol (example 9). MS (ESI) m/z: 390.15 [M+H]$^+$. $^1$H NMR (DMSO-d$_6$) δ: 0.93 (t, 3H), 1.05 (m, 1H), 1.62 (m, 1H), 1.75 (m, 4H), 2.27 (m, 1H), 2.46 (m, 1H), 2.62 (m, 1H), 2.82 (m, 2H), 3.18 (m, 2H), 5.18 (q, 1H), 6.70 (d, 1H), 6.81 (d, 1H), 6.95 (d, 1H), 7.07 (d, 1H), 7.21 (m, 2H), 7.67 (d, 1H), 8.05 (s, 1H), 8.62 (s, 1H), 12.99 (s, 1H). Anal Calcd for $C_{23}H_{27}N_5O \cdot 0.5H_2O$: C, 69.32; H, 7.08; N, 17.57. Found: C, 69.24; H, 7.06; N, 17.36.

Example 71

N-1H-indazol-4-yl-N'-[4-(2-methylpiperidin-1-yl)-2,3-dihydro-1H-inden-1-yl]urea

Example 71A 4-(2-Methyl-piperidin-1-yl)-indan-1-ylamine

The title compound was made according to the conditions described in Examples 56B-56C, except using 2-methyl-piperidine instead of piperidine in ex. 56B.

Example 71B

4-{3-[4-(2-Methyl-piperidin-1-yl)-indan-1-yl]-ureido}-indazole-1-carboxylic acid methyl ester The title compound was made according to the conditions described in Example 36I except using 4-(2-methyl-piperidin-1-yl)-indan-1-ylamine (Ex. 71A) instead of 5-(2-methoxy-1,1-dimethyl-ethyl)-indan-1-ylamine. MS (DCI) 448 (M+1).

Example 71C

N-1H-indazol-4-yl-N'-[4-(2-methylpiperidin-1-yl)-2,3-dihydro-1H-inden-1-yl]urea

The title compound was made from the compound in Ex. 70B according to the deprotection procedure by using 5M NaOH in methanol (example 9). MS (ESI) m/z: 390.10 [M+H]$^+$. $^1$HNMR (DMSO-d$_6$) δ: 0.87 (t, 3H), 1.44 (m, 2H), 1.62 (m, 5H), 2.39 (m, 1H), 2.65 (m, 1H), 2.74 (m, 1H), 2.87 (m, 1H), 3.06 (m, 1H), 5.20 (m, 1H), 6.69 (m, 1H), 6.95 (m, 3H), 7.19 (m, 2H), 7.67 (d, 1H), 8.05 (d, 1H), 8.62 (d, 1H), 13.00 (s, 1H). Anal Calcd for $C_{23}H_{27}N_5O \cdot 0.9H_2O$: C, 68.09; H, 7.15; N, 17.26. Found: C, 67.98; H, 6.81; N, 17.12.

Example 72

N-1H-indazol-4-yl-N'-[(1R)-4-piperidin-1-yl-2,3-dihydro-1H-inden-1-yl]urea

The title compound was prepared by chiral separation of the corresponding racemic compound I-(1H-Indazol-4-yl)-3-(4-piperidin-1-yl-indan-1-yl)-urea (Ex. 56E) using a chiral column ChiralCel OD. [α]$_D$: +89.5° (HCl salt, c: 1.02, MeOH). MS (ESI) m/z: 376.00 [M+H]$^+$. $^1$H NMR (DMSO-d$_6$) δ: 1.56 (m, 2H), 1.65 (m, 4H), 1.78 (m, 1H), 2.44 (m, 1H), 2.77 (m, 1H), 2.85 (m, 3H), 2.95 (m, 2H), 5.16 (q, 1H), 6.66

(d, 1H), 6.81 (d, 1H), 6.95 (d, 1H), 7.07 (d, 1H), 7.22 (m, 2H), 7.68 (d, 1H), 8.05 (s, 1H), 8.62 (s, 1H), 13.00 (s, 1H). Anal Calcd for $C_{22}H_{25}N_5O$: C, 70.38; H, 6.71; N, 18.65. Found: C, 70.45; H, 6.91; N, 18.00.

Example 73

N-1H-indazol-4-yl-N'-[(1S)-4-piperidin-1-yl-2,3-dihydro-1H-inden-1-yl]urea

The title compound was prepared by chiral separation of the corresponding racemic compound I-(1H-Indazol-4-yl)-3-(4-piperidin-1-yl-indan-1-yl)-urea (Ex. 56E) using a chiral column ChiralCel OD. $[\alpha]_D$: −98.5° (HCl salt, c: 1.02, MeOH).

MS (ESI) m/z: 376.00 [M+H]$^+$. $^1$H NMR (DMSO-d$_6$) δ: 1.56 (m, 2H), 1.65 (m, 4H), 1.78 (m, 1H), 2.44 (m, 1H), 2.77 (m, 1H), 2.85 (m, 3H), 2.95 (m, 2H), 5.16 (q, 1H), 6.66 (d, 1H), 6.81 (d, 1H), 6.95 (d, 1H), 7.07 (d, 1H), 7.22 (m, 2H), 7.68 (d, 1H), 8.05 (s, 1H), 8.62 (s, 1H), 13.00 (s, 1H). Anal Calcd for $C_{22}H_{25}N_5O$: C, 70.38; H, 6.71; N, 18.65. Found: C, 70.18; H, 6.93; N, 18.42.

Example 74

N-1H-indazol-4-yl-N'-(4-pyrrolidin-1-yl-2,3-dihydro-1H-inden-1-yl)urea

Example 74A

4-Pyrrolidin-1-yl-indan-1-ylamine

The title compound was made according to the conditions described in Examples 56B-56C, except using pyrrolidine instead of piperidine in ex. 56B.

Example 74B

4-[3-(4-Pyrrolidin-1-yl-indan-1-yl)-ureido]-indazole-1-carboxylic acid methyl ester The title compound was made according to the conditions described in Example 36I except using 4-Pyrrolidin-1-yl-indan-1-ylamine (Ex. 74A) instead of 5-(2-methoxy-1,1-dimethyl-ethyl)-indan-1-ylamine. MS (DCI) 420 (M+1).

Example 74C

N-1H-indazol-4-yl-N'-(4-pyrrolidin-1-yl-2,3-dihydro-1H-inden-1-yl)urea

The title compound was made from the compound in Ex. 74B according to the deprotection procedure by using 5M NaOH in methanol (example 9). MS (ESI) m/z: 362.11 [M+H]$^+$. $^1$H NMR (DMSO-d$_6$) δ: 1.73 (m, 1H), 1.90 (m, 4H), 2.42 (m, 1H), 2.99 (m, 1H), 3.06 (m, 1H), 5.09 (q, 1H), 6.51 (d, 1H), 6.71 (dd, 2H), 7.07 (m, 2H), 7.21 (t, 1H), 7.68 (d, 1H), 8.05 (s, 1H), 8.60 (s, 1H), 12.99 (s, 1H). Anal Calcd for $C_{21}H_{23}N_5O$: C, 67.07; H, 6.16; N, 18.62. Found: C, 67.08; H, 6.14; N, 18.39.

Example 75

N-[(1R)-5-(1-cyano-1-methylethyl)-2,3-dihydro-1H-inden-1-yl]-N'-1H-indazol-4-ylurea The title compound was prepared by chiral separation of the corresponding racemic compound 1-[5-(cyano-isopropyl)-indan-1-yl]-3-(1H-indazol-4-yl)-urea (Ex. 57E) using a chiral column ChiralCel OD. $[\alpha]_D$: +35.4° (c: 1.04, MeOH). MS (ESI) m/z: 360.07 [M+H]$^+$. $^1$H NMR (DMSO-d$_6$) □: 1.69 (s, 6H), 1.87 (m, 1H), 2.47 (m, 1H), 2.89 (m, 1H), 2.98 (m, 1H), 5.19 (q, 1H), 6.73 (d, 1H), 7.08 (d, 1H), 7.22 (t, 1H), 7.39 (s, 2H), 7.44 (s, 1H), 7.66 (d, 1H), 8.04 (s, 1H), 8.59 (s, 1H), 13.00 (s, 1H). Anal Calcd for $C_{21}H_{21}N_5O\cdot0.3H_2O$: C, 69.14; H, 5.97; N, 19.20. Found: C, 69.08; H, 5.95; N, 19.31.

Example 76

N-[(1S)-5-(1-cyano-1-methylethyl)-2,3-dihydro-1H-inden-1-yl]-N'-1H-indazol-4-ylurea The title compound was prepared by chiral separation of the corresponding racemic compound 1-[5-(cyano-isopropyl)-indan-1-yl]-3-(1H-indazol-4-yl)-urea (Ex. 57E) using a chiral column ChiralCel OD. MS (ESI) m/z: 360.07 [M+H]$^+$. $^1$H NMR (DMSO-d$_6$) δ: 1.69 (s, 6H), 1.87 (m, 1H), 2.47 (m, 1H), 2.89 (m, 1H), 2.98 (m, 1H), 5.19 (q, 1H), 6.73 (d, 1H), 7.08 (d, 1H), 7.22 (t, 1H), 7.39 (s, 2H), 7.44 (s, 1H), 7.66 (d, 1H), 8.04 (s, 1H), 8.59 (s, 1H), 13.00 (s, 1H). Anal Calcd for $C_{21}H_{21}N_5O\cdot0.45H_2O$: C, 68.63; H, 6.01; N, 19.05. Found: C, 68.82; H, 5.89; N, 18.36.

Example 77

N-1H-indazol-4-yl-N'-[4-(2-methylpyrrolidin-1-yl)-2,3-dihydro-1H-inden-1-yl]urea

Example 77A 4-(2-Methyl-pyrrolidin-1-yl)-indan-1-ylamine

The title compound was made according to the conditions described in Examples 56B-56C, except using 2-methyl-pyrrolidine instead of piperidine in ex. 56B.

Example 77B

4-{3-[4-(2-Methyl-pyrrolidin-1-yl)-indan-1-yl]-ureido}-indazole-1-carboxylic acid methyl ester The title compound was made according to the conditions described in Example 36I except using 4-(2-methyl-pyrrolidin-1-yl)-indan-1-ylamine (Ex. 77A) instead of 5-(2-methoxy-1,1-dimethyl-ethyl)-indan-1-ylamine. MS (DCI) 420 (M+1).

Example 77C

N-1H-indazol-4-yl-N'-[4-(2-methylpyrrolidin-1-yl)-2,3-dihydro-1H-inden-1-yl]urea The title compound was made from the compound in Ex. 77B according to the deprotection procedure by using 5M NaOH in methanol (example 9). MS (ESI) m/z: 376.12 [M+H]$^+$. $^1$H NMR (DMSO-d$_6$) δ: 1.00 (t, 3H), 1.57 (m, 1H), 1.79 (m, 1H), 1.91 (m, 1H), 2.14 (m, 1H), 2.30 (m, 1H), 2.88 (m, 2H), 3.12 (m, 2H), 3.55 (m, 1H), 3.89 (m, 1H), 5.18 (m, 1H), 6.59 (t, 1H), 6.66 (d, 1H), 6.73 (dd, 1H), 7.08 (m, 2H), 7.22 (t, 1H), 7.67 (d, 1H), 8.06 (d, 1H), 8.64 (m, 1H), 12.99 (s, 1H). Anal Calcd for $C_{22}H_{25}N_5O$: C, 70.38; H, 6.71; N, 18.65. Found: C, 65.16; H, 5.42; N, 16.53.

Example 78

N-[4-(2-azabicyclo[2.2.1]hept-2-yl)-2,3-dihydro-1H-inden-1-yl]-N'-1H-indazol-4-ylurea

Example 78A 4-(2-Aza-bicyclo[2.2.1]hept-2-yl)-indan-1-ylamine

The title compound was made according to the conditions described in Examples 56B-56C, except using 2-aza-bicyclo[2.2.1]heptane instead of piperidine in ex. 56B.

Example 78B

4-{3-[4-(2-Methyl-pyrrolidin-1-yl)-indan-1-yl]-ureido}-indazole-1-carboxylic acid methyl ester The title compound was made according to the conditions described in Example 36I except using 4-(2-aza-bicyclo[2.2.1]hept-2-yl)-indan-1-ylamine (Ex. 78A) instead of 5-(2-methoxy-1,1-dimethyl-ethyl)-indan-1-ylamine. MS (DCI) 446 (M+1).

Example 78C

N-[4-(2-azabicyclo[2.2.1]hept-2-yl)-2,3-dihydro-1H-inden-1-yl]-N'-1H-indazol-4-ylurea The title compound was made from the compound in Ex. 78B according to the deprotection procedure by using 5M NaOH in methanol (example 9). MS (ESI) m/z: 388.13 [M+H]$^+$. $^1$HNMR (DMSO-$d_6$) δ: 1.30 (m, 1H), 1.46 (d, 1H), 1.64 (m, 4H), 1.79 (m, 1H), 2.27 (m, 1H), 2.87 (m, 3H), 3.15 (m, 1H), 3.62 (m, 1H), 4.10 (d, 1H), 5.09 (m, 1H), 6.42 (dd, 1H), 6.61 (m, 2H), 7.05 (m, 2H), 7.21 (t, 1H), 7.67 (d, 1H), 8.05 (d, 1H), 8.63 (d, 1H), 12.99 (s, 1H). Anal Calcd for $C_{23}H_{25}N_5O.1.7H_2O$: C, 66.07; H, 6.85; N, 16.75. Found: C, 66.18; H, 6.77; N, 16.24.

Example 79

N-[4-(8-azabicyclo[3.2.1]oct-8-yl)-2,3-dihydro-1H-inden-1-yl]-N'-1H-indazol-4-ylurea

Example 79A 4-(8-Aza-bicyclo[3.2.1]oct-8-yl)-indan-1-ylamine

The title compound was made according to the conditions described in Examples 56B-56C, except using 8-aza-bicylo[3.2.1]octane instead of piperidine in ex. 56B.

Example 79B

4-{3-[4-(8-Aza-bicyclo[3.2.1]oct-8-yl)-indan-1-yl]-ureido}-indazole-1-carboxylic acid methyl ester The title compound was made according to the conditions described in Example 36I except using 4-(8-Aza-bicyclo[3.2.1]oct-8-yl)-indan-1-ylamine (Ex. 79A) instead of 5-(2-methoxy-1,1-dimethyl-ethyl)-indan-1-ylamine. MS (DCI) 460 (M+1).

Example 79C

N-[4-(8-azabicyclo[3.2.1]oct-8-yl)-2,3-dihydro-1H-inden-1-yl]-N'-1H-indazol-4-ylurea The title compound was made from the compound in Ex. 79B according to the deprotection procedure by using 5M NaOH in methanol (example 9). MS (ESI) m/z: 401.98 [M+H]$^+$. $^1$H NMR (DMSO-$d_6$) δ: 1.42 (d, 2H), 1.48 (m, 1H), 1.67-1.90 (m, 7H), 1.96 (m, 1H), 2.45 (m, 1H), 2.83 (m, 1H), 2.91 (m, 1H), 3.98 (d, 1H), 4.07 (d, 1H), 5.12 (q, 1H), 6.64 (d, 1H), 6.72 (d, 1H), 6.79 (d, 1H), 7.07 (m, 2H), 7.21 (t, 1H), 7.68 (d, 1H), 8.05 (s, 1H), 8.61 (s, 1H), 13.00 (s, 1H). Anal Calcd for $C_{24}H_{27}N_5O.0.5H_2O.0.2TEA$: C, 70.27; H, 7.25; N, 16.91. Found: C, 70.08; H, 7.50; N, 17.36.

Example 80

N-1H-indazol-4-yl-N'-[4-(trifluoromethyl)-2,3-dihydro-1H-inden-1-yl]urea

Example 80A

4-Trifluoromethyl-indan-1-one

The title compound was made according to the procedure described in Ex. 57B-57C except using 2-trifluoromethyl-bromobenzene instead of 2-(3-bromophenyl)-2-methylpropionitrile in Ex. 57B.

Example 80B

4-Trifluoromethyl-indan-1-ylamine

The title compound was made according to the conditions described in Example 1C and 1D, except using 4-trifluoromethyl-indan-1-one (Ex. 80A) instead of 5-tert-butyl-1-indanone.

Example 80C

4-[3-(4-Trifluoromethyl-indan-1-yl)-ureido]-indazole-1-carboxylic acid methyl ester The title compound was made according to the conditions described in Example 36I except using 4-trifluoromethyl-indan-1-ylamine (Ex. 80B) instead of 5-(2-methoxy-1,1-dimethyl-ethyl)-indan-1-ylamine. MS (DCI) 419 (M+1).

Example 80D

N-1H-indazol-4-yl-N'-[4-(trifluoromethyl)-2,3-dihydro-1H-inden-1-yl]urea

The title compound was made from the compound in Ex. 80C according to the deprotection procedure by using 5M NaOH in methanol (example 9). MS (ESI) m/z: 360.92 [M+H]$^+$. $^1$H NMR (DMSO-$d_6$) δ: 1.93 (m, 1H), 2.54 (m, 1H), 3.02 (m, 1H), 3.13 (m, 1H), 5.27 (q, 1H), 6.81 (d, 1H), 7.09 (d, 1H), 7.22 (t, 1H), 7.46 (t, 1H), 7.65 (m, 3H), 8.06 (s, 1H), 8.65

Example 81

N-(4-chloro-2,3-dihydro-1H-inden-1-yl)-N'-1H-indazol-4-ylurea

Example 81A

4-Chloro-indan-1-ylamine

The title compound was made according to the conditions described in Ex. 57D, except using 4-chloro-indan-1-one instead of 2-methyl-2-(1-oxoindan-5-yl)-propionitrile.

Example 81B

4-[3-(4-Chloro-indan-1-yl)-ureido]-indazole-1-carboxylic acid methyl ester

The title compound was made according to the conditions described in Example 36I except using 4-chloro-indan-1-ylamine (Ex. 81A) instead of 5-(2-methoxy-1,1-dimethyl-ethyl)-indan-1-ylamine. MS (DCI) 385 (M+1).

Example 81C

N-(4-chloro-2,3-dihydro-1H-inden-1-yl)-N'-1H-indazol-4-ylurea

The title compound was made from the compound in Ex. 81B according to the deprotection procedure by using 5M NaOH in methanol (example 9). MS (ESI) m/z: 326.92 [M+H]$^+$. $^1$H NMR (DMSO-d$_6$) δ: 1.88 (m, 1H), 2.54 (m, 1H), 2.88 (m, 1H), 2.99 (m, 1H), 5.31 (q, 1H), 6.79 (d, 1H), 7.09 (d, 1H), 7.22 (t, 1H), 7.31 (m, 3H), 7.65 (d, 1H), 8.05 (s, 1H), 8.64 (s, 1H), 13.00 (s, 1H). Anal Calcd for C$_{17}$H$_{15}$N$_4$OCl: C, 62.48; H, 4.63; N, 17.14. Found: C, 62.29; H, 4.41; N, 16.85.

Example 83

N-1H-indazol-4-yl-N'-[4-(trifluoromethoxy)-2,3-dihydro-1H-inden-1-yl]urea

Example 83A 4-trifluoromethoxy-indan-1-one

The title compound was made according to the procedure described in Ex. 57B-57C except using 2-trifluoromethoxy-bromobenzene instead of 2-(3-bromophenyl)-2-methylpropionitrile in Ex. 57B.

Example 83B

4-Trifluoromethoxy-indan-1-ylamine

The title compound was made according to the conditions described in Example 1C and 1D, except using 4-trifluoromethoxy-indan-1-one (Ex. 83A) instead of 5-tert-butyl-1-indanone.

Example 83C

4-[3-(4-Trifluoromethoxy-indan-1-yl)-ureido]-indazole-1-carboxylic acid methyl ester The title compound was made according to the conditions described in Example 36I except using 4-trifluoromethoxy-indan-1-ylamine (Ex. 83B) instead of 5-(2-methoxy-1,1-dimethyl-ethyl)-indan-1-ylamine. MS (DCI) 435 (M+1).

Example 83D

N-1H-indazol-4-yl-N'-[4-(trifluoromethoxy)-2,3-dihydro-1H-inden-1-yl]urea

The title compound was made from the compound in Ex. 83C according to the deprotection procedure by using 5M NaOH in methanol (example 9). MS (ESI) m/z: 376.88 [M+H]$^+$. $^1$H NMR (DMSO-d$_6$) δ: 1.91 (m, 1H), 2.54 (m, 1H), 2.90 (m, 1H), 3.02 (m, 1H), 5.30 (q, 1H), 6.81 (d, 1H), 7.09 (d, 1H), 7.22 (m, 2H), 7.40 (m, 2H), 7.65 (d, 1H), 8.05 (s, 1H), 8.63 (s, 1H), 13.00 (s, 1H). Anal Calcd for C$_{18}$H$_{15}$N$_4$O$_2$F$_3$: C, 57.45; H, 4.02; N, 14.89. Found: C, 57.25; H, 3.96; N, 14.68.

Example 84

N-(4-bromo-2,3-dihydro-1H-inden-1-yl)-N'-1H-indazol-4-ylurea

Example 84A

4-Bromo-indan-1-ylamine

The title compound was made according to the conditions described in Ex. 57D, except using 4-bromo-indan-1-one instead of 2-methyl-2-(1-oxoindan-5-yl)-propionitrile.

Example 84B

4-[3-(4-Bromo-indan-1-yl)-ureido]-indazole-1-carboxylic acid methyl ester

The title compound was made according to the conditions described in Example 36I except using 4-bromo-indan-1-ylamine (Ex. 84A) instead of 5-(2-methoxy-1,1-dimethyl-ethyl)-indan-1-ylamine. MS (DCI) 431 (M+1).

Example 84C

N-(4-bromo-2,3-dihydro-1H-inden-1-yl)-N'-1H-indazol-4-ylurea

The title compound was made from the compound in Ex. 84B according to the deprotection procedure by using 5M NaOH in methanol (example 9). MS (ESI) m/z: 372.78 [M+H]$^+$. $^1$H NMR (DMSO-d$_6$) δ: 1.88 (m, 1H), 2.53 (m, 1H), 2.86 (m, 1H), 2.94 (m, 1H), 5.30 (q, 1H), 6.80 (d, 1H), 7.09 (d, 1H), 7.22 (m, 2H), 7.34 (d, 1H), 7.46 (d, 1H), 7.65 (d, 1H), 8.06 (s, 1H), 8.64 (s, 1H), 13.00 (s, 1H). Anal Calcd for C$_{17}$H$_{15}$N$_4$OBr: C, 55.00; H, 4.07; N, 15.09. Found: C, 54.89; H, 3.81; N, 14.93.

Example 85

N-1H-indazol-4-yl-N'-(4-octahydroisoquinolin-2(1H)-yl-2,3-dihydro-1H-inden-1-yl)urea

Example 85A 4-(Octahydro-isoquinolin-2-yl)-indan-1-ylamine

The title compound was made according to the conditions described in Examples 56B-56C, except using octahydro-isoquinoline instead of piperidine in ex. 56B.

(s, 1H), 13.00 (s, 1H). Anal Calcd for C$_{18}$H$_{15}$N$_4$OF$_3$: C, 60.00; H, 4.20; N, 15.55. Found: C, 59.73; H, 3.98; N, 15.24.

Example 85B

4-{3-[4-(Octahydro-isoquinolin-2-yl)-indan-1-yl]-ureido}-indazole-1-carboxylic acid methyl ester The title compound was made according to the conditions described in Example 36I except using 4-(octahydro-isoquinolin-2-yl)-indan-1-ylamine (Ex. 85A) instead of 5-(2-methoxy-1,1-dimethyl-ethyl)-indan-1-ylamine. MS (DCI) 488 (M+1).

Example 85C

N-1H-indazol-4-yl-N'-(4-octahydroisoquinolin-2(1H)-yl)-2,3-dihydro-1H-inden-1-yl)urea The title compound was made from the compound in Ex. 85B according to the deprotection procedure by using 5M NaOH in methanol (example 9). MS (ESI) m/z: 430.13 [M+H]$^+$. $^1$H NMR (DMSO-d$_6$) δ: 1.20-2.04 (m, 13H), 2.38-3.22 (m, 7H), 5.16 (m, 1H), 6.68 (d, 1H), 6.81 (d, 1H), 6.93 (t, 1H), 7.07 (d, 1H), 7.15 (t, 1H), 7.22 (t, 1H), 7.67 (d, 1H), 8.04 (s, 1H), 8.62 (d, 1H), 13.00 (s, 1H). Anal Calcd for C$_{26}$H$_{31}$N$_5$O.0.5H$_2$O: C, 71.21; H, 7.35; N, 15.97. Found: C, 71.10; H, 7.67; N, 15.95.

Example 86

N-[4-(cyanomethyl)-2,3-dihydro-1H-inden-1-yl]-N'-1H-indazol-4-ylurea

Example 86A 4-cyanomethyl-indan-1-one

The title compound was made according to the procedure described in Ex. 57B-57C except using 2-cyanomethyl-bromobenzene instead of 2-(3-bromophenyl)-2-methylpropionitrile in Ex. 57B.

Example 86B (1-Amino-indan-4-yl)-acetonitrile

The title compound was made according to the conditions described in Example 1C and 1D, except using 4-cyanomethyl-indan-1-one-(Ex. 86A) instead of 5-tert-butyl-1-indanone.

Example 86C

4-[3-(4-Cyanomethyl-indan-1-yl)-ureido]-indazole-1-carboxylic acid methyl ester

The title compound was made according to the conditions described in Example 36I except using (1-amino-indan-4-yl)-acetonitrile (Ex. 86B) instead of 5-(2-methoxy-1,1-dimethyl-ethyl)-indan-1-ylamine. MS (DCI) 390 (M+1).

Example 86D

N-[4-(cyanomethyl)-2,3-dihydro-1H-inden-1-yl]-N'-1H-indazol-4-ylurea

The title compound was made from the compound in Ex. 86C according to the deprotection procedure by using 5M NaOH in methanol (example 9). MS (ESI) m/z: 331.96 [M+H]$^+$. $^1$H NMR (DMSO-d$_6$) δ: 1.85 (m, 1H), 2.54 (m, 1H), 2.85 (m, 1H), 2.98 (m, 1H), 4.01 (s, 2H), 5.22 (q, 1H), 6.74 (d, 1H), 7.08 (d, 1H), 7.22 (d, 1H), 7.27 (m, 2H), 7.33 (m, 1H), 7.66 (d, 1H), 8.05 (s, 1H), 8.61 (s, 1H), 13.00 (s, 1H). Anal Calcd for C$_{19}$H$_{17}$N$_5$O: C, 68.87; H, 5.17; N, 21.13. Found: C, 68.49; H, 4.91; N, 20.92.

Example 87

N-1H-indazol-4-yl-N'-(4-methyl-2,3-dihydro-1H-inden-1-yl)urea

Example 87A

4-Methyl-indan-1-ylamine

The title compound was made according to the conditions described in Ex. 57D, except using 4-methyl-indan-1-one instead of 2-methyl-2-(1-oxoindan-5-yl)-propionitrile.

Example 87B

4-[3-(4-Methyl-indan-1-yl)-ureido]-indazole-1-carboxylic acid methyl ester

The title compound was made according to the conditions described in Example 36I except using 4-methyl-indan-1-ylamine (Ex. 87A) instead of 5-(2-methoxy-1,1-dimethyl-ethyl)-indan-1-ylamine. MS (DCI) 365 (M+1).

Example 87C

N-1H-indazol-4-yl-N'-(4-methyl-2,3-dihydro-1H-inden-1-yl)urea

The title compound was made from the compound in Ex. 87B according to the deprotection procedure by using 5M NaOH in methanol (example 9). MS (ESI) m/z: 306.96 [M+H]$^+$. $^1$H NMR (DMSO-d$_6$) δ: 1.81 (m, 1H), 2.25 (s, 3H), 2.48 (m, 1H), 2.76 (m, 1H), 2.89 (m, 1H), 5.21 (q, 1H), 6.68 (d, 1H), 7.05-7.24 (m, 5H), 7.67 (d, 1H), 8.04 (s, 1H), 8.59 (s, 1H), 12.99 (s, 1H). Anal Calcd for C$_{18}$H$_{18}$N$_4$O: C, 70.57; H, 5.92; N, 18.29. Found: C, 70.35; H, 5.80; N, 18.00.

Example 88

1-[(R)-5-Chloro-indan-1-yl)-3-(1H-indazol-4-yl)-urea

Example 88A 5-(R)-Chloro-indan-1-ylamine 5-chloro-2,3-dihydro-1H-inden-1-ylamine (3.13 g, 18.7 mmol), N-acetyl-(D)-leucine (3.24 g, 18.7 mmol) were dissolved in refluxing ethanol (125 mL). The solution was allowed to cool to ambient temperature. The solids were filtered and rinsed with cold EtOH. The solid was then resuspended in ethanol (45 mL) and brought to reflux. The solution was allowed to cool to ambient temperature and the solids were filtered. The solid was dried at 40° C. under reduced pressure to provide the title compound (0.9 g) as a salt

Example 88B

4-[3-(R)5-Chloro-indan-1-yl)-ureido]-indazole-1-carboxylic acid methyl ester

The title compound was made according to the conditions described in Example 36I except using 5-(R)-Chloro-indan- 1-ylamine (Ex. 88A) as a free base instead of 5-(2-methoxy-1,1-dimethyl-ethyl)-indan-1-ylamine. MS (DCI) 385 (M+1).

Example 88C

1-[(R)-5-chloro-indan-1-yl]-3-(1H-indazol-4-yl)-urea

The title compound was made from the compound in Ex. 88B according to the deprotection procedure by using 5M NaOH in methanol (example 9). $[\alpha]_D$: +33.2° (c: 1.0, 1:1 MeOH:DMSO) MS (ESI) m/z: 327.02 $[M+H]^+$. $^1$H NMR (DMSO-$d_6$) δ: 1.85 (m, 1H), 2.53 (m, 1H), 2.87 (m, 1H), 2.96 (m, 1H), 5.17 (q, 1H), 6.78 (d, 1H), 7.08 (d, 1H), 7.22 (t, 1H), 7.29 (d, 1H), 7.34 (m, 2H), 7.66 (d, 1H), 8.07 (s, 1H), 8.66 (s, 1H), 13.00 (s, 1H). Anal Calcd for $C_{17}H_{15}N_4OCl$: C, 62.48; H, 4.63; N, 17.14. Found: C, 62.57; H, 4.52; N, 17.17.

Example 90

1-[5-(1,1-Dioxo-1-thiomorpholin-4-yl)-indan-1-yl]-3-(1H-indazol-4-yl)-urea

Example 90A 5-(1,1-Dioxo-1-thiomorpholin-4-yl)-indan-1-ylamine

The title compound was made according to the conditions described in Examples 56B-56C, except using thiomorpholine 1,1-dioxane instead of piperidine in ex. 56B.

Example 90B

4-{3-[5-(1,1-Dioxo-1-thiomorpholin-4-yl)-indan-1-yl]-ureido}-indazole-1-carboxylic acid methyl ester The title compound was made according to the conditions described in Example 36I except using 5-(1,1-Dioxo-1-thiomorpholin-4-yl)-indan-1-ylamine (Ex. 90A) instead of 5-(2-methoxy-1,1-dimethyl-ethyl)-indan-1-ylamine. MS (DCI) 484 (M+1).

Example 90C

1-[5-(1,1-Dioxo-1-thiomorpholin-4-yl)-indan-1-yl]-3-(1H-indazol-4-yl)-urea

The title compound was made from the compound in Ex. 90B according to the deprotection procedure by using 5M NaOH in methanol (example 9). MS (ESI) m/z: 425.91 $[M+H]^+$. $^1$H NMR (DMSO-$d_6$) δ: 1.82 (m, 1H), 2.46 (m, 1H), 2.81 (m, 1H), 2.92 (m, 1H), 3.11 (s, 4H), 3.75 (s, 4H), 5.10 (q, 1H), 6.63 (d, 1H), 6.90 (d, 1H), 6.95 (s, 1H), 7.07 (d, 1H), 7.22 (m, 2H), 7.66 (d, 1H), 8.04 (s, 1H), 8.55 (s, 1H), 12.97 (s, 1H). Anal Calcd for $C_{21}H_{23}N_5O_3S \cdot 0.6H_2O \cdot 0.4Ni$: C, 54.87; H, 5.31; N, 15.23. Found: C, 54.85; H, 5.32; N, 15.48.

Example 91

1-(1H-Indazol-4-yl)-3-(4-morpholin-4-yl-indan-1-yl)-urea

Example 91A

4-Morpholin-4-yl-indan-1-ylamine

The title compound was made according to the conditions described in Examples 56B-56C, except using morpholine instead of piperidine in ex. 56B.

Example 91B

4-[3-(4-Morpholin-4-yl-indan-1-yl)-ureido]-indazole-1-carboxylic acid methyl ester The title compound was made according to the conditions described in Example 36I except using 4-morpholine-4-yl-indan-1-ylamine (Ex. 91A) instead of 5-(2-methoxy-1,1-dimethyl-ethyl)-indan-1-ylamine. MS (DCI) 436 (M+1).

Example 91C 1-(1H-Indazol-4-yl)-3-(4-morpholin-4-yl-indan-1-yl)-urea

The title compound was made from the compound in Ex. 91B according to the deprotection procedure by using 5M NaOH in methanol (example 9). MS (ESI) m/z: 377.91 $[M+H]^+$. $^1$H NMR (DMSO-$d_6$) δ: 1.79 (m, 1H), 2.44 (m, 1H), 2.79 (m, 1H), 2.90 (m, 3H), 2.99 (m, 2H), 3.74 (m, 4H), 5.16 (q, 1H), 6.67 (d, 1H), 6.83 (d, 1H), 7.00 (d, 1H), 7.07 (d, 1H), 7.19 (q, 2H), 7.67 (d, 1H), 8.05 (s, 1H), 8.62 (s, 1H), 12.99 (s, 1H). Anal Calcd for $C_{21}H_{23}N_5O_2$: C, 66.83; H, 6.14; N, 18.55. Found: C, 66.63; H, 5.99; N, 18.29.

Example 92

1-(1H-Indazol-4-yl)-3-(4-[1,4]oxazepan-4-yl-indan-1-yl)-urea

Example 92A

4-[1,4]Oxazepan-4-yl-indan-1-ylamine

The title compound was made according to the conditions described in Examples 56B-56C, except using [1,4]oxazepan instead of piperidine in ex. 56B.

Example 92B

4-[3-(4-[1,4]Oxazepan-4-yl-indan-1-yl)-ureido]-indazole-1'-carboxylic acid methyl ester The title compound was made according to the conditions described in Example 36I except using 3-[1,4]oxazapan-4-yl-indan-1-ylamine (Ex. 92A) instead of 5-(2-methoxy-1,1-dimethyl-ethyl)-indan-1-ylamine. MS (DCI) 450 (M+1).

Example 92C 1-(1H-Indazol-4-yl)-3-(4-[1,4]oxazepan-4-yl-indan-1-yl)-urea

The title compound was made from the compound in Ex. 92B according to the deprotection procedure by using 5M NaOH in methanol (example 9). MS (ESI) m/z: 392.12 $[M+H]^+$ ¹H NMR (DMSO-d₆) δ: 1.76 (m, 1H), 1.93 (m, 2H), 2.43 (m, 1H), 2.82 (m, 1H), 2.89 (m, 1H), 3.33 (m, 4H), 3.75 (m, 4H), 5.13 (q, 1H), 6.65 (d, 1H), 6.80 (d, 1H), 6.87 (d, 1H), 7.07 (d, 1H), 7.12 (t, 1H), 7.21 (t, 1H), 7.67 (d, 1H), 8.05 (s, 1H), 8.61 (s, 1H), 12.99 (s, 1H). Anal Calcd for $C_{22}H_{25}N_5O_2 \cdot 0.26MeOH$: C, 66.87; H, 6.56; N, 17.52. Found: C, 67.06; H, 6.32; N, 17.11.

Example 93

1-[4-(2,6-Dimethyl-morpholin-4-yl)-indan-1-yl]-3-(1H-indazol-4-yl)-urea

Example 93A 4-(2,6-Dimethyl-morpholin-4-yl)-indan-1-ylamine

The title compound was made according to the conditions described in Examples 56B-56C, except using 2,6-dimethyl-morpholine instead of piperidine in ex. 56B.

Example 93B

4-{3-[4-(2,6-Dimethyl-morpholin-4-yl)-indan-1-yl]-ureido}-indazole-1-carboxylic acid methyl ester The title compound was made according to the conditions described in Example 36I except using 4-(2,6-dimethyl-morpholin-4-yl)-indan-1-ylamine (Ex. 93A) instead of 5-(2-methoxy-1,1-dimethyl-ethyl)-indan-1-ylamine. MS (DCI) 463 (M+1).

Example 93C

1-[4-(2,6-Dimethyl-morpholin-4-yl)-indan-1-yl]-3-(1H-indazol-4-yl)-urea

The title compound was made from the compound in Ex. 93B according to the deprotection procedure by using 5M NaOH in methanol (example 9). MS (ESI) m/z: 406.18 [M+H]⁺. ¹H NMR (DMSO-d₆) δ: 1.13 (t, 5H), 1.26 (dd, 1H), 1.79 (m, 1H), 2.24 (t, 1H), 2.39 (t, 1H), 2.46 (m, 1H), 2.80 (m, 1H), 2.85 (m, 1H), 3.12 (d, 1H), 3.19 (d, 1H), 3.72 & 4.05 (pair of m, 2H), 5.16 (q, 1H), 6.67 (d, 1H), 6.81 (d, 1H), 6.99 (d, 1H), 7.08 (d, 1H), 7.18 (t, 1H), 7.22 (t, 1H), 7.67 (d, 1H), 8.05 (s, 1H), 8.61 (s, 1H), 13.00 (s, 1H). Anal Calcd for $C_{23}H_{27}N_5O_2$: C, 68.13; H, 6.71; N, 17.27. Found: C, 68.28; H, 6.71; N, 16.98.

Example 94

1-(1H-Indazol-4-yl)-3-[4-(4-methyl-piperazin-1-yl)-indan-1-yl]-urea

Example 94A 4-(4-Methyl-piperazin-1-yl)-indan-1-ylamine

The title compound was made according to the conditions described in Examples 56B-56C, except using 1-methyl-piperazine instead of piperidine in ex. 56B.

Example 94B

4-{3-[4-(4-Methyl-piperazin-1-yl)-indan-1-yl]-ureido}-indazole-1-carboxylic acid methyl ester The title compound was made according to the conditions described in Example 36I except using 4-(4-methyl-piperazin-1-yl)-indan-1-ylamine (Ex. 94A) instead of 5-(2-methoxy-1,1-dimethyl-ethyl)-indan-1-ylamine. MS (DCI) 449 (M+1).

Example 94

1-(1H-Indazol-4-yl)-3-[4-(4-methyl-piperazin-1-yl)-indan-1-yl]-urea

The title compound was made from the compound in Ex. 94B according to the deprotection procedure by using 5M NaOH in methanol (example 9). MS (ESI) m/z: 391.13 [M+H]⁺. ¹H NMR (DMSO-d₆) δ: 1.78 (m, 1H), 2.24 (s, 3H), 2.44 (m, 1H), 2.48 (m, 4H), 2.77 (m, 1H), 2.89 (m, 3H), 3.00 (m, 2H), 5.16 (q, 1H), 6.67 (d, 1H), 6.82 (d, 1H), 6.97 (d, 1H), 7.08 (d, 1H), 7.17 (t, 1H), 7.22 (t, 1H), 7.68 (d, 1H), 8.05 (s, 1H), 8.62 (s, 1H), 13.00 (s, 1H).

Anal Calcd for $C_{22}H_{26}N_6O \cdot 0.8H_2O \cdot 1.2MeOH$: C, 62.85; H, 7.37; N, 18.96. Found: C, 62.73; H, 7.48; N, 18.91.

Example 95

1-(1H-Indazol-4-yl)-3-(4-pyridin-3-yl-indan-1-yl)-urea

Example 95A

4-Pyridin-3-yl-indan-1-one O-methyl-oxime

4-Bromoindan-1-one O-methyloxime (720 mg, 3.0 mmol) was added to a mixture of pyridine-3-boronic acid (406 mg, 3.3 mmol), sodium carbonate (477 mg, 4.5 mmol) and Pd(dppf)Cl₂·CH₂Cl₂ (122 mg, 0.15 mmol) in 7:2:3 DME:EtOH:H₂O (15 mL). The stirred mixture was heated at 160° C. for 3 minutes on the microwave. After cooling to ambient temperature, the reaction mixture was filtered through celite, then silica gel with ethyl acetate. The filtrate was concentrated to a brown oil and chromatographed on silica gel with 70% ethyl acetate in hexane. Obtained 4-pyridin-3-yl-indan-1-one O-methyloxime (667 mg, 93%) as a yellow oil. MS (ESI) m/z: 239.1 [M+H]. ¹H NMR (DMSO-d₆) δ: 2.81 (m, 2H), 3.08 (m, 2H), 3.92 (s, 3H), 7.45 (m, 2H), 7.48 & 7.51 (pair of dd, 1H), 7.63 (dd, 1H), 7.94 & 7.97 (pair of dd, 1H), 8.60 (dd, 1H), 8.72 (dd, 1H).

Example 95B

4-Pyridin-3-yl-indan-1-ylamine

The title compound was made according to the conditions described in Example 1D, except using 4-pyridin-3-yl-indan-1-one O-methyl-oxime instead of 5-tert-Butyl-1-indanone O-methyloxime.

Example 95C

4-[3-(4-Pyridin-3-yl-indan-1-yl)-ureido]-indazole-1-carboxylic acid methyl ester The title compound was made according to the conditions described in Example 36I except using 4-Pyridin-3-yl-indan- 1-ylamine (Ex. 95B) instead of 5-(2-methoxy-1,1-dimethylethyl)-indan-1-ylamine. MS (DCI) 428 (M+1).

Example 95

1-(1H-Indazol-4-yl)-3-(4-pyridin-3-yl-indan-1-yl)-urea

The title compound was made from the compound in Ex. 95C according to the deprotection procedure by using 5M NaOH in methanol (example 9). MS (ESI) m/z: 370.07 [M+H]$^+$. $^1$H NMR (DMSO-d$_6$) δ: 1.84 (m, 1H), 2.47 (m, 1H), 3.00 (m, 2H), 5.30 (q, 1H), 6.77 (d, 1H), 7.09 (d, 1H), 7.23 (t, 1H), 7.39 (m, 3H), 7.50 & 7.53 (pair of dd, 1H), 7.68 (d, 1H), 7.92 (dt, 1H), 8.07 (t, 1H), 8.59 (dd, 1H), 8.66 (s, 1H), 8.72 (dd, 1H), 13.00 (s, 1H).
Anal Calcd for C$_{22}$H$_{19}$N$_5$O: C, 71.53; H, 5.18; N, 18.96. Found: C, 71.27; H, 5.21; N, 18.90.

Example 96

1-(1H-Indazol-4-yl)-3-(4-pyridin-4-yl-indan-1-yl)-urea

Example 96A

4-Pyridin-4-yl-indan-1-one O-methyl-oxime

The title compound was made according to the procedure described in Example 95A except using pyridine-3-boronic acid instead of pyridine-3-boronic acid.

Example 96B

4-Pyridin-4-yl-indan-1-ylamine

The title compound was made according to the conditions described in Example 1D, except using 4-pyridin-4-yl-indan-1-one O-methyloxime instead of 5-tert-Butyl-1-indanone O-methyloxime.

Example 96C

4-[3-(4-Pyridin-4-yl-indan-1-yl)-ureido]-indazole-1-carboxylic acid methyl ester The title compound was made according to the conditions described in Example 36I except using 4-pyridin-4-yl-indan-1-ylamine (Ex. 96B) instead of 5-(2-methoxy-1,1-dimethylethyl)-indan-1-ylamine. MS (DCI) 428 (M+1).

Example 96

1-(1H-Indazol-4-yl)-3-(4-pyridin-4-yl-indan-1-yl)-urea

The title compound was made from the compound in Ex. 96C according to the deprotection procedure by using 5M NaOH in methanol (example 9). MS (ESI) m/z: 370.00 [M+H]$^+$. $^1$H NMR (DMSO-d$_6$) δ: 1.84 (m, 1H), 2.47 (m, 1H), 3.03 (m, 2H), 5.28 (q, 1H), 6.78 (d, 1H), 7.09 (d, 1H), 7.23 (t, 1H), 7.41 (m, 3H), 7.52 (dd, 2H), 7.68 (d, 1H), 8.06 (s, 1H), 8.66 (m, 3H), 13.01 (s, 1H). Anal Calcd for C$_{22}$H$_{19}$N$_5$O: C, 71.53; H, 5.18; N, 18.96. Found: C, 71.22; H, 5.07; N, 18.79.

Example 97

1-(1H-Indazol-4-yl)-3-(4-pyridin-2-yl-indan-1-yl)-urea

Example 97A

4-Pyridin-2-yl-indan-1-one O-methyl-oxime

2-Pyridylzinc bromide (10 mL, 5 mmol, 0.5M in THF) was added to 4-bromoindan-1-one O-methyl-oxime (600 mg, 2.5 mmol) and Pd(PPh$_3$)$_4$ (58 mg, 0.05 mmol) under nitrogen atmosphere. The stirred solution was heated at 120° C. for 10 minutes on the microwave. After cooling to ambient temperature, the reaction mixture was filtered through celite, then silica gel with ethyl acetate. The filtrate was concentrated to a brown oil and chromatographed on silica gel with 20-40% ethyl acetate in hexane. Obtained 4-pyridin-2-ylindan-1-one O-methyloxime (326 mg, 55%) as a yellow oil. MS (DCI/NH$_3$) m/z: 239.09 [M+H]$^+$. $^1$H NMR (DMSO-d$_6$) δ: 2.82 (m, 2H), 3.29 (m, 2H), 3.92 (s, 3H), 7.36 & 7.38 (pair of dd, 1H), 7.43 (t, 1H), 7.64 (dd, 1H), 7.74 (dd, 1H), 7.75 (dt, 1H), 7.91 (td, 1H), 8.68 & 8.69 (pair of dd, 1H).

Example 97B

4-Pyridin-2-yl-indan-1-ylamine

The title compound was made according to the conditions described in Example 1D, except using 4-Pyridin-2-yl-indan-1-one O-methyl-oxime-instead of 5-tert-Butyl-1-indanone O-methyloxime.

Example 97C

4-[3-(4-Pyridin-2-yl-indan-1-yl)-ureido]-indazole-1-carboxylic acid methyl ester The title compound was made according to the conditions described in Example 36I except using 4-pyridin-2-yl-indan-1-ylamine (Ex. 97B) instead of 5-(2-methoxy-1,1-dimethylethyl)-indan-1-ylamine. MS (DCI) 428 (M+1).

Example 97

1-(1H-Indazol-4-yl)-3-(4-pyridin-2-yl-indan-1-yl)-urea

The title compound was made from the compound in Ex. 97C according to the deprotection procedure by using 5M NaOH in methanol (example 9). MS (ESI) m/z: 370.0 [M+H]$^+$. $^1$H NMR (DMSO-d$_6$) δ: 1.83 (m, 1H), 2.47 (m, 1H), 3.12 (m, 2H), 5.29 (q, 1H), 6.78 (d, 1H), 7.09 (d, 1H), 7.23 (t, 1H), 7.38 (m, 3H), 7.63 (dd, 1H), 7.69 (d, 1H), 7.70 (dt, 1H), 7.91 (td, 1H), 8.06 (s, 1H), 8.64 (s, 1H), 8.69 & 8.70 (pair of dd, 1H), 13.01 (s, 1H).
Anal Calcd for C$_{22}$H$_{19}$N$_5$O.0.16H$_2$O: C, 70.97; H, 5.23; N, 18.81. Found: C, 70.93; H, 5.21; N, 18.91.

Example 98

1-[4-(4-Fluoro-piperidin-1-yl)-indan-1-yl]-3-(1H-indazol-4-yl)-urea

Example 98A

4-(4-Fluoro-piperidin-1-yl)-indan-1-ylamine

The title compound was made according to the conditions described in Examples 56B-56C, except using 4-fluoro-piperidine instead of piperidine in ex. 56B.

Example 98B

4-{3-[4-(4-Fluoro-piperidin-1-yl)-indan-1-yl]-ureido}-indazole-1-carboxylic acid methyl ester The title compound was made according to the conditions described in Example 36I except using 4-(4-fluoro-piperidin-1-yl)-indan-1-ylamine (Ex. 98A) instead of 5-(2-methoxy-1,1-dimethyl-ethyl)-indan-1-ylamine. MS (DCI) 452 (M+1).

Example 98C

The title compound was made from the compound in Ex. 98B according to the deprotection procedure by using 5M NaOH in methanol (example 9). MS (ESI) m/z: 394.08 [M+H]$^+$. $^1$H NMR (DMSO-d$_6$) δ: 1.75-2.08 (m, 5H), 2.45 (m, 1H), 2.74-3.14 (m, 6H), 4.76 & 4.92 (pair of 7, 1H), 5.19 (q, 1H), 6.67 (d, 1H), 6.85 (d, 1H), 6.98 (d, 1H), 7.07 (d, 1H), 7.17 (t, 1H), 7.22 (t, 1H), 7.67 (d, 1H), 8.05 (s, 1H), 8.62 (s, 1H), 13.00 (s, 1H).
Anal Calcd for $C_{22}H_{24}N_5OF.0.38H_2O$: C, 66.01; H, 6.23; N, 17.49. Found: C, 66.10; H, 6.54; N, 17.22.

Example 99

1-[4-(3-Fluoro-piperidin-1-yl)-indan-1-yl]-3-(1H-indazol-4-yl)-urea

Example 99A

4-(3-Fluoro-piperidin-1-yl)-indan-1-ylamine

The title compound was made according to the conditions described in Examples 56B-56C, except using 3-fluoro-piperidine instead of piperidine in ex. 56B.

Example 99B

4-{3-[4-(3-Fluoro-piperidin-1-yl)-indan-1-yl]-ureido}-indazole-1-carboxylic acid methyl ester The title compound was made according to the conditions described in Example 36I except using 4-(3-fluoro-piperidin-1-yl)-indan-1-ylamine (Ex. 99A) instead of 5-(2-methoxy-1,1-dimethyl-ethyl)-indan-1-ylamine. MS (DCI) 452 (M+1).

Example 99C

1-[4-(3-Fluoro-piperidin-1-yl)-indan-1-yl]-3-(1H-indazol-4-yl)-urea

The title compound was made from the compound in Ex. 99B according to the deprotection procedure by using 5M NaOH in methanol (example 9). MS (ESI) m/z: 394.11 [M+H]$^+$. $^1$H NMR (DMSO-d$_6$) δ: 1.62-1.98 (m, 5H), 2.44 (m, 1H), 2.73-3.03 (m, 5H), 3.11 (m, 1H), 4.72 & 4.88 (pair of m, 1H), 5.19 (q, 1H), 6.69 (d, 1H), 6.84 (d, 1H), 6.98 (d, 1H), 7.08 (d, 1H), 7.18 (t, 1H), 7.22 (t, 1H), 7.67 (d, 1H), 8.05 (s, 1H), 8.62 (d, 1H), 12.99 (s, 1H).
Anal Calcd for $C_{22}H_{24}N_5OF.0.18H_2O$: C, 66.61; H, 6.19; N, 17.65. Found: C, 66.66; H, 6.61; N, 17.51.

Example 100

1-[4-(3,3-Difluoro-piperidin-1-yl)-indan-1-yl]-3-(1H-indazol-4-yl)-urea

Example 100A

4-(3,3-difluoro-piperidin-1-yl)-indan-1-ylamine

The title compound was made according to the conditions described in Examples 56B-56C, except using 3,3-difluoro-piperidine instead of piperidine in ex. 56B.

Example 100B

4-{3-[4-(3,3-difluoro-piperidin-1-yl)-indan-1-yl]-ureido}-indazole-1-carboxylic acid methyl ester The title compound was made according to the conditions described in Example 36I except using 4-(3,3-difluoro-piperidin-1-yl)-indan-1-ylamine (Ex. 100A) instead of 5-(2-methoxy-1,1-dimethyl-ethyl)-indan-1-ylamine. MS (DCI) 470 (M+1).

Example 100C

1-[4-(3,3-difluoro-piperidin-1-yl)-indan-1-yl]-3-(1H-indazol-4-yl)-urea

The title compound was made from the compound in Ex. 100B according to the deprotection procedure by using 5M NaOH in methanol (example 9). MS (ESI) m/z: 412.04 [M+H]$^+$. $^1$H NMR (DMSO-d$_6$) δ: 1.82 (m, 3H), 2.04 (7, 2H), 2.46 (m, 1H), 2.81 (m, 2H), 2.93 (m, 1H), 3.05 (m, 1H), 3.19 (t, 1H), 3.29 (t, 1H), 5.20 (q, 1H), 6.67 (d, 1H), 6.86 (d, 1H), 7.01 (d, 1H), 7.08 (d, 1H), 7.19 (q, 2H), 7.67 (d, 1H), 8.05 (s, 1H), 8.63 (s, 1H), 13.00 (s, 1H).
Anal Calcd for $C_{22}H_{23}N_5OF_2.0.98H_2O$: C, 61.58; H, 5.86; N, 16.32. Found: C, 61.63; H, 5.32; N, 15.95.

Example 101

1-[4-(4,4-Difluoro-piperidin-1-yl)-indan-1-yl]-3-(1H-indazol-4-yl)-urea

Example 101A

4-(4,4-Difluoro-piperidin-1-yl)-indan-1-ylamine

The title compound was made according to the conditions described in Examples 56B-56C, except using 4,4-difluoro-piperidine instead of piperidine in ex. 56B.

Example 101B

4-{3-[4-(4,4-Difluoro-piperidin-1-yl)-indan-1-yl]-ureido}-indazole-1-carboxylic acid methyl ester The title compound was made according to the conditions described in Example 36I except using 4-(4,4-difluoro-piperidin-1-yl)-indan-1-ylamine (Ex. 101A) instead of 5-(2-methoxy-1,1-dimethyl-ethyl)-indan-1-ylamine. MS (DCI) 470 (M+1).

Example 101C

1-[4-(4,4-Difluoro-piperidin-1-yl)-indan-1-yl]-3-(1H-indazol-4-yl)-urea

The title compound was made from the compound in Ex. 101B according to the deprotection procedure by using 5M NaOH in methanol (example 9). MS (ESI) m/z: 412.04 $[M+H]^+$. $^1$H NMR (DMSO-$d_6$) δ: 1.80 (m, 1H), 2.12 (m, 4H), 2.46 (m, 1H), 2.81 (m, 1H), 2.88 (m, 1H), 3.05 (m, 2H), 3.11 (m, 2H), 5.20 (q, 1H), 6.68 (d, 1H), 6.89 (d, 1H), 7.01 (d, 1H), 7.08 (d, 1H), 7.22 (q, 2H), 7.67 (d, 1H), 8.05 (s, 1H), 8.62 (s, 1H), 13.00 (s, 1H). Anal Calcd for $C_{22}H_{23}N_5OF_2$: C, 64.22; H, 5.63; N, 17.02. Found: C, 64.49; H, 5.50; N, 16.72.

(5) Determination of Biological Activity (a) In Vitro Data—Determination of Inhibition Potencies Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/l Na pyruvate, without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNAs for the human VR1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain Vol. 88 pages 205-215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with growth medium containing 800 μg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 μg/mL G418 (Cal-biochem) and 10% fetal bovine serum under a humidified 5% $CO_2$ atmosphere.

The functional activity of compounds at the VR1 receptor was determined with a $Ca^{2+}$ influx assay and measurement of intracellular $Ca^{2+}$ levels ($[Ca^{2+}]i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 μM solution of the VR1 agonist capsaicin was also prepared in D-PBS. The fluorescent $Ca^{2+}$ chelating dye fluo-4 was used as an indicator of the relative levels of $[Ca^{2+}]i$ in a 96-well format using a Fluorescence Imaging Plate Reader (FLIPR) (Molecular Devices, Sunnyvale, Calif.). Cells were grown to confluency in 96-well black-walled tissue culture plates. Then, prior to the assay, the cells were loaded with 100 μL per well of fluo-4 AM (2 μM, in D-PBS) for 1-2 hours at 23° C. Washing of the cells was performed to remove extracellular fluo-4 AM (2×1 mL D-PBS per well), and afterward, the cells were placed in the reading chamber of the FLIPR instrument. 50 μL of the compound solutions were added to the cells at the 10 second time mark of the experimental run. Then, after a 3 minute time delay, 50 μL of the capsaicin solution was added at the 190 second time mark (0.05 μM final concentration) (final volume=200 μL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 μM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present invention were found to be antagonists of the vanilloid receptor subtype 1 (VR1) receptor with $IC_{50}$, from about 2200 nM to about 1.0 nM. In a preferred range, compounds tested had $IC_{50}$, from about 200 nM to about 1.0 nM.

(b) In Vivo Data—Determination of Antinociceptive Effect

Experiments were performed on 400 adult male 129J mice (Jackson Laboratories, Bar Harbor, Me.), weighing 20-25 g and male Sprague-Dawley rats (Charles River, Wilmington, Mass.) weighing 200-300 grams were utilized. Animals were kept in a vivarium, maintained at 22° C., with a 12 hour alternating light-dark cycle with food and water available ad libitum. All experiments were performed during the light cycle. Animals were randomly divided into separate groups of 6 animals each. Each animal was used in one experiment only and was sacrificed immediately following the completion of the experiment. All animal handling and experimental procedures were approved by an IACUC Committee.

The antinociceptive test used was a modification of the abdominal constriction assay described in Collier, et al., Br. J. Pharmacol. Chemother. Vol. 32 pages 295-310, (1968). Each animal received an intraperitoneal (i.p.) injection of 0.3 mL of 0.6% acetic acid in normal saline to evoke writhing. Animals were placed separately under clear cylinders for the observation and quantification of abdominal constriction. Abdominal constriction was defined as a mild constriction and elongation passing caudally along the abdominal wall, accompanied by a slight twisting of the trunk and followed by bilateral extension of the hind limbs. The total number of abdominal constrictions was recorded from 5 to 20 minutes after acetic acid injection. The $ED_{50s}$ were determined based on the i.p. injection.

The other antinociceptive test used was Complete Freund's Adjuvant-induced Thermal Hyperalgesia (CFA) assay described in Pircio et al. Eur J. Pharmacol. Vol. 31(2) pages 207-215 (1975). Chronic inflammatory hyperalgesia was induced in one group of rats following the injection of complete Freund's adjuvant (CFA, 50%, 150 ul) into the plantar surface of the right hindpaw 48 hours prior to testing. Thermal nociceptive thresholds were measured in three different groups of rats. The $ED_{50}$, were determined based on the oral administration.

The compounds of the present invention tested were found to have antinociceptive effects with $ED_{50}$, from about 1 mg/kg to about 500 mg/kg.

The in vitro and in vivo data demonstrates that compounds of the present invention antagonize the VR1 receptor and are useful for treating pain.

Compounds of the present invention are also useful for ameliorating or preventing additional disorders such as, but not limited to, inflammatory thermal hyperalgesia, bladder overactivity, and urinary incontinence as described by Nolano, M. et al., *Pain Vol.* 81 page 135 (1999); Caterina, M. J. and Julius, D., *Annu. Rev. Neurosci. Vol.* 24, pages 487-517 (2001); Caterina, M. J. et al., *Science Vol.* 288 pages 306-313 (2000); Caterina, M. J. et al., *Nature Vol.* 389 pages 816-824 (1997); Fowler, C. *Urology Vol.* 55 page 60 (2000); and Davis, J. et al., *Nature Vol.* 405 pages 183-187 (2000).

What is claimed is:

1. A compound selected from the group consisting of
  N-(5-chloro-2,3-dihydro-1H-inden-1-yl)-N'-1H-indazol-4-ylurea;
  N-(5-fluoro-2,3-dihydro-1H-inden-1-yl)-N'-1H-indazol-4-ylurea;
  N-(4,5-dimethoxy-2,3-dihydro-1H-inden-1-yl)-N'-1H-indazol-4-ylurea;
  N-1H-indazol-4-yl-N'-(5-methoxy-2,3-dihydro-1H-inden-1-yl)urea;
  N-(5,6-dimethoxy-2,3-dihydro-1H-inden-1-yl)-N'-1H-indazol-4-ylurea;
  N-1H-indazol-4-yl-N'-(6-methoxy-2,3-dihydro-1H-inden-1-yl)urea;
  N-[(1S)-4,5-dimethoxy-2,3-dihydro-1H-inden-1-yl]-N'-1H-indazol-4-ylurea;
  N-[(1R)-4,5-dimethoxy-2,3-dihydro-1H-inden-1-yl]-N'-1H-indazol-4-ylurea;
  N-1H-indazol-4-yl-N'-[(1S)-5-methoxy-2,3-dihydro-1H-inden-1-yl]urea;
  N-1H-indazol-4-yl-N'-[(1R)-5-methoxy-2,3-dihydro-1H-inden-1-yl]urea;
  N-1H-indazol-4-yl-N'-[5-(2-methoxy-1,1-dimethylethyl)-2,3-dihydro-1H-inden-1-yl]urea;
  N-[5-(2-hydroxy-1,1-dimethylethyl)-2,3-dihydro-1H-inden-1-yl]-N'-1H-indazol-4-ylurea;
  N-(5-tert-butyl-2-fluoro-2,3-dihydro-1H-inden-1-yl)-N'-1H-indazol-4-ylurea;
  N-[(1R,2S)-5-tert-butyl-2-fluoro-2,3-dihydro-1H-inden-1-yl]-N'-1H-indazol-4-ylurea;
  N-[(1S,2S)-5-tert-butyl-2-fluoro-2,3-dihydro-1H-inden-1-yl]-N'-1H-indazol-4-ylurea;
  N-[(1S,2R)-5-tert-butyl-2-fluoro-2,3-dihydro-1H-inden-1-yl]-N'-1H-indazol-4-ylurea;
  N-1H-indazol-4-yl-N'-(6-fluoro-2,3-dihydro-1H-inden-1-yl)urea;
  N-1H-indazol-4-yl-N'-(6-methyl-2,3-dihydro-1H-inden-1-yl)urea;
  N-(5-tert-butyl-2,2-difluoro-2,3-dihydro-1H-inden-1-yl)-N'-1H-indazol-4-ylurea;
  1-(5-tert-butyl-indan-2-yl)-3-(1H-indazol-4-yl)-urea;
  N-1H-indazol-4-yl-N'-(7-methyl-2,3-dihydro-1H-inden-1-yl)urea;
  N-1H-indazol-4-yl-N'-(5-methyl-2,3-dihydro-1H-inden-1-yl)urea;
  N-1H-indazol-4-yl-N'-(5-isopropyl-2,3-dihydro-1H-inden-1-yl)urea;
  1-[5-(Cyano-isopropyl)-indan-1-yl]-3-(1H-indazol-4-yl)-urea;
  N-[(1R)-5-(1-cyano-1-methylethyl)-2,3-dihydro-1H-inden-1-yl]-N'-1H-indazol-4-ylurea;
  N-[(1S)-5-(1-cyano-1-methylethyl)-2,3-dihydro-1H-inden-1-yl]-N'-1H-indazol-4-ylurea;
  N-1H-indazol-4-yl-N'-[4-(trifluoromethyl)-2,3-dihydro-1H-inden-1-yl]urea;
  N-(4-chloro-2,3-dihydro-1H-inden-1-yl)-N'-1H-indazol-4-ylurea;
  N-1H-indazol-4-yl-N'-[4-(trifluoromethoxy)-2,3-dihydro-1H-inden-1-yl]urea;
  N-(4-bromo-2,3-dihydro-1H-inden-1-yl)-N'-1H-indazol-4-ylurea;
  N-[4-(cyanomethyl)-2,3-dihydro-1H-inden-1-yl]-N'-1H-indazol-4-ylurea; and
  N-1H-indazol-4-yl-N'-(4-methyl-2,3-dihydro-1H-inden-1-yl)urea;
  or a pharmaceutically acceptable salt thereof.

2. A compound that is amorphous N-[(1R)-5-tert-butyl-2,3-dihydro-1H-inden-1-yl]-N'-1H-indazol-4-ylurea, or a pharmaceutically acceptable salt thereof.

3. A compound selected from the group consisting of
  N-[(1R)-5-tert-butyl-2,3-dihydro-1H-inden-1-yl]-N'-1H-indazol-4-ylurea, hydrochloride;
  N-[(1R)-5-tert-butyl-2,3-dihydro-1H-inden-1-yl]-N'-1H-indazol-4-ylurea, tosylate; and
  N-[(1R)-5-tert-butyl-2,3-dihydro-1H-inden-1-yl]-N'-1H-indazol-4-ylurea, benzenesulfonate.

4. A compound selected from the group consisting of
  N-(1-acetyl-1H-indazol-4-yl)-N'-(5,6-dimethoxy-2,3-dihydro-1H-inden-1-yl)urea; and
  N-(1-acetyl-1H-indazol-4-yl)-N'-[(1R)-5-tert-butyl-2,3-dihydro-1H-inden-1-yl]urea;
  or a pharmaceutically acceptable salt thereof.

5. A compound selected from the group consisting of
  N-(6-fluoro-5-piperidin-1-yl-2,3-dihydro-1H-inden-1-yl)-N'-1H-indazol-4-ylurea;
  N-1H-indazol-4-yl-N'-(4-piperidin-1-yl-2,3-dihydro-1H-inden-1-yl)urea;
  N-1H-indazol-4-yl-N'-{5-[4-(trifluoromethyl)piperidin-1-yl]-2,3-dihydro-1H-inden-1-yl}urea;
  N-1H-indazol-4-yl-N'-(5-cis-octahydroisoquinolin-2(1H)-yl-2,3-dihydro-1H-inden-1-yl)urea;
  N-[5-(1,4'-bipiperidin-1'-yl)-2,3-dihydro-1H-inden-1-yl]-N'-1H-indazol-4-ylurea;
  N-1H-indazol-4-yl-N'-[5-(4-phenylpiperidin-1-yl)-2,3-dihydro-1H-inden-1-yl]urea;
  N-1H-indazol-4-yl-N'-[5-(4-phenylpiperazin-1-yl)-2,3-dihydro-1H-inden-1-yl]urea;
  N-1H-indazol-4-yl-N'-[5-(4-methylpiperidin-1-yl)-2,3-dihydro-1H-inden-1-yl]urea;
  N-1H-indazol-4-yl-N'-[5-(3-methylpiperidin-1-yl)-2,3-dihydro-1H-inden-1-yl]urea;
  N-1H-indazol-4-yl-N'-[5-(2-oxopiperidin-1-yl)-2,3-dihydro-1H-inden-1-yl]urea;
  N-1H-indazol-4-yl-N'-[5-(2-methylpiperidin-1-yl)-2,3-dihydro-1H-inden-1-yl]urea;
  N-(4-azepan-1-yl-2,3-dihydro-1H-inden-1-yl)-N'-1H-indazol-4-ylurea;
  N-1H-indazol-4-yl-N'-[4-(4-methylpiperidin-1-yl)-2,3-dihydro-1H-inden-1-yl]urea;
  N-1H-indazol-4-yl-N'-[4-(3-methylpiperidin-1-yl)-2,3-dihydro-1H-inden-1-yl]urea;
  N-1H-indazol-4-yl-N'-[4-(2-methylpiperidin-1-yl)-2,3-dihydro-1H-inden-1-yl]urea;

N-1H-indazol-4-yl-N'-[(1R)-4-piperidin-1-yl-2,3-dihydro-1H-inden-1-yl]urea;
N-1H-indazol-4-yl-N'-[(1S)-4-piperidin-1-yl-2,3-dihydro-1H-inden-1-yl]urea;
N-1H-indazol-4-yl-N'-(4-pyrrolidin-1-yl-2,3-dihydro-1H-inden-1-yl)urea;
N-1H-indazol-4-yl-N'-[4-(2-methylpyrrolidin-1-yl)-2,3-dihydro-1H-inden-1-yl]urea;
N-[4-(2-azabicyclo[2.2.1]hept-2-yl)-2,3-dihydro-1H-inden-1-yl]-N'-1H-indazol-4-ylurea;
N-1H-indazol-4-yl-N'-(4-octahydroisoquinolin-2(1H)-yl-2,3-dihydro-1H-inden-1-yl)urea;
1-[5-(1,1-Dioxo-1-thiomorpholin-4-yl)-indan-1-yl]-3-(1H-indazol-4-yl)-urea;
1-(1H-Indazol-4-yl)-3-(4-morpholin-4-yl-indan-1-yl)-urea;
1-(1H-Indazol-4-yl)-3-(4-[1,4]oxazepan-4-yl-indan-1-yl)-urea;
1-[4-(2,6-Dimethyl-morpholin-4-yl)-indan-1-yl]-3-(1H-indazol-4-yl)-urea;
1-(1H-Indazol-4-yl)-3-[4-(4-methyl-piperazin-1-yl)-indan-1-yl]-urea;
1-(1H-Indazol-4-yl)-3-(4-pyridin-3-yl-indan-1-yl)-urea;
1-(1H-Indazol-4-yl)-3-(4-pyridin-4-yl-indan-1-yl)-urea;
1-(1H-Indazol-4-yl)-3-(4-pyridin-2-yl-indan-1-yl)-urea;
1-[4-(4-Fluoro-piperidin-1-yl)-indan-1-yl]-3-(1H-indazol-4-yl)-urea;
1-[4-(3-Fluoro-piperidin-1-yl)-indan-1-yl]-3-(1H-indazol-4-yl)-urea;
1-[4-(3,3-Difluoro-piperidin-1-yl)-indan-1-yl]-3-(1H-indazol-4-yl)-urea; and
1-[4-(4,4-Difluoro-piperidin-1-yl)-indan-1-yl]-3-(1H-indazol-4-yl)-urea;

or a pharmaceutically acceptable salt thereof.

* * * * *